US009005962B2

(12) United States Patent
Morrison et al.

(10) Patent No.: US 9,005,962 B2
(45) Date of Patent: Apr. 14, 2015

(54) REGIONALISED ENDODERM CELLS AND USES THEREOF

(75) Inventors: Gillian Mary Morrison, Cambridge (GB); Joshua Mark Brickman, Edinburgh (GB); Ifigenia Oikonomopoulou, Athens (GR)

(73) Assignee: The University Court of the University of Edinburgh, Edinburgh (GB)

(*) Notice: Subject to any disclaimer, the term of this patent is extended or adjusted under 35 U.S.C. 154(b) by 450 days.

(21) Appl. No.: 12/674,890

(22) PCT Filed: Aug. 25, 2008

(86) PCT No.: PCT/GB2008/002875
§ 371 (c)(1),
(2), (4) Date: Feb. 23, 2010

(87) PCT Pub. No.: WO2009/027654
PCT Pub. Date: Mar. 5, 2009

(65) Prior Publication Data
US 2012/0100115 A1    Apr. 26, 2012

(30) Foreign Application Priority Data

Aug. 24, 2007 (GB) .................................. 0716515.2
May 30, 2008 (GB) .................................. 0809852.7

(51) Int. Cl.
*C12N 15/00* (2006.01)
*C12N 5/00* (2006.01)
*C12N 5/02* (2006.01)
*C12N 5/073* (2010.01)

(52) U.S. Cl.
CPC .......... *C12N 5/0603* (2013.01); *C12N 2501/11* (2013.01); *C12N 2501/115* (2013.01); *C12N 2501/119* (2013.01); *C12N 2501/155* (2013.01); *C12N 2501/16* (2013.01); *C12N 2501/165* (2013.01); *C12N 2501/385* (2013.01); *C12N 2506/02* (2013.01)

(58) Field of Classification Search
CPC .......... C12N 2501/119; C12N 5/0603; C12N 2501/155; C12N 2501/165; C12N 2501/115; C12N 2501/385; C12N 2501/16; C12N 2506/02; C12N 2501/11
USPC .......................................... 435/325, 354, 366
See application file for complete search history.

(56) References Cited

FOREIGN PATENT DOCUMENTS

WO    WO 2007051038 A2 *   5/2007
WO    2007/103282 A2    9/2007

OTHER PUBLICATIONS

McLin et al. Development, 134: 2207-2217, 2007.*
Cao et al. J. of Exp. Zoo., 311A: 368-376, 2009.*
Brevini et al. Theriogenology, 74: 544-550, 2010.*
Paris et al. Theriogenology, 74: 516-524, 2010.*
Kanai-Azuma et al., Development, 129: 2367-2379, 2002.*
"Substantially", Merriam-Webster, accessed online at http://www.merriam-webster.com/dictionary/substantially, May 2, 2013.*
Nih. Stem Cells: Scientific Progress and Future Research Directions, Department of Health and Human Services, Chapter 1, pp. 1-4, Jun. 2001.*
Jaenisch et al., Cell, 132: 567-582, 2008.*
Chen et al., Development: 140(3): 675-686, 2013.*
Rodaway et al., "Mesendoderm: An Ancient Germ Layer?", Cell, Apr. 2001, vol. 105, No. 2, pp. 169-172.
Bottcher RT et al., Endocrine Reviewes, "Fibroblast Growth Factor Signaling During Early Vertebrate Development", 2005, vol. 26, No. 1, pp. 63-77.
Angerer LM et al., Developmental Biology, "Animal-Vegetal Axis Patterning Mechanisms in the Early Sea Urchin Embryo", 2000, vol. 218, No. 1, pp. 1-12.
Bagutti C et al., Developmental Biology, "Differentiation of Embryonal Stem Cells Into Keratinocytes: Comparison of Wild-Type and B1 Intergrin-Deficient Cells", 1996, vol. 179, No. 1, pp. 184-196.
Beck F. et al., Developmental Dynamics, "Expression of CDX-2 in the Mouse Embryo and Placenta: Possible Role in Patterning of the Exra-Embryonic Membranes", 1995, vol. 204, No. 3, pp. 219-227.
Beddington S. P. et al., Trends in Genetics, "Anterior Patterning in Mouse", 1988, vol. 14, No. 7, pp. 277-284.
Barbera et al, Development, "The Homeobox Gene Hex Is Required in Definitive Endodermal Tissues for Normal Forebrain, Liver and Thyroid Formation", 2000, vol. 127, No. 11, pp. 2433-2445.
Beddington, Rosa S. P. et al., Cell, "Axis Development and Early Asymmetry in Mammals", 1999, vol. 96, No. 2, pp. 195-209.
Bennett, Christina N. et al., Journal of Biological Chemistry, "Regulation of WNT Signaling During Adipogenesis", 2002, vol. 277, No. 34, pp. 30998-31004.
Brickman, Joshua M. et al., Development, "Hex is a Transcriptional Repressor That Contributes to Anterior Identity and Suppresses Spemann Organiser Function", 2000, vol. 127, No. 11, pp. 2303-2315.
Brons, Gabrielle M. et al., Nature, "Derivation of Pluripotent Epiblast Stem Cells From Mammalian Embryos", 2007, vol. 448, Number , pp. 191-196.
Chen Y et al., Nature, "The Zebrafish Nodal Signal Squint Functions as a Morphogen", 2001, vol. 411, No. 6837, pp. 607-610.
Camus Anne et al., Developmental Biology, "Absence of Nodal Signaling Promotes Precocious Neural Differentiation in the Mouse Embryo", 2006, vol. 295, No. 2, pp. 743-755.
Cao et al., The Journal of Experimental Zoology., "Isolation and Culture of Primary Bovine Embryonic Stem Cell Colonies by a Novel Method", 2009, vol. 311A, Number , pp. 368-376.

(Continued)

*Primary Examiner* — Thaian N Ton
(74) *Attorney, Agent, or Firm* — Leon Y. Lum

(57) ABSTRACT

The present invention relates to the generation of anterior definitive endoderm (ADE) cells from embryonic stem cells and the differentiation of such cells to, for example, pancreatic or liver cells. The invention also relates to cell lines, cell culture methods, cells markers and the like and their potential uses in a variety of applications.

6 Claims, 41 Drawing Sheets

(56) References Cited

OTHER PUBLICATIONS

Casey ES et al., Development, "The T-Box Transcription Factor Branchyury Regulates Expression of EFGF Through Binding to a Non-Palindromic Response Element", 1998, vol. 125, No. 19, pp. 3887-3894.

Ciruna B et al., Developmental, "FGF Signaling Regulates Mesoderm Cell Fate Specification and Morphogenetic Movement at the Primitive Streak", 2001, vol. 1, No. 1, pp. 37-49.

Ciruna BG et al., Development, "Chimeric Analysis of Fibroblast Growth Factor Receptor-1 (FGFR1) Function: A Role for FGFR1 in Morphogenetic Movement Through the Primitive Streak", 1997, vol. 124, No. 14, pp. 2829-2841.

Conti L et al., PLoS Biology, "Niche-Independent Symmetrical Self-Renewal of a Mammalian Tissue Stem Cell", 2005, vol. 3, No. 9, pp. e283.

Cornell RA et al., Development, "FGF ISA Prospective Competence Factor for Early Activin-Type Signals in Xenopus Mesoderm Induction", 1995, vol. 121, Number , pp. 2429-2437.

D'Amour, Kevin A et al., Nature Biotechnology (Continuation of Bio/Technology), "Efficient Differentiation of Human Embryonic Stem Cells to Definitive Endoderm", 2005, vol. 23, No. 12, pp. 1534-1541.

Davidson, Eric H et al., Science, "A Genomic Regulatory Network for Development", 2002, vol. 295, No. 5560, pp. 1669-1678.

Deng et al., Genes & Development, "Murine FGFR-1 Is Required for Early Postimplantation Growth and Axial Organization", 1994, vol. 8, No. 24, pp. 3045-3057.

Deutsch, Gail et al., Development, "A Bipotential Precursor Population for Pancreas and Liver Within the Embryonic Endoderm", 2001, vol. 128, No. 6, pp. 871-881.

Dyson S et al., Cell, "The Interpretation of Position in a Morphogen Gradient as Revealed by Occupancy of Activin Receptors", 1998, vol. 93, No. 4, pp. 557-568.

D'Amour, Kevin A et al., Nature Biotechnology (Continuation of Bio/Technology), "Production of Pancreatic Hormone-Expressing Endocrine Cells From Human Embryonic Stem Cells", 2006, vol. 24, No. 11, pp. 1392-1401.

Finley K. R et al., Gene Expression Patterns, "The Mouse Secreted Frizzled-Related Protein 5 Gene is Expressed in the Anterior Visceral Endoderm and Foregut Endoderm During Early Post-Implantation Development", 2003, vol. 3, No. 5, pp. 681-684.

Friedman J R et al., Cell and Molecular Life Sciences, "The FOXA Family of Transcription Factors in Development and Metabolism", 2006, vol. 63, No. 19-20, pp. 2317-2328.

Gadue P et al., Proceedings of the National Academy of Sciences USA, "WNT and TGF—Beta Signaling Are Required for the Induction of an in Vitro Model of Primitive Streak Formation Using Embryonic Stem Cells", 2006, vol. 103, No. 45, pp. 16806-16811.

Gouon-Evans, Valerie et al., Nature Biotechnology (Continuation of Bio/Technology), "BMP-4 is Required for Hepatic Specification of Mouse Embryonic Stem Cell-Derived Definitive Endoderm", 2006, vol. 24, No. 11, pp. 1402-1411.

Green JB et al., Nature, "Graded Changes in Dose of a Xenopus Activin A Homologue Elicit Stepwise Transitions in Embryonic Cell Fate", 1990, vol. 347, No. 6291, pp. 391-394.

Hart, Adam H. et al., Development, "MIXL1 is Required for Axial Mesendoderm Morphogenesis and Patterning in the Murine Embryo", 2002, vol. 129, No. 15, pp. 3597-3608.

Hay D.C et al., Stem Cells, "Efficient Differentiation of Hepatocytes From Human Embryonic Stem Cells Exhibiting Markers Recapitulating Liver Development in Vivo", 2008, vol. 26, Number , pp. 894-902.

Hay, David C. et al., Proceedings of the National Academy of Sciences of the USA, "Highly Efficient Differentiation of HESCS to Functional Hepatic Endoderm Requires Activin A and WNT3A Signaling", 2008, vol. 105, No. 34, pp. 12301-12306.

Hebrok M et al., Genes & Development, "Notochord Repression of Endodermal Sonic Hedgehog Permits Pancreas Development", 1998, vol. 12, No. 11, pp. 1705-1713.

Huber O et al., Current Opinion in Cell Biology, "Cadherins and Catenins in Development", 1996, vol. 8, No. 5, pp. 685-691.

Kennedy M et al., Methods in Enzymology, "Hematopoietic Commitment of ES Cells in Culture", 2003, vol. 365, Number , pp. 39-59.

Kanai-Azuma, Masami et al., Development, "Depletion of Definitive Gut Endoderm in SOX17-Null Mutant Mice", 2002, vol. 129, No. 10, pp. 2367-2379.

Kinder, Simon J. et al., Development, "The Organizer of the Mouse Gastrula is Composed of a Dynamic Population of Progenitor Cells for the Axial Mesoderm", 2001, vol. 128, No. 18, pp. 3623-3634.

Knop et al., Biotechniques, "Improved Version of the Red Fluorescent Protein (DRFP583/DSRED/RFP)", 2002, vol. 33, No. 3, pp. 592-602.

Kubo et al, Blood, "The Homeobox Gene Hex Regulates Proliferation and Differentiation of Hemangioblasts and Endothelial Cells During ES Cell Differentiation", 2005, vol. 105, No. 12, pp. 4590-4597.

Kubo et al, Development, "Development of Definitive Endoderm From Embryonic Stem Cells in Culture", 2004, vol. 131, No. 7, pp. 1651-1662.

Kumar et al, Developmental Biology, "Signals From Lateral Plate Mesoderm Instruct Endoderm Toward a Pancreatic Fate", 2003, vol. 259, No. 1, pp. 109-122.

Kunath et al, Development, "FGF Stimulation of the ERK1/2 Signalling Cascade Triggers Transition of Pluripotent Embryonic Stem Cells From Self-Renewal to Lineage Commitment", 2007, vol. 134, No. 16, pp. 2895-2902.

LaBonne et al, Development, "Mesoderm Induction by Activin Requires FGF-Mediated Intracellular Signals", 1994, vol. 120, No. 2, pp. 463-472.

Lawson et al, Development, "Cell Fate, Morphogenetic Movement and Population Kinetics of Embryonic Endoderm at the Time of Germ Layer Formation in the Mouse", 1987, vol. 101, No. 3, pp. 627-652.

Li et al, Nature, "Essential Function of LIF Receptor in Motor Neurons", 1995, vol. 378, No. 6558, pp. 724-727.

Lickert et al, Developmental cell, "Formation of Multiple Hearts in Mice Following Deletion of B-Catenin in the Embryonic Endoderm", 2002, vol. 3, No. 2, pp. 171-181.

Lu et al, Current Opinion in Genetics & Development, "From Fertilization to Gastrulation: Axis Formation in the Mouse Embryo", 2001, vol. 11, No. 4, pp. 384-392.

Maduro et al, Molecular Cell, "Restriction of Mesendoderm to a Single Blastomere by the Combined Action of SKN-1 and a GSK-3BETA Homolog is Mediated by Med-1 and -2 in C. Elegans", 2001, vol. 7, No. 3, pp. 475-485.

McGrath et al, Developmental Biology, "Embryonic Expression and Function of the Chemokine SDF-1 and its Receptor, CXCR4", 1999, vol. 213, No. 2, pp. 442-456.

Robb et al., Developmental Dynamics, "Cloning, Expression Analysis, and Chromosomal Localization of Murine and Human Homologues of a Xenopus Mix Gene", 2000, vol. 219, No. 4, pp. 497-504.

Rodaway et al, Development, "Induction of the Mesendoderm in the Zebrafish Germ Ring by Yolk Cell-Derived TGF-B Family Signals and Discrimination of Mesoderm and Endoderm by FGF", 1999, vol. 126, No. 14, pp. 3067-3078.

Rodriguez et al, Developmental Biology, "Distinct Enhancer Elements Control Hex Expression During Gastrulation and Early Organogenesis", 2001, vol. 234, No. 2, pp. 304-316.

Shawlot et al, Nature, "Requirement for Lim 1 in Head-Organiser Function", 1995, vol. 374, No. 6521, pp. 425-430.

Smyth et al, Statistical Applications in Genetics and Molecular Biology, "Linear Models and Empirical Bayes Methods for Assessing Di Erential Expression in Microarray Experiments", 2004, vol. 3, No. 1, Pages Article 3.

Stavridis et al, Development, "A Discrete Period of FGF-Induced ERK1/2 Signalling is Required for Vertebrate Neural Specification", 2007, vol. 134, No. 16, pp. 2889-2894.

Sun et al, Genes & Development, "Targeted Disruption of FGF8 Causes Failure of Cell Migration in the Gastrulating Mouse Embryo", 1999, vol. 13, No. 14, pp. 1834-1846.

(56) References Cited

OTHER PUBLICATIONS

Thomas et al., Cold Spring Harbor Laboratory Press, "Axis Duplication and Anterior Identity in the Mouse Embryo", 1997, vol. 62, Number -, pp. 115-125.
Tada et al, Development, "Characterization of Mesendoderm: A Diverging Point of the Definitive Endoderm and Mesoderm in Embryonic Stem Cell Differentiation Culture", 2005, vol. 132, No. 19, pp. 4363-4374.
Tesar et al, Nature, "New Cell Lines From Mouse Epiblast Share Defining Features With Human Embryonic Stem Cells", 2007, vol. 448, Number , pp. 196-202.
Thomas et al, Current Biology, "Anterior Primitive Endoderm May Be Responsible for Patterning the Anterior Neural Plate in the Mouse Embryo", 1996, vol. 6, No. 11, pp. 1487-1496.
Thomas et al, Development, "Hex: A Homeobox Gene Revealing Peri-Implantation Asymmetry in the Mouse Embryo and an Early Transient Marker of Endothelial Cell Precursors", 1998, vol. 125, No. 1, pp. 85-94.
Vincent et al, Genes & Development, "Cell Fate Decisions Within the Mouse Organizer Are Governed by Graded Nodal Signals", 2003, vol. 17, No. 13, pp. 1646-1662.
Wells et al, Development, "Early Mouse Endoderm is Patterned by Soluble Factors From Adjacent Germ Layers", 2000, vol. 127, No. 8, pp. 1563-1572.
Yamaguchi et al, Genes& Development, "FGFR-1 is Required for Embryonic Growth and Mesodermal FGFR-1 is Required for Embryonic Growth and Mesodermal Patterning During Mouse Gastrulation", 1994, vol. 8, No. 24, pp. 3032-3044.
Yasunaga et al, Nature Biotechnology, "Induction and Monitoring of Definitive and Visceral Endoderm Differentiation of Mouse ES Cells", 2005, vol. 23, No. 12, pp. 1542-1550.
Ying et al, Cell, "BMP Induction of ID Proteins Suppresses Differentiation and Sustains Embryonic Stem Cell Self-Renewal in Collaboration With STAT3", 2003, vol. 115, No. 3, pp. 281-292.
Yusuf F et al, Anatomy and Embryology, "Expression of Chemokine Receptor CXCR4 During Chick Embryo Development", 2005, vol. 210, No. 1, pp. 35-41.
Zamparini et al, Development, "Hex Acts With -Catenin to Regulate Anteroposterior Patterning via a Groucho-Related Co-Repressor and Nodal", 2006, vol. 133, No. 11, pp. 3709-3722.
Mesnard et al, Development, "Nodal Specifies Embryonic Visceral Endoderm and Sustains Pluripotent Cells in the Epiblast Before Overt Axial Patterning", 2006, vol. 133, No. 13, pp. 2497-2505.
Mizoguchi et al, Developmental Biology, "FGF Signaling Negatively Regulates Nodal-Dependent Endoderm Induction in Zebrafish", 2006, vol. 300, No. 2, pp. 612-622.
Mohammadi et al, The EMBO Journal, "Crystal Structure of an Angiogenesis Inhibitor Bound to the FGF Receptor Tyrosine Kinase Domain", 1998, vol. 17, No. 20, pp. 5896-5904.
Morrison et al, Cell Stem Cell, "Anterior Definitive Endoderm From ESCS Reveals a Role for FGF Signaling", 2008, vol. 3, Number , pp. 402-415.
Nishikawa et al, Development, "Progressive Lineage Analysis by Cell Sorting and Culture Identifies FLK1+Vecadherin+ Cells at a Diverging Point of Endothelial and Hemopoietic Lineages", 1998, vol. 125, No. 9, pp. 1747-1757.
Norris et al, Development, "The FOXH1-Dependent Autoregulatory Enhancer Controls the Level of Nodal Signals in the Mouse Embryo", 2002, vol. 129, No. 14, pp. 3455-3468.
Offield et al, Development, "PDX-1 is Required for Pancreatic Outgrowth and Differentiation of the Rostral Duodenum", 1996, vol. 122, No. 3, pp. 983-995.
Okabayashiy et al, Current Opinion in Genetics & Development, "Tissue Generation From Amphibian Animal CAPS", 2003, vol. 13, No. 5, pp. 502-507.
Perea-gomez et al, Development, "HNF3B and LIM1 Interact in the Visceral Endoderm to Regulate Primititve Streak Formation and Anterior-Posterior Polarity in the Mouse Embryo", 1999, vol. 126, No. 20, Pages.
Poulain et al, Development, "Zebrafish Endoderm Formation Is Regulated by Combinatorial Nodal, FGF and BMP Signalling", 2006, vol. 133, No. 11, pp. 2189-2200.
Stem Cells: Scientific Progress and Future Research Directions, Department of Health and Human Services, Journal: National Institute of health,Year:Jun. 2001, pp. 1-4.
Jaenish Rudolf et al. ,Stem Cells, the Molecular Circuitry of Pluripotency and Nuclear Reprogramming, Journal :Cell, Year Feb. 22, 2008, vol. 132, pp. 567-582.
Mclin, V et al. "Repression of Wnt/beta-catenin signaling in the anterior pancreas development" Development vol. 134 (12): 2207-2217 (2007).
Micallef, S et al. "Retinoic acid induces Pdx1-positive endoderm in differentiating mouse embryonic stem cells" Diabetes vol. 54(2): 301-305 (2005).
Jiang Wei et al. "In vitro derivation of functional insulin-producing cells from human embryonic stem cells" Cell Reseach vol. 17(4): 333-344 (2007).
Chen, et al. "Self-renewal of embryonic stem cells by a small molecule" Proceedings of the National Academy of Sciences USA vol. 103(46): 17266-17271 (2006).

* cited by examiner

REGIONALISED ENDODERM CELLS AND USES THEREOF

CROSS-REFERENCE TO RELATED APPLICATIONS

This application is a National Stage application of PCT/GB2008/002875, filed Aug. 25, 2008, which claims the benefit and priority of United Kingdom Patent Application No. 0716515.2, filed Aug. 24, 2007 and United Kingdom Patent Application No. 0809852.7, filed May 30, 2008. The foregoing applications are incorporated by reference herein in their entirety.

The instant application contains a Sequence Listing which has been submitted in ASCII format via EFS-WEB and is hereby incorporated by reference in its entirety. Said ASCII copy, created on Dec. 15, 2011, is named sequence.txt and is 8 KB.

FIELD OF THE INVENTION

The present invention relates to the generation of anterior definitive endoderm (ADE) cells from embryonic stem cells and the differentiation of such cells to, for example, pancreatic or liver cells. The invention also relates to cell lines, cell culture methods, cell markers and the like and their potential uses in a variety of applications.

BACKGROUND TO THE INVENTION

Embryonic stem (ES) cells hold tremendous promise as a source of functional differentiated cell types for regenerative medicine. In addition, ES have great potential as an in vitro system for the study of developmental biology, allowing the effective isolation of distinct populations of cells that normal exist very close together in both space and time during embryonic development. Both the efficient directed differentiation of ES cells to specific lineages and studies of developmental mechanism require the in vitro recapitulation of the appropriate intermediate cell types formed in embryonic development. Thus, the successful differentiation of ES cells to neural, haematopoetic and epidermal cell types involve a progression through intermediate progenitor states prior to terminal differentiation (Bagutti et al. 1996; Nishikawa et al. 1998; Conti et al. 2005) [Conti 2005, Nishikawa 1998, Bagutti 1996]. It is likely that successful differentiation of endodermal lineages from ES cells will also depend on efficiently recapitulating the step-wise progression that occurs during normal embryogenesis.

The anterior definitive endoderm (ADE) is one of the first defined lineages to emerge from the primitive streak during gastrulation. It originates in the node, the mammalian equivalent of the Spemman Organiser (also referred to as axial mesenderm) and these cells migrate anteriorly during embryogenesis and have an important role in patterning the anterior neural axis (Lu et al. 2001). Later during gut tube formation they migrate ventrally to form the ventral foregut, a unique population of bipotent precursors of the liver and pancreas(Deutsch et al. 2001). Thus the ADE not only represents an essential signalling centre for embryogenesis, but an important intermediate in the production of liver and pancreas.

In vertebrate developmental contexts mesendoderm is often used to refer to the derivatives of the node or Spemman Organiser (here referred to as axial mesendoderm), structures that can be associated with both the mesoderm and endoderm. However, mesendoderm can also be used to refer globally to the migrating lineages at gastrulation, mesoderm and endoderm. These lineages may have evolved from a common ancestor and are induced by the same signalling pathways (Rodaway and Patient 2001), suggesting that in some instances the mesoderm and endoderm may develop from a common precursor population during embryonic development. In *C.elegans*, sea urchin and zebrafish, individual progenitor cells have been shown to be capable of differentiating into both mesoderm and endoderm have been identified (Rodaway et al. 1999; Angerer and Angerer 2000; Maduro et al. 2001; Davidson et al. 2002). In mouse, recent data from in vitro differentiation of ES cells provides evidence for the existence of a bi-potential mesendodermal cell in culture (Tada et al. 2005), however, whether individual epiblast derived mesendodermal progenitor exists in mouse in vivo remains to be demonstrated.

Loss of function studies in the mouse suggest that mesendoderm induction is dependent on nodal related TGF-β and canonical Wnt signalling, with the ADE being most sensitive to a reduction in the activity of these pathways (Vincent et al. 2003). This is consistent with experiments in lower vertebrates and implies that the highest activity of these two pathways is required to induce the most anterior endoderm (Green and Smith 1990; Dyson and Gurdon 1998; Chen and Schier 2001; Vincent et al. 2003). However, the identity of mesendodermal cell populations in the embryo is intricately linked to the migration of these cells during gastrulation. Thus, perturbation of these signalling pathways in the embryo may disrupt cell movements and produce a phenotype in the mesendoderm, without being directly involved in mesendoderm induction. Studying the induction of endoderm using an in vitro cell system would avoid this complication.

Several recent studies have described the generation of mesendodermal cell populations in vitro from ES cells as a starting point for the production of definitive endoderm and ventral foregut derivatives (Kubo et al. 2004; Tada et al. 2005; Yasunaga et al. 2005; D'Amour et al. 2006; Gadue et al. 2006). In mouse this work has relied on the use reporter cell lines that contain a marker under the control of a mesendodermal promoter. However, these reporter lines have been designed to identify mesendoderm precursors or all axial mesendoderm derivatives and cannot identify positionally specified populations such as the ADE. Without enrichment for ADE, the efficiency of generating foregut derivatives will be reduced. The inability to enrich for regionally specified axial mesendoderm also limits the usefulness of ES cells as an experimental system to address mechanisms of lineage specification in vitro.

It is desired to be able to provide ADE cells and then differentiate these cells into other cells, such as pancreatic and liver cells, but this is hitherto not possible in significant numbers. It is also desired to provide differentiated cells such as pancreatic or liver cells for transplantation but the persistence of ES and other non-pancreatic/non-liver cells in ES-derived cell populations can give rise to tumours in recipient animals.

A complete understanding of the molecular and cellular events controlling the behaviour of ADE cells is essential, not only as a route for understanding embryogenesis, but also as a framework upon which ADE cells can be isolated, expanded and controlled for future therapeutic and research applications. It is desirable to develop methods and conditions for culturing large quantities of ADE cells that allow the cells to be differentiated into, for example, pancreatic or liver cells. It is particularly desirable to have defined culture media, which enable this as the use of defined media is highly desirable in a clinical or research setting.

The present invention seeks to solve one or more of the above described disadvantages.

It is an object of the present invention to circumvent one or more of these problems by attempting to purify populations enriched for ADE and use these as a source of material for further differentiation.

SUMMARY OF THE INVENTION

The failure of ES differentiation protocols to efficiently generate functional liver and pancreatic cells may be due to a failure to enrich for the appropriate developmental intermediate, anterior definitive endoderm (ADE). Described herein is the first demonstration that defined ADE can be produced, purified and expanded from ES cells. Thus purified or subcultured ES cell-derived ADE can be used as a platform for differentiation toward liver and pancreatic progenitors. Furthermore our ability to deconstruct ADE specification in vitro revealed an unsuspected requirement for FGF signalling that had been obscured because of this pathways role regulating gastrulation movements in vivo.

The present invention is based on a novel strategy to isolate ADE from ES cells by detecting Hex expression in conjunction with the cell surface marker CXCR4. CXCR4 is expressed in the embryonic definitive endoderm but not anterior visceral endoderm (AVE) and thus, when coupled to Hex, defines prospective ADE. Hex is a homeobox transcriptional repressor that is one of the earliest markers of ADE and has also been shown to suppress more posterior, pan-mesodermal identities(Thomas et al. 1998; Brickman et al. 2000; Zamparini et al. 2006). Unlike a number of the marker genes previously employed, Hex is neither a marker of the earlier transient mesendoderm cell population (Brachyury (Kubo et al. 2004), Goosecoid (Tada et al. 2005), of all axial mesendoderm (Foxa2 (Gadue et al. 2006)) or of all endoderm at particular time points (Sox17 (Yasunaga et al. 2005)). In addition to its expression in the ADE, Hex is expressed in the extra-embryonic visceral endoderm, in an early patterning centre known as the anterior visceral endoderm (AVE) (Thomas et al. 1998). It is not hitherto been suggested that the detection of Hex and CXCR4 expression could be used as a marker of ADE cell generation.

The inventors show that significant numbers of cells in differentiating ES cell cultures can be induced to express Hex and CXCR4 and present extensive expression analysis of these in vitro derived populations allowing further ADE markers to be identified. They further disclose culture conditions and present a serum free cell culture regime for the differentiation of ES cells towards ADE.

Thus, in a first aspect there is provided a method of identifying anterior definitive endoderm (ADE) cells derived from a population of ES cells, said method comprising the step of detecting two or more ADE cell markers, in a cell population derived from said ES cell population, in order to identify said ADE cells. In accordance with one embodiment of the present invention, the method of identifying ADE comprises the step of detecting expression of Hex and CXCR4, in a cell population derived from said ES cell population, in order to identify said ADE cells. However, following identification of further markers and in particular cell surface markers other combinations of makers can be used to identify and/or isolate ADE cells. ADE markers which have been identified by the inventors include. Sst, Pyy, Ghrl, Slc38a5, Chga, Exph5, Tmprss2, Clic6, 1110003E01Rik, Sstr2, 4732456N10Rik, Rab15, Rnase4, Slc6a4, Fxyd3, Slc12a2, 1700027A23Rik, Tm4sf2, 0610040B21Rik (aka txndcl2), Apoa1, 2410021P16Rik (aka acad10), 4832420M10, Fzd5, Gckr, Enpp5, Syt5, Cklfsf8 (aka Cmtm8), Robo1, Ctsh, Rarres1, Sec1412, Ripk4, Slc7a8, Ng23, Krt2-7, Sfrp5, Pga5, foxa1, foxa2, foxa3, Cer1, Hhex, Otx2, Gatn3 and Cxcr4

Preferred cell surface markers which have been identified and may be used to identified and/or isolate ADE cells include Sic38a5, Tmprss2, Clic6, Sstr2, Sic6a4, Fxyd3, Sic12a2, Tm4sf2, Fzd5, Cklfsf8 (aka Cmtm8), Rarres1, Sic7a8, Sfrp5 and Cxcr4.

Using methods described herein, the present inventors have been able to generate cell populations comprising greater than 5%, 10%, 15%, 20%, 30% or 40% ADE cells from a cell population substantially initially consisting essentially of ES cells.

Thus, in a further aspect there is provided a mixed cell population obtained directly from an ES cell culture, said mixed cell population comprising at least 5%, 10%, 15%, 20%, 30% or 40% ADE cells. The ADE cells in said mixed population may be subsequently enriched or purified in order to provide substantially pure ADE cell populations.

In a further aspect, there is provided a substantially pure population of ADE cells which i) will proliferate in an in vitro culture without further differentiation for at least 8 passages and/or over 2 months; and ii) maintains the potential to differentiate into derivatives of ADE cells. Conveniently, the cell line comprises cells which are not genetically modified.

Following enrichment/purification of the ADE cells from the mixed population of cells by cell sorting techniques, e.g. flow cytometry, well known to those skilled in the art, the present inventors were able to further differentiate the ADE cells into cells of pancreatic or liver lineage, using appropriate differentiating factors. The inventors were able to generate a differentiated cell culture from a cell culture comprising ADE cells obtained using the methods described herein in which >40%, such or 50%, 60%, 70% or even 80% or 90% of the cells differentiated in the cell culture were pancreatic cells, or separately, in which >10%, such as 15% or 20%, 30%, 40%, 50% or 60% were liver cells. Such cell populations can be essentially free of ES cells and/or other progenitor cells, such as mesendoderm progenitor cells.

In preferred embodiments, cells are cultured in the absence of serum, e.g. in medium that is free of serum and/or free of serum extract. It is preferred in some embodiments that cells are cultured attached to a substrate, otherwise referred to as in an adherent culture.

The invention further provides methods of obtaining ADE cells or cells differentiated therefrom, and specifically as set out in the protocols herein, and additionally provides cells obtained by such methods.

ADE cells of the invention and cells derived therefrom can be derived from, inter alia, humans, primates, rodents and birds. Preferably, the ADE cells are derived from mammals, especially mice, rats and humans. ES cells from which the ADE cells are derived may be either wild-type or genetically modified ES cells.

Embryonic stem cells have been reported from a number of mammalian sources include mouse (Bradley et at (1984) Nature 309: 255-56), human (Thomson et al (1998), Science 202, p 1145-1147), American mink (Mol Reprod Dev (1992) December; 33(4): 418-31), pig and sheep (J Reprod Fertil Suppl (1991); 43: 255-60), hamster (Dev Biol (1988) May; 127(1): 224-7) and cow (Roux Arch Dev Biol (1992); 201: 1340141). Specific examples herein use mouse and ES cells. It will be appreciated that the methods and compositions of the present invention are suitable for adaptation to culturing of other mammalian pluripotent cell cultures, thus including primate, especially human, rodent, especially mouse and rat, and avian pluripotent stem cells, especially ES cells.

The present inventors have generated a genetically modified mouse ES cell line which may be of use in the present invention. The mouse ES cell line comprises a nucleic acid construct comprising a marker gene which has been inserted within the Hex locus such that the marker gene is under control of the Hex promoter. The marker gene is preferably inserted into the first exon of the Hex locus by homologous recombination. A suitable marker is the RedStar (RS) marker gene and this may be introduced by use of an appropriate selection cassette which may be excised from the genome following marker gene insertion. This may be achieved for example using the Cre-LoxP system, or the Flp recombinase system, or other recombinase system.

Suitable ES cells may be used to generate a $Hex^{RS}$ mouse cell line which is heterozygous for the RS gene. Thus, the present inventors also provide a $Hex^{marker\ gene/+}$ embryo or a mouse especially a $Hex^{RS/+}$ embryo or a mouse for use in obtaining ADE cells.

By using ES cells derived by using the above described mouse, the present inventors were able to obtain ADE cells by detecting for $Hex^{RS}$ expression and CXCR4 expression. However, the skilled addressee can easily adapt this, using homologous genes, such that the technique can be carried out in order to obtain ADE cells from other organisms, especially other mammals including human.

The cells of the present invention, whether grown in suspension or as adherent cell cultures, are grown in contact with culture media.

Culture media used in the present invention preferably comprise a basal medium, optionally supplemented with additional components.

Basal medium is a medium that supplies essential sources of carbon and/or vitamins and/or minerals for ES cells. The basal medium is generally free of protein and incapable on its own of supporting self-renewal/symmetrical division of ES cells. Examples of such media include GMEM, and DMEM.

In certain embodiments, culture media used in the invention do not contain any components which are undefined (e.g. serum and/or feeder cells), that is to say components whose content is unknown or which may contain undefined or varying factors that are unspecified. An advantage of using fully defined media, free of serum and free of serum extracts, is that efficient and consistent protocols for culture and subsequent manipulation of ADE cells and cells derived therefrom can be obtained.

Typical substrates for culture of the cells in all aspects of the invention are culture surfaces recognized in this field as useful for cell culture, and these include surfaces of plastics, metal, composites, though commonly a surface such as a plastic tissue culture plate, widely commercially available, is used. Such plates are often a few centimeters in diameter. For scale up, this type of plate can be used at much larger diameters and many repeat plate units used.

The culture surface may further comprise a cell adhesion protein, usually coated onto the surface. Receptors or other molecules present on the stem cells bind to the protein or other cell culture substrate and this promotes adhesion to the surface and promotes growth. Gelatin coated plates are particularly preferred.

In certain embodiments, the cultures of the invention are preferably adherent cultures, i.e. the cells are attached to a substrate.

Methods of the invention can be used for stimulating differentiation of ES cells to ADE cells in medium which is free of serum and free of serum extract. Preferably, such methods are also carried out in the absence of feeder cells and/or feeder cell extracts.

For example, differentiation of ES cells to ADE cells can be carried out comprising the steps of:

maintaining ES cells in a first culture medium for a period of time, optionally on feeders, in the presence of serum or an extract of serum or in a serum free/serum extract free medium;

replacing the first medium with a second serum free medium comprising activin or removing the serum or the serum extract from the first medium and withdrawing the feeders (if present) and adding activin, so that the first medium is free of feeders, serum and serum extract; and subsequently propogating the ES cells in the medium comprising activin in order to obtain cells comprising ADE cells, with the proviso that the first and second medium are not SF03 medium.

SF03 medium has been described previously by Tada et al 2005 and is available from Iwai Chemicals Company, Japan.

Suitable culture media includes GMEM, DMEM, F12 and N2B27. N2B27 is preferred and is available from Invitrogen, Paisley, UK.

Further agents may be included in the first or second medium such as EGF and/or an agonist of a receptor of the TGF-β superfamily.

An agonist of a receptor of the TGF-β superfamily is suitably a member of the TGF-β superfamily of signalling factors, and is preferably a bone morphogenetic protein (BMP) such as BMP-4. Known homologues of BMP4, such as BMP2 and BMP7, may also be suitable, as are homologues from non-mammalian species such as decapentaplegic (dpp) from *Drosophila melanogaster*. The term "agonist" is also intended to embrace mimetics, fusion proteins or chimaeras of TGF-β superfamily signalling polypeptides, and fragments, variants and derivatives thereof, capable of activating receptors of the TGF-β superfamily.

For cells grown in suspension a preferred protocol comprises maintaining cells in a medium comprising serum such as, fetal calf serum, following by maintaining the cells in a serum free medium comprising activin in order to obtain ADE cells. Typically, the cells are grown in serum comprising medium for 1-3 days, e.g. 2 days followed by culture in serum free medium for 3-6 days such as 5 days.

Preferably the medium comprising serum is GMEM. Preferably the medium comprising activin is N2B27.

Preferably the initial cell density in medium containing serum or serum extract is less than $1\times10^5$ cells/ml, typically between $1\times10^3$ cells/ml to $7\times10^4$ cells/ml, such as $3\times10^3$ cells/ml to $5\times10^4$ cells/ml especially $5\times10^3$ cells/ml.

For cells grown in serum free solution, the cells may be grown as adherent monolayer cultures, or may be allowed to form embryoid bodies in suspension.

Cells grown in monolayer may initially be grown for 1-3 days, e.g. 2 days in a first medium which may comprise one or more of activin, Fgf4, Bmp4 or CHIR99021. Thereafter, the cells may be grown for 3-6 days e.g. 5 days, in a second medium supplemented with activin and further optionally comprising EGF and/or Fgf4.

Preferably the first medium comprises activin and Bmp4 and optionally Fgf4. Preferably the second medium comprises EGF and optionally Fgf4. Preferably the first medium is N2B7. Preferably the second medium is SF03.

Cells grown in serum free solution and which are allowed to form embroid bodies may be initially grown for 1-3 days such as 2 days in a medium which may optionally comprise activin and may further comprise Bmp4. A preferred medium is N2B27. Thereafter cells may be grown for 3-6 days especially 5 days in a second medium comprising activin and preferably further comprising Egf4, and optionally Bmp4 and/or GI. Preferably the first medium is N2B7. Preferably the second medium is SF03.

Using appropriate cell sorting techniques to detect Hex and CXCR 4 expression, the present inventors have been able to further purify the ADE cells obtained, in order to obtain ADE cells substantially free of other cells, such as ES cells.

Such ADE cells have been observed to display a number of genes which can serve as unique markers of ADE cells or may be used to reprogramme cells using iPS techniques known in the art. The genes which have been observed to be upregulated in ADE cells may therefore be of use as unique ADE cell markers or used to generate ADE cells are Sst, Pyy, Ghrl, Slc38a5, Chga, Exph5, Tmprss2, Clic6, 1110003E01Rik, Sstr2, 4732456N10Rik, Rab15, Rnase4, Slc6a4, Fxyd3, Slc12a2, 1700027A23Rik, Tm4sf2, 0610040B21Rik (aka txndcl2), Apoa1, 2410021P16Rik (aka acad10), 4832420M10, Fzd5, Gckr, Enpp5, Syt5, Cklfsf8 (aka Cmtm8), Robo1, Ctsh, Rarres1, Sec1412, Ripk4, Slc7a8, Ng23, Krt2-7, Sfrp5, Pga5, foxa1, foxa2, foxa3, Cer1, Hhex, Otx2, Gatn3 and Cxcr4. Desirably at least 2, 3, 4, 5, 10, 15 or 20 of these genes may be used to identify/generate such ADE cells.

In order to facilitate purification of ADE cells from mixed populations of cells, proteins, from the list above, which are cell surface expressed, may be used to identify and/or purify ADE cells. The genes/proteins which are cell surface expressed include Slc38a5, Tmprss2, Clic6, Sstr2, Slc6a4, Fxyd3, Slc12a2, Tm4sf2, Fzd5, Cklfsf8 (aka Cmtm8), Rarres1, Slc7a8, Sfrp5 and Cxcr4The ADE cells may be identified an/or purify using such cell surface expressed proteins using, for example, protein specific antibodies, using techniques well known to those of skill in the art.

The ADE cells of the present invention may be allowed to differentiate and the present inventors have been able to obtain, through use of appropriate differentiation factors, pancreatic and liver cells.

There is much interest in the use of pancreatic cells and liver cells in the treatment of pancreatic and liver diseases; in particular in the treatment of diseases such as diabetes, hepatitis and cirrhosis. The methods, compositions, cell populations, cell lines and single cells of the present invention are all capable of being used in such treatment, as well as in the manufacture of preparations for such treatment.

In a further aspect, therefore, the invention provides for the use of cell lines, cell populations, single cells and compositions described above for cell therapy and for the manufacture of a preparation for the treatment of pancreatic and liver disease and injury. Such preparations may be formulated in phosphate buffered saline (PBS).

Methods of treatment of the diseases listed above can comprise the transplantation of single cells, cell lines, compositions, or cell populations of the invention into a patient. Preferably, the patient is mammalian, more preferably the patient is human.

The cells of the invention, and in particular the cell lines, can be used to assay the effective of inductive or blocking factors on the differentiation of ADE cells. Such an assay may comprise contacting an ADE cell of the invention (i.e. as present in the compositions, cell lines, and populations, or a single ADE cell) with the factor to be tested. The effect of the factor on the differentiation of the ADE cell can be suitably assessed by determining the marker profile of the resultant cells, i.e. to show whether the cells have a similar marker profile to the cells of the invention, or whether these markers have been lost. The cells of the invention are also suitable for assaying pharmaceuticals for, for example, the treatment of pancreatic or liver disease.

Examples Section

The present invention will now be further described by way of Example and with reference to the following figures which show:

Analysis of day 7 differentiated cells by flow cytometry. Cells were cultured in serum containing media for 2 days followed by 5 days in N2B27 plus activin and EGF. The percentage of H+C+ cells induced after 7 days varied between 11.4 and 22.0.

Figure 4:
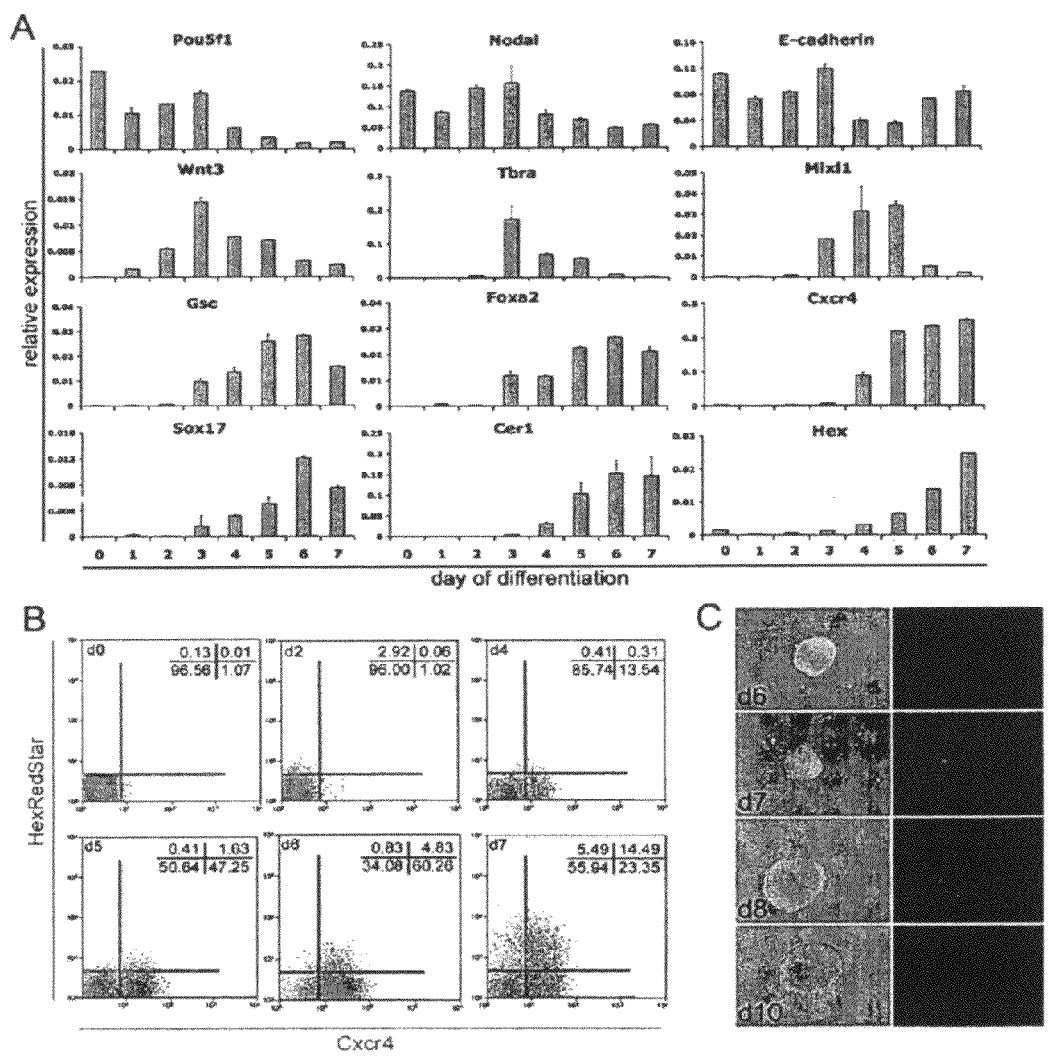

FIG. 4 shows In vitro differentiating cell cultures produce a gene expression dynamic similar to that observed during ADE induction in vivo. (A) Analysis of gene expression from day 0 to day 7 of differentiation by quantitative real-time RT-PCR. The x axis represents the time in days at which the RNA was collected (timepoint 0=ES cells) and the y axis represents relative expression calculated by normalising the transcript number by the b-actin transcript number. The relative expression value represents the mean of 2 experimental replicates. Error bars represent the standard deviation. (B) Analysis of RS and CXCR4 expression by flow cytometry from day 0 to day 7 of differentiation. The percentage of the four cell fractions are indicated. (C) RS expression in differentiating cell aggregates. RS expression was first detected by fluorescent microscopy at day 6, peaked at day 7-8 and was undetectable by day 10.

Figure 5:
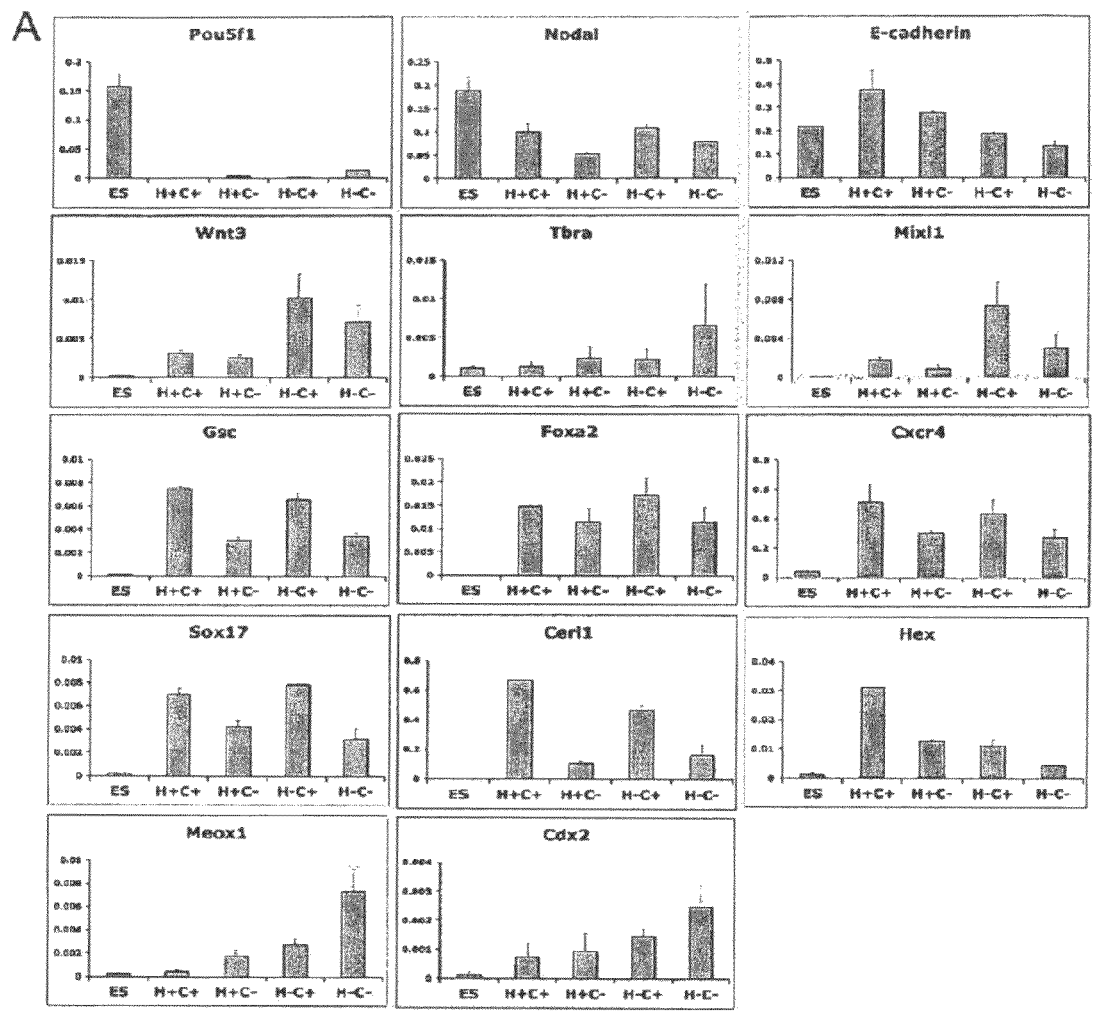
Figure 5:
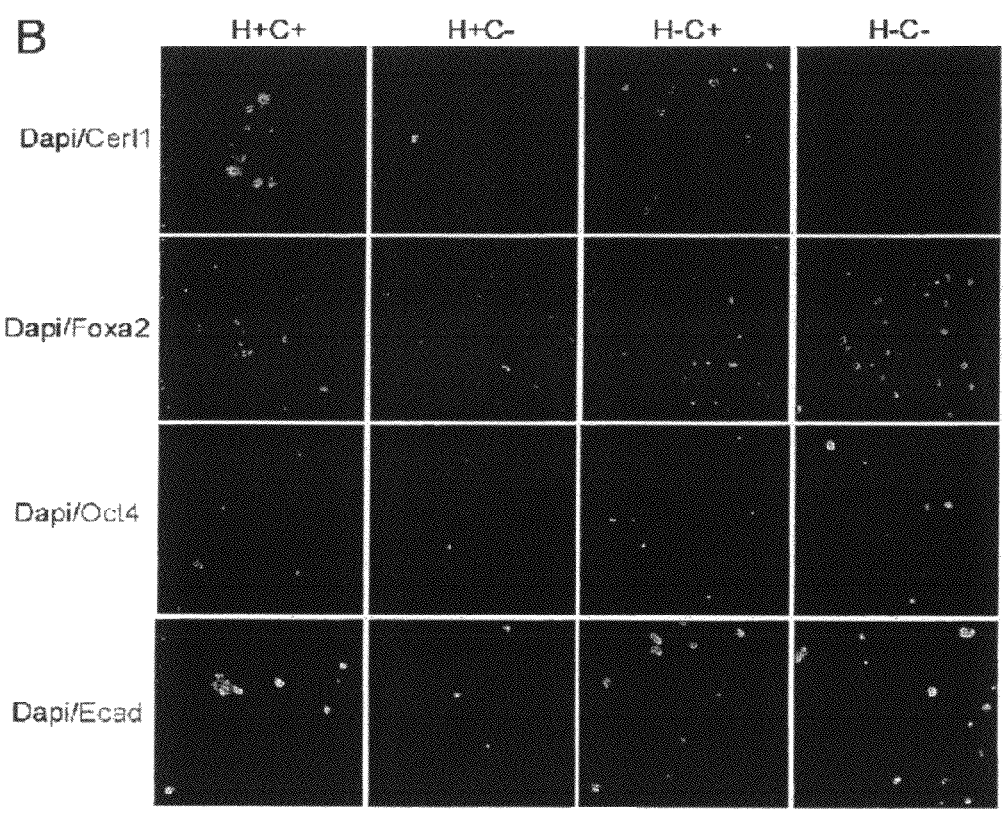

FIG. 5 shows Hex and CXCR4 marks the emerging ADE cell population. (A) Quantitative real-time RT-PCR. RNA was prepared from the four cell fractions sorted by flow cytometry following 7 days of differentiation. The differentiation conditions were as described in FIG. 4. The y axis represents relative expression calculated by normalising the transcript number to the b-actin transcript number. Values represent the mean relative expression value from 2 independent experiments. Error bars represent standard deviations. (B) Immunocytochemistry on ADE differentiated cells. The four cell fractions were sorted by flow cytometry following 7 days of differentiation as described in FIG. 4. Cells were immunostained by anti-Cer11, anti-Foxa2, anti-Oct4 and anti-Ecad. Nuclei were stained with DAPI. Green Cer1, Oct4 and Ecad positive cells were detected using an Alexa-488 secondary antibody and red Foxa2 positive cells were detected using an Alexa-568 secondary antibody.

Figure 6:
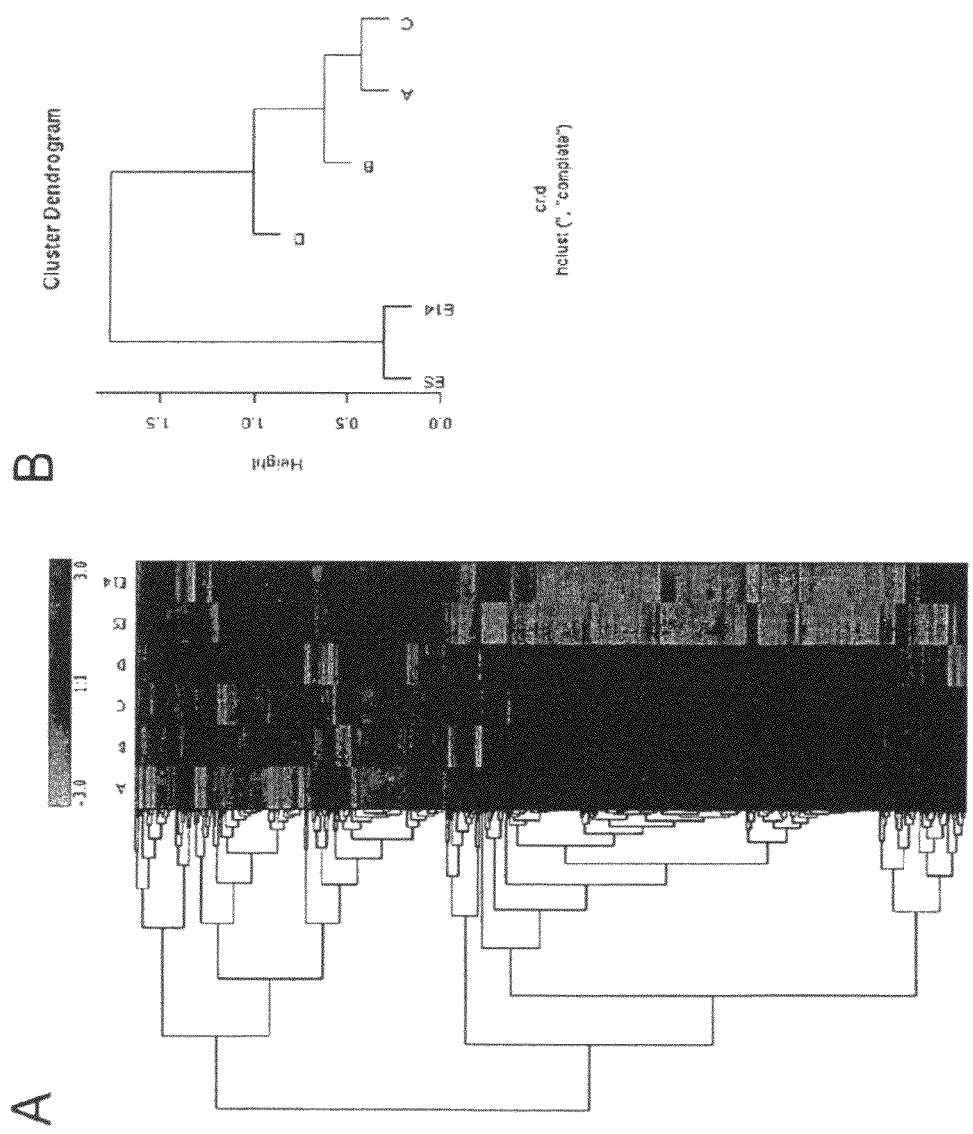
Figure 6:
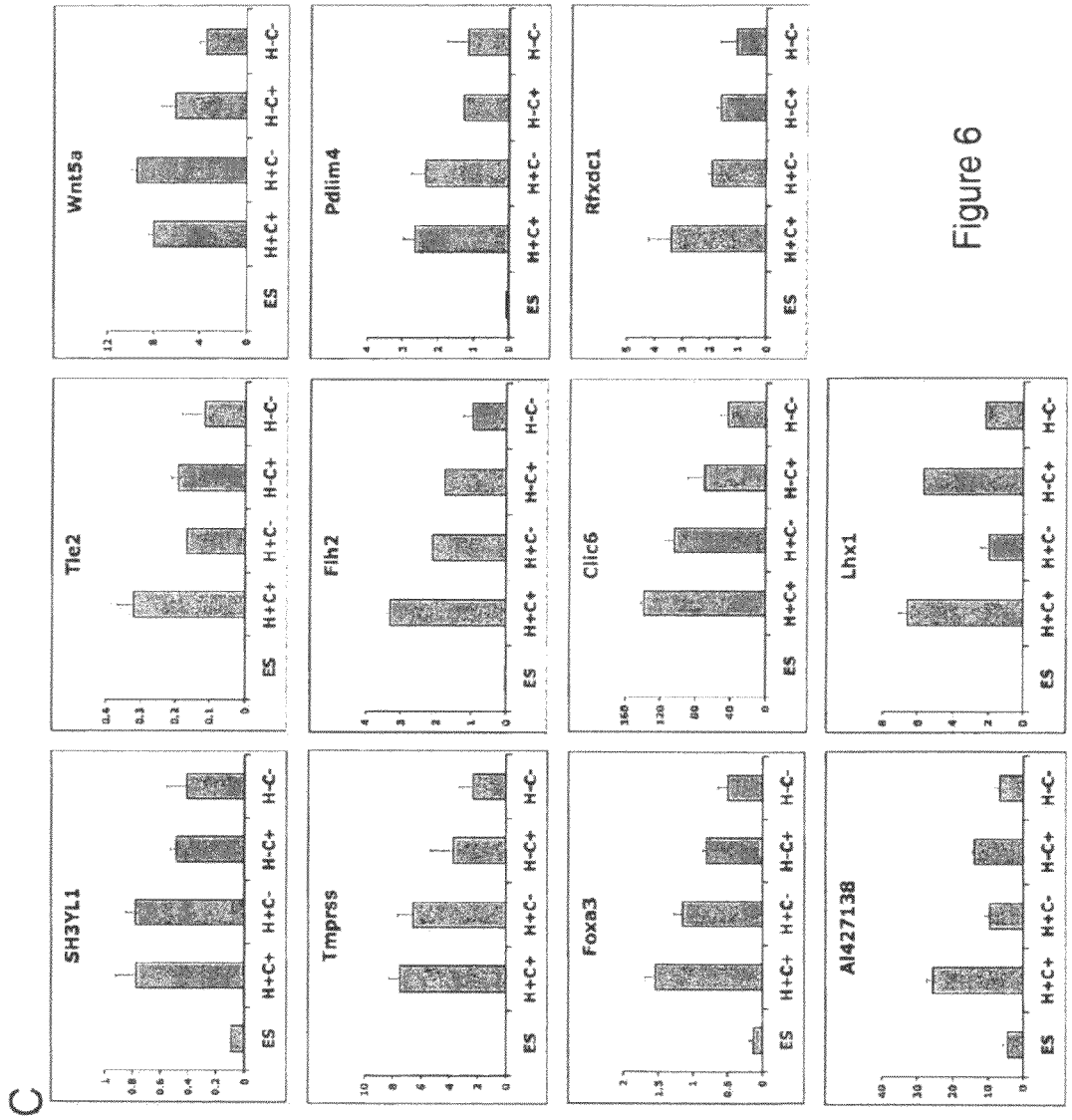

FIG. 6 shows Gene expression profiling of RS and CXCR4 cell populations.
(A) Heat map. (B) Cluster dendrogram (C) Quantitative real-time RT-PCR of genes differentially expressed in the micorarray analysis. RNA was prepared from the four cell fractions sorted by flow cytometry following 7 days of differentiation. The differentiation conditions were as described in FIG. 4. The y axis represents relative expression calculated by normalising the transcript number to the Tata box-binding protein (TBP) transcript number. Values represent the mean relative expression value from 3 independent experiments. Error bars represent standard deviations.

Figure 7:
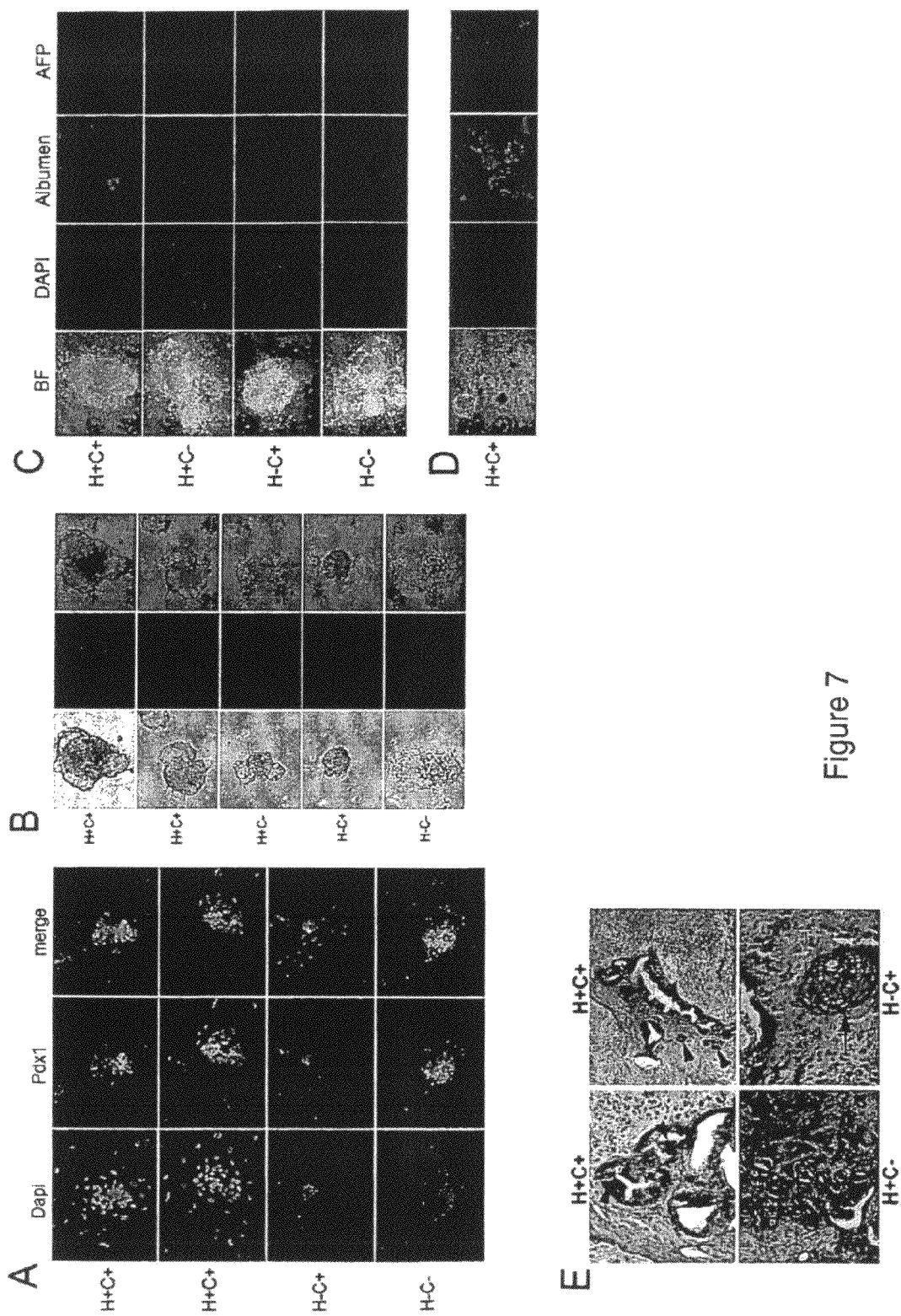

FIG. 7 shows ADE cell cultures can be further differentiated towards mature endodermal lineages in vitro and in vivo. (A) Induction of pancreatic progenitors. Day 7 ADE cultures were sorted into 4 cell fractions and plated in pancreatic progenitor inducing conditions for 5 days. Cells were immunostained with anti-Pdx1 and nuclei stained with DAPI. Pdx1 positive cells were detected using an Alexa-488 secondary antibody and shown in green. All clusters of Pdx staining were similar for each condition. We obtained 9 from H+C+ cultures, 4 from H−C+ cultures and 1 from H−C− cultures. (B) Induction of hepatocytes. Day 7 ADE cultures were sorted into 4 cell fractions and plated into hepatocyte inducing conditions as aggregates for 2 days. At this timepoint RS protein was only observed in the H+C+ and H+C− cell aggregates. (C) 2 day hepatocyte cell aggregates were plated on gelatin for a further 3 days. Cells were immunostained with anti-albumen, anti-AFP and nuclei stained with DAPI. Green albumen positive cells were detected using an Alexa-488 secondary antibody and red AFP positive cells were detected using an Alexa-568 secondary antibody. A few albumen positive cells were observed in the H+C+ and H+C− samples and these samples contained the highest percentage of AFP positive cells. (D) By day 13 of the hepatocyte culture (day 20 of the total culture period) many albumen positive cells were present in the H+C+ cultures. (E) Analysis of sorted cell populations in kidney capsule explants. Hematoxylin and Eosin and PAS staining of sections from the four sorted cell fractions. Gut-like epithelial structures containing PAS positive secretory granules (deep red, black arrowheads) were present in H+C+ and H+C− growths. Cartilage (black arrow) was observed in the H−C+ growths.

Figure 8:
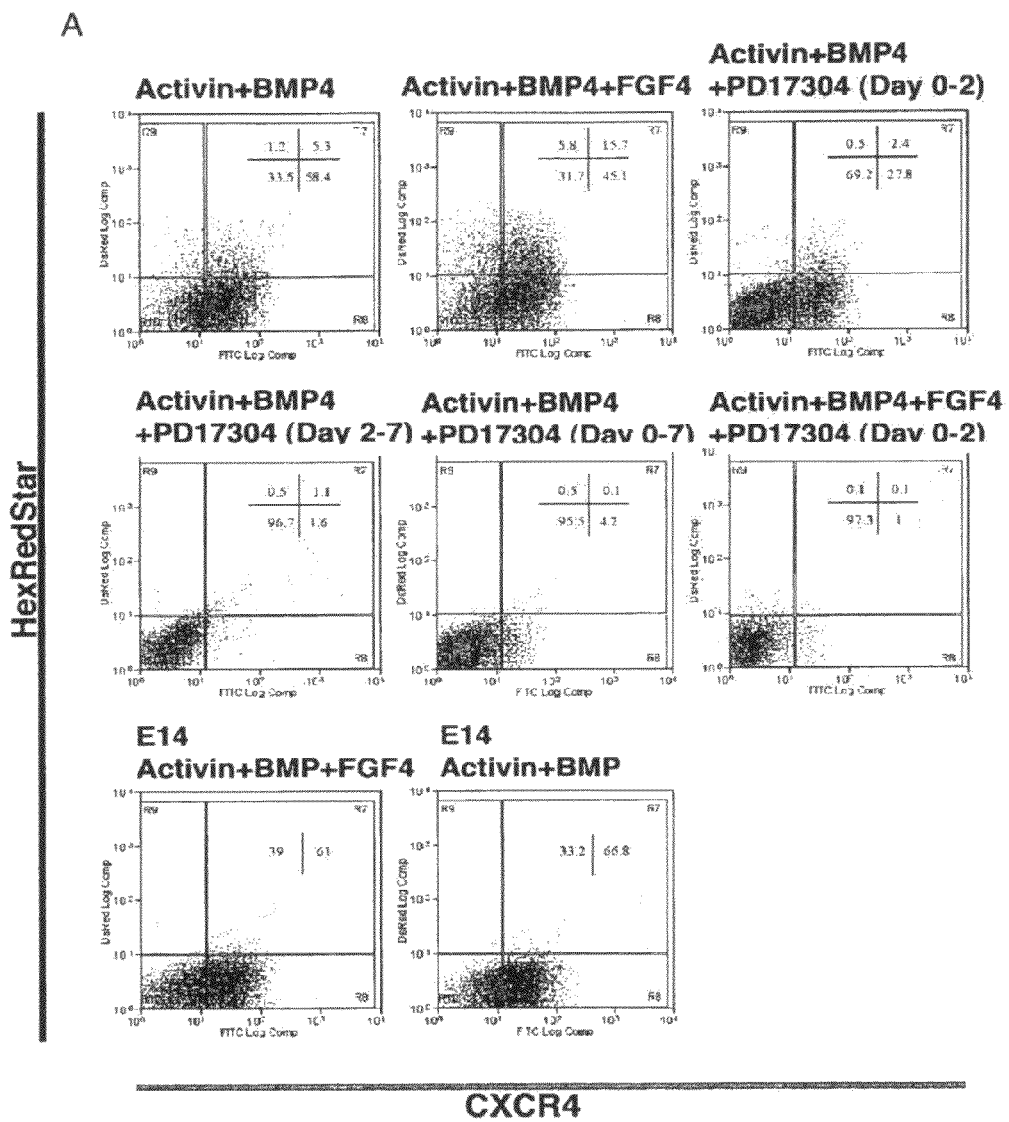
Figure 8:
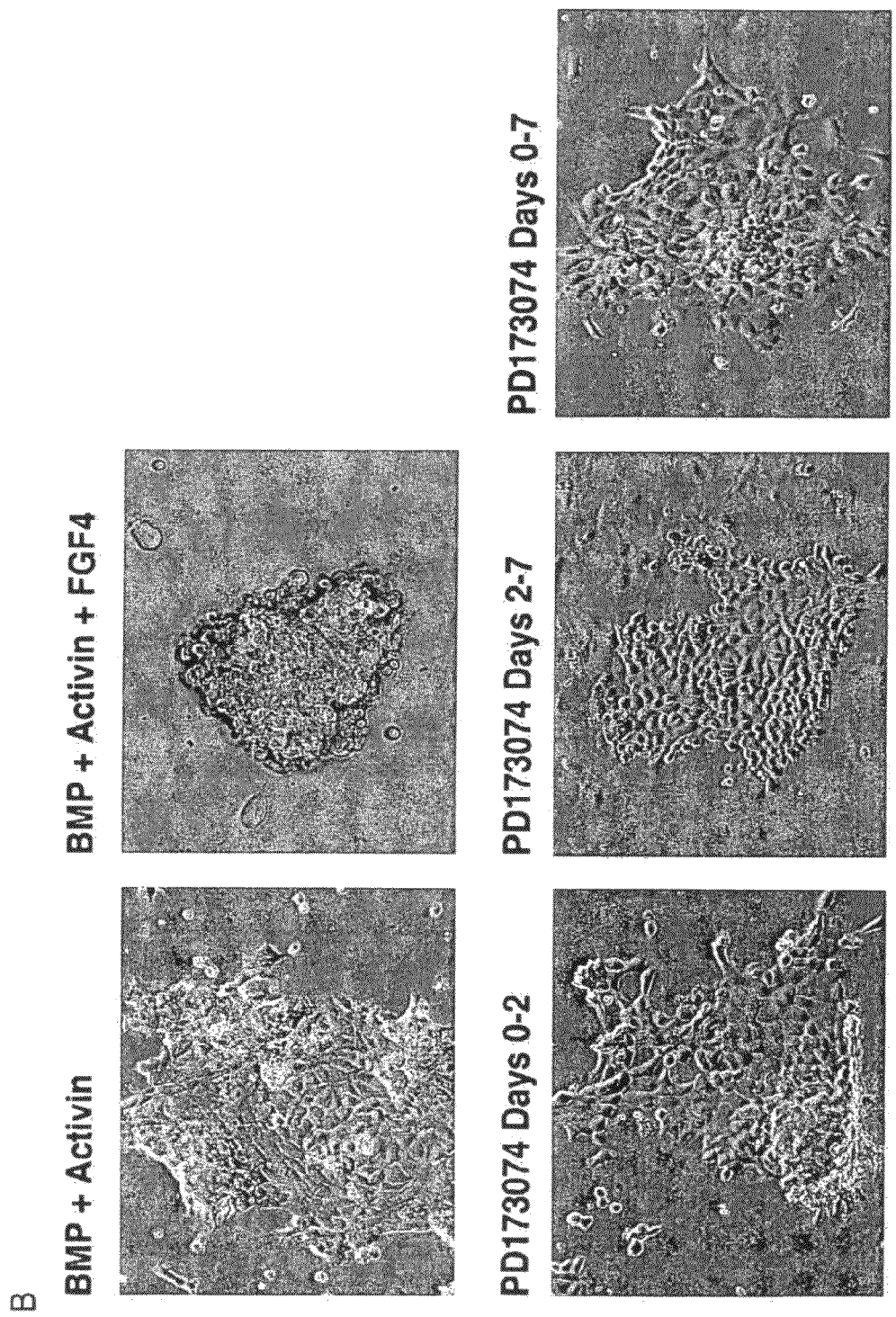

FIG. 8 shows Defining the requirements for ADE induction in chemically defined serum-free culture conditions reveals a novel requirement for FGF signalling. (A) Flow cytometry showing the proportion of H+C+ cells induced under a series of conditions. All differentiation was done in N2B27 for two days, followed by five days in SF03. The minimum set of cytokines is indicated on top of each panel. The presence or absence of the FGF antagonist, PD173074 is indicated. (B) Fluorescence images of cell morphology. Cells were cultured with indicated cytokines or the FGF receptor antagonist, PD 173074.

Figure 9:
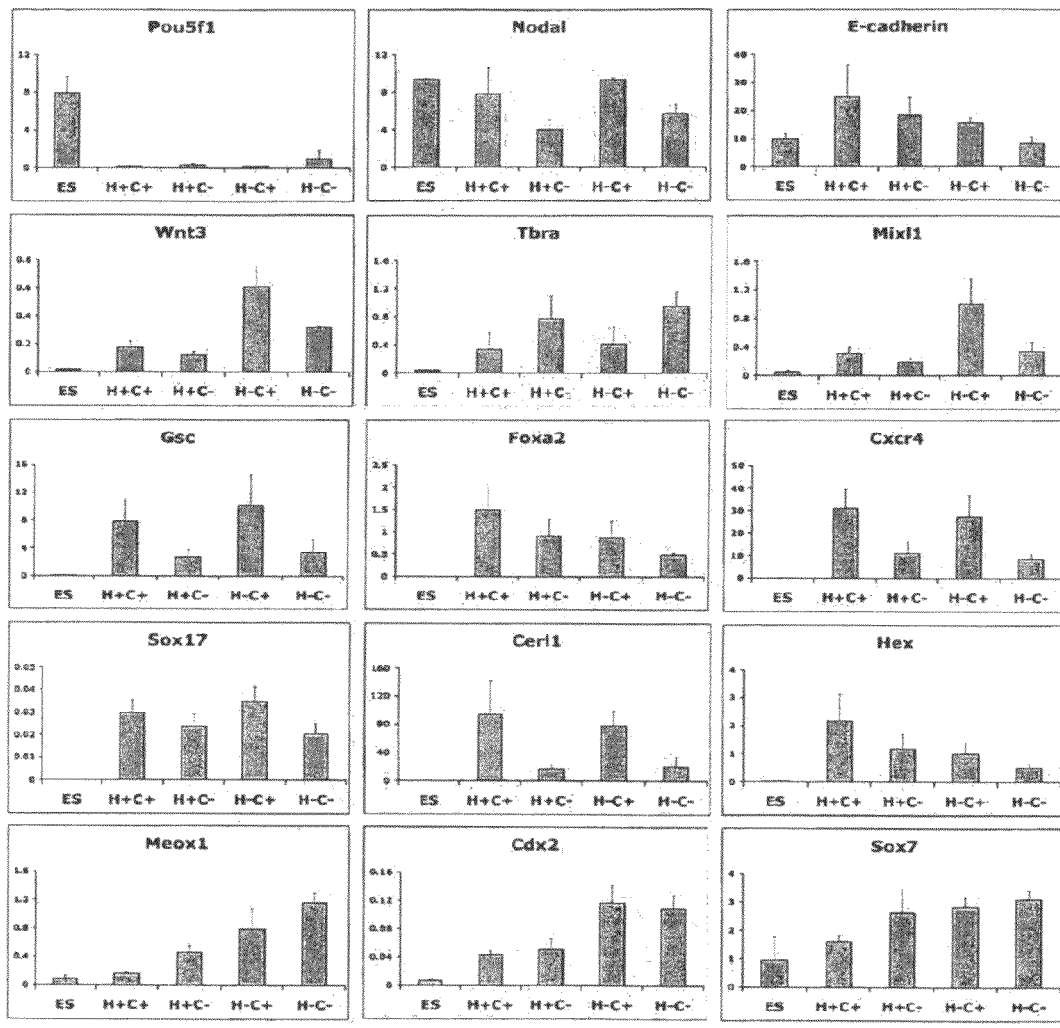

FIG. 9 shows Verification of microarray gene expression profiles by quantitative real-time RT-PCR.
Quantitative real-time RT-PCR. RNA was prepared from the four cell fractions sorted by flow cytometry following 7 days of differentiation. The differentiation conditions were as described in FIG. 4. The y axis represents relative expression calculated by normalising the transcript number to the TBP transcript number. Values represent the mean relative expression value from 2 independent experiments. Error bars represent standard deviations.

Figure 10:
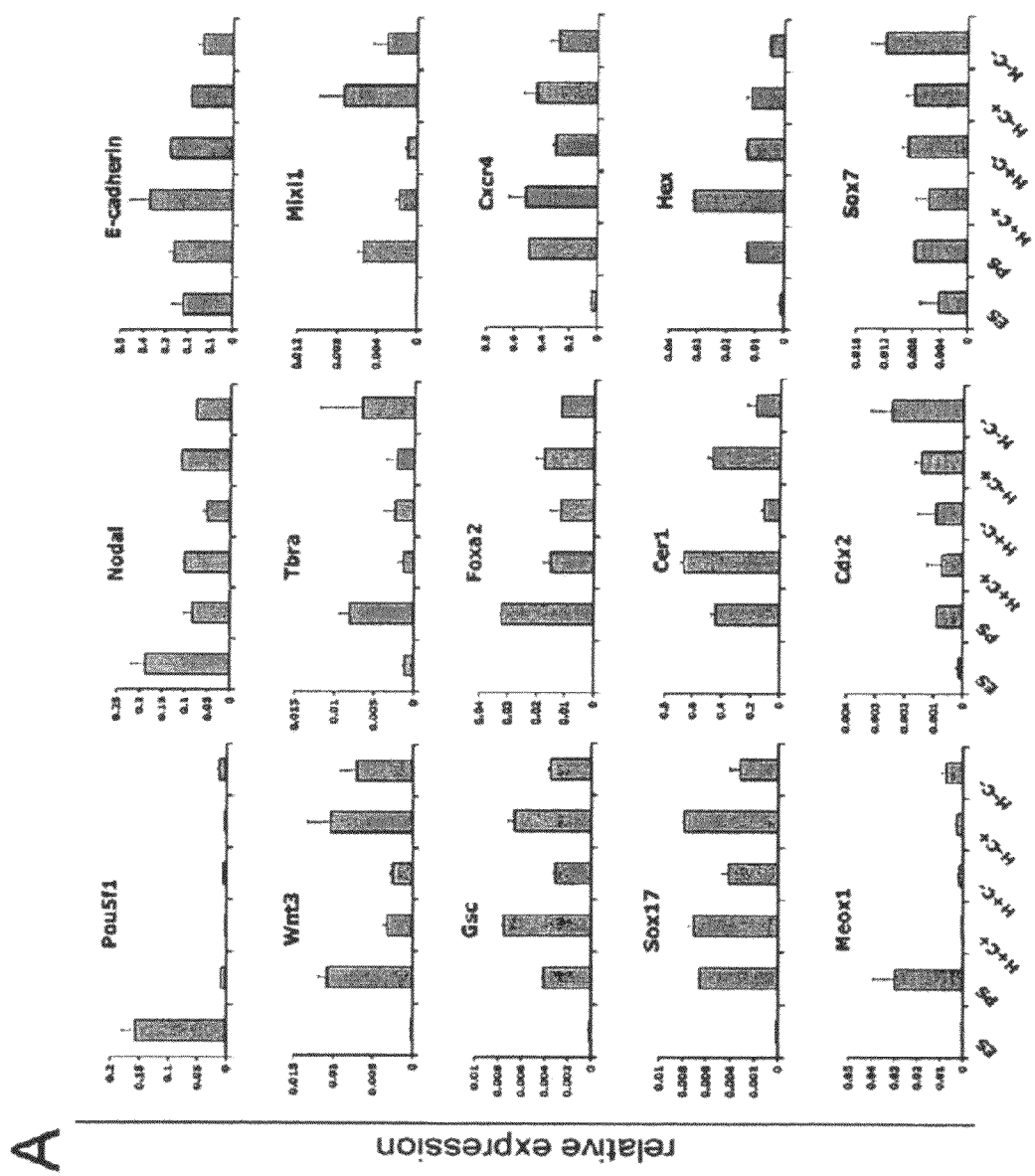
Figure 10:
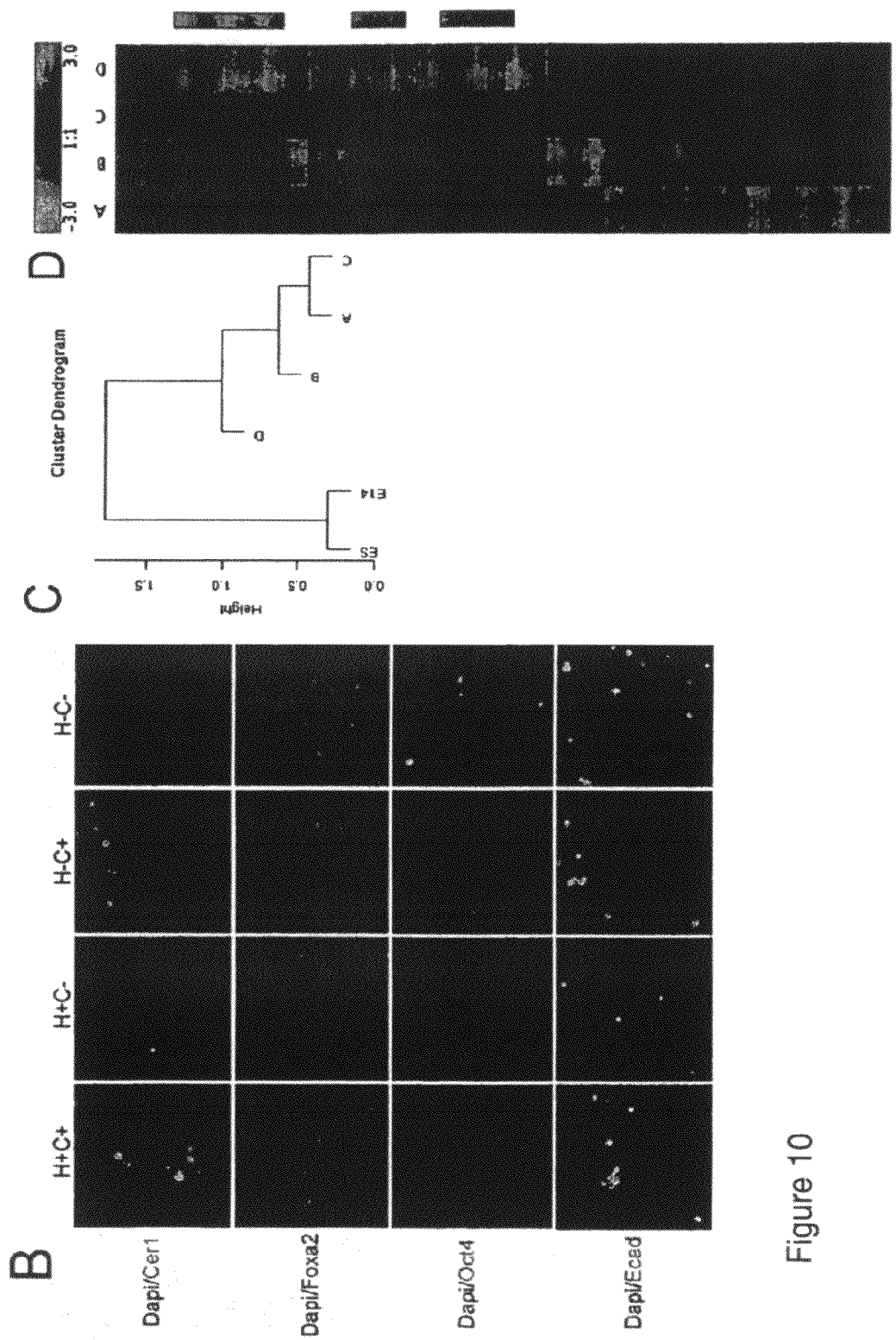
Figure 10:
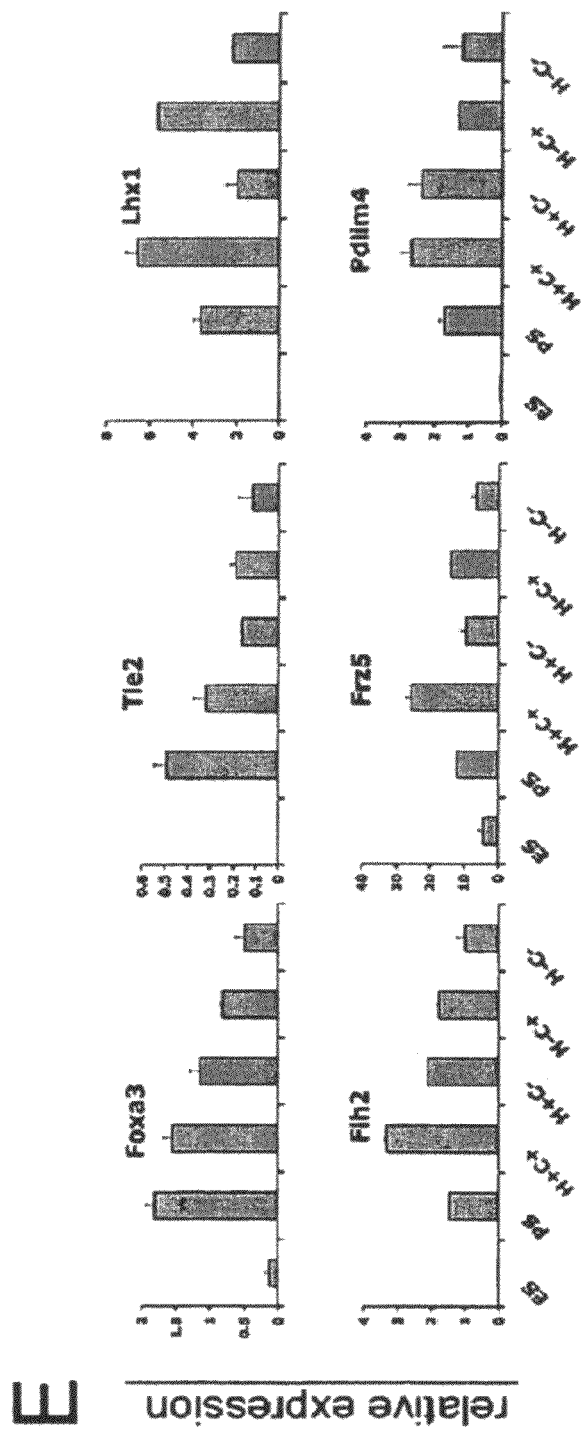

FIG. 10. Hex and Cxcr4 marks the emerging ADE cell population
(A) Quantitative real-time RT-PCR. RNA was prepared from the four cell fractions sorted by flow cytometry following 7 days of differentiation. The differentiation conditions were as described in FIG. 2d. The y axis represents relative expression calculated by normalising the transcript number to the $\beta$-actin transcript number. Values represent the mean relative expression value from 2 independent experiments. Error bars represent standard deviations. Purity checks on these populations were typically greater than 96% for the H+C+ and H−C+ populations and 91-93% for the H+C− and H−C− populations. (B) immunocytochemistry on ADE differentiated cells. The four cell fractions were sorted by flow cytometry following 7 days off differentiation as described in FIG. 2d. Cells were immunostained by anti-Cer1, anti-Coxa2, anti-Oct4 and Anti-Ecad. Nucleic were stained with DAPI. Green Cer1, Oct4 and Ecad positive cells were detected using an Alexa-488 secondary antibody and red FoxA2 positive cells were detected using an Alexa-568 secondary antibody. (C) Gene expression profiling of Hex (RS) and CXCR4 sorted cell populations. Cluster dendagram showing the relationship between the different cell populations and ES cells. Clustered normalised data using the 1-Perason's correlation coefficient as a measure of similarity. A=H+C+, C=H−C+, D=H−C−, ES=Hex$^{RS}$ ES cells, E14=H14Tg2a wild-type ES cells. The figure indicates that the H+C+ fraction is most closely related to the H−C+ and all four fractions are closer to each other, than any fraction is to ES cells. (D) Hierarchical clustering of the differentially expressed genes identified in a pairwise analysis of populations A, B, C and D (see methods). Based on the observations in C, this comparison is made in the absence of these cell dataset. Red bars indicate expression cluster. (E) Quantitative real-time RT-PCR of genes differentially expressed in the ADE-like fraction by microarray analysis. RNA was prepared from the four Hex/Cxcr4 cell fractions sorted by flow cytometry following 7 days of differentiation. The differentiation conditions were as described in FIG. 2d. The y axis represents relative expression calculated by normalising the transcript number to the Tata box-binding protein (TBP) transcript number. Values represent the mean relative expression value from 3 independent experiments. Error bars represent standard derivations.

Figure 11:
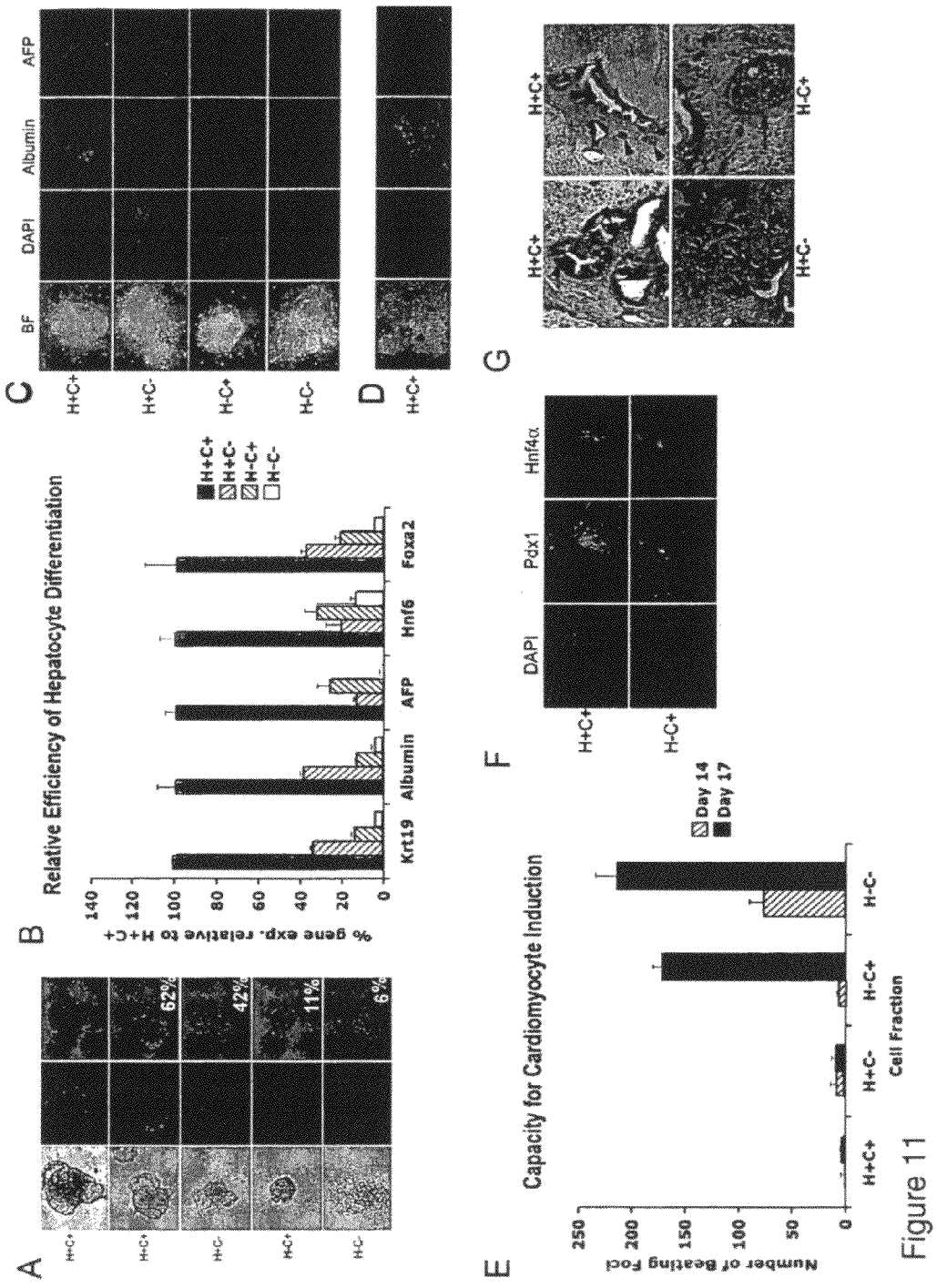

FIG. 11. ADE cell cultures can be further differentiated towards mature endodermal lineages in vitro and in vivo
(A) Induction of hepatocytes. Day 7 ADE cultures were sorted into 4 cell fractions and plated into hepatocyte inducing conditions as aggregates for 2 days. At this timepoint RS protein was only observed in the H+C+ and H+C− cell aggregates. (B) Quantitative real time RT-PCR for genes expressed in hepatic differentiation. Expression levels are represent as a percentage of that achieved in cells derived from the H+C+ fraction. Values are based on relative expression calculated by normalising the transcript number to the Tata box-binding protein (TBP) transcript number. (C) 2 day hepatocyte cell aggregates were plated on gelatine for a further 3 days. Cells were immunostained with anti-albumin, anti-AFP and nucleic stained with DAPI. Green albumin positive cells were detected using an Alexa-488 secondary antibody and red AFP positive cells were detected using an Alexa-568 secondary antibody. A few albumin positive cells were observed in the H+C+ and H+C− samples and these samples contained the highest percentage of AFP positive cells. (D) By day 13 of the hepatocyte culture (day 20 of the total culture period) many albumen positive cells were present in the H+C+ cultures. (E) Quantitation of cardiomyocyte induction based on scoring of beating foci. Data represents the average of four independent cultures. Cells were differentiated as in C and D. (F) Induction of pancreatic progenitors. Day 7 differentiated cultures were sorted into 4 cell fractions and plated in pancreatic progenitor inducing conditions for 5 days (see methods). Cells were immunostained with anti-Pdx1 and anti-HNF4α and nucleic stained with DAPI. The H+C+ fraction was both quantitatively and qualitatively more efficient at generating Pdx1/HNF4α clusters. Typical clusters for the H+C+ (n=9) and H−C+ (n=4) fractions. The H−C− fraction produced a single Pdx1/HNF4α positive cluster, while the H+C− fraction did not produce any. Green Pdx1 positive cells were detected using an Alexa-488 secondary antibody and red Hnf4α positive cells were detected using an Alexa-568 secondary antibody. We obtained 9 Pdx1/Hnf4α positive clusters from H+C+ cultures, 4 from H−C+ cultures and 1 from H−C− cultures. (G) Analysis of sorted cell populations in kidney capsule explants. Growths arising from the four sorted cells fractions were sectioned, stained with PAS and counterstained with Hematoxylin and Eoisin. Gut-like epithelial structures containing PAS positive secretory granules (deep red, black arrowheads) were present in H+C+ and H+C− growths. Cartilage (black arrow) was observed in the H−C+ growths.

Figure 12:
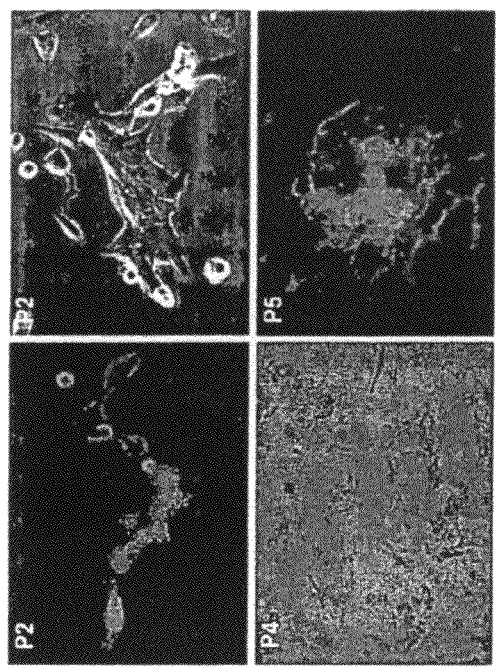
Figure 12:
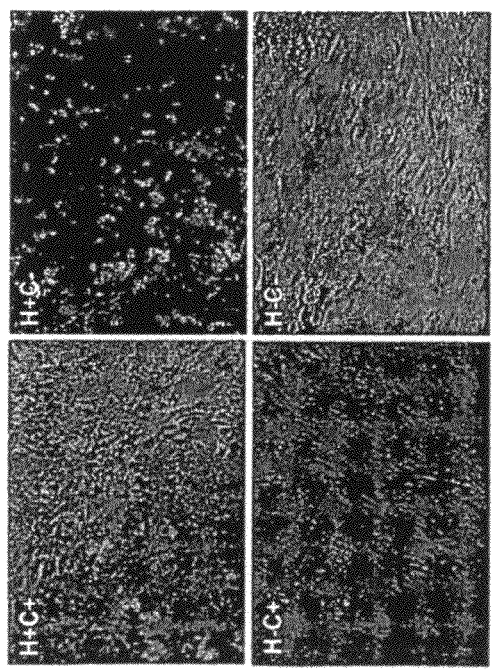
Figure 12:
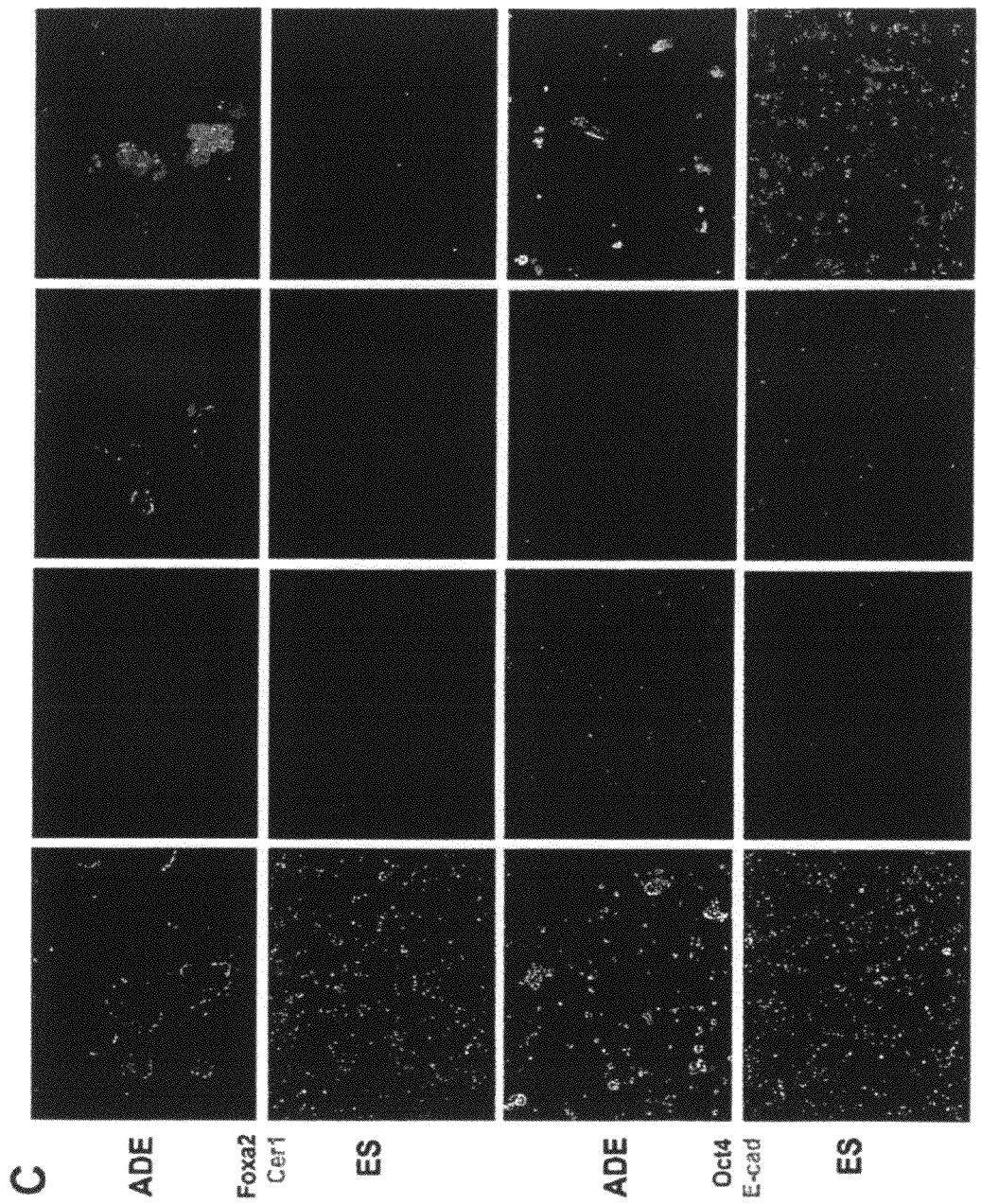
Figure 12:
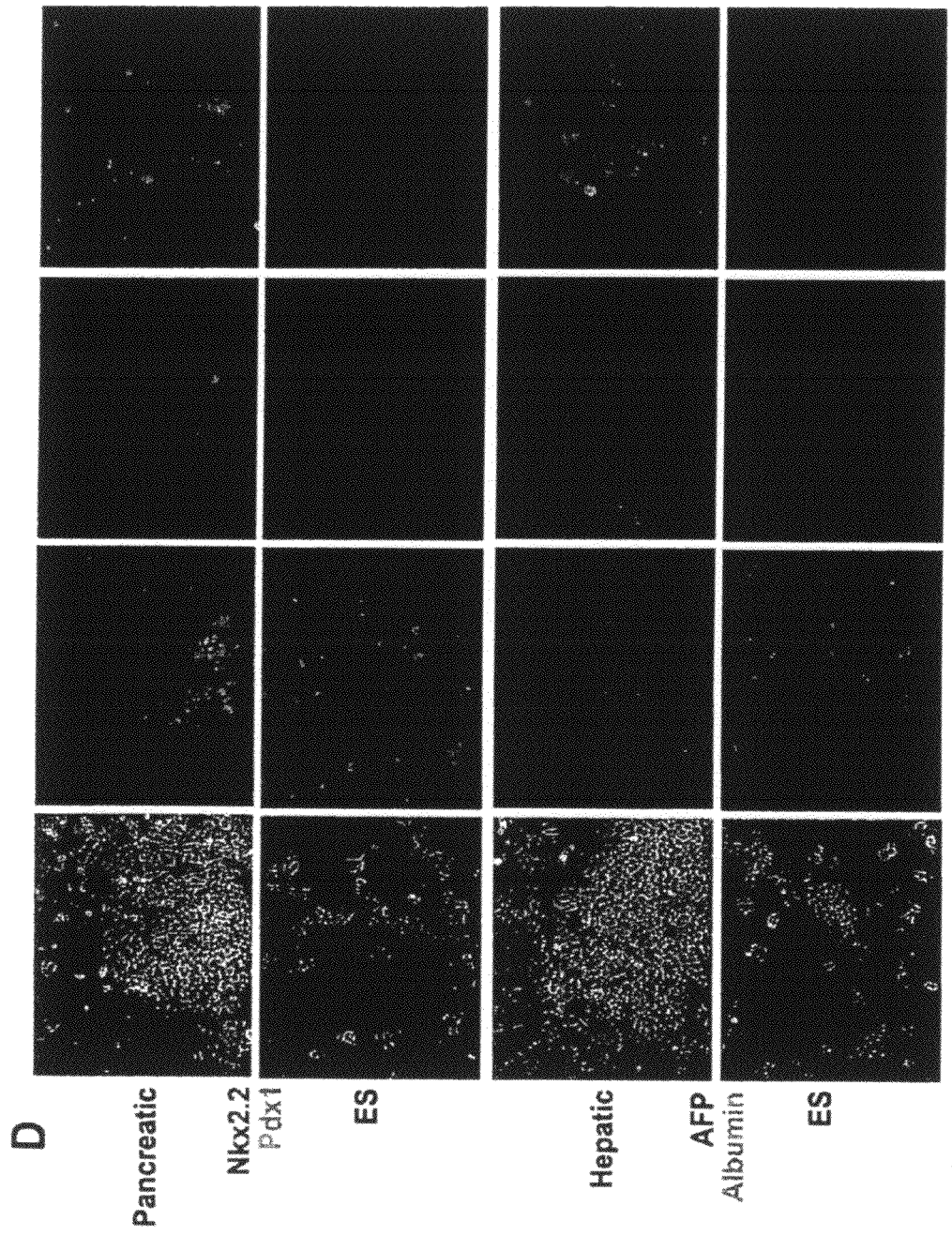

FIG. 12. Expansion of ADE progenitors derived from differentiating ES cell culture (A) FACS purified fractions from differentiating ES cell cultures plated and grown in culture for 12 days. The images are overlays of phase contrast and red fluorescence. Images captured with 10× objective (B) Images of colonies and cells in culture from the double positive H+C+ fraction. Top left 20×, bottom left 10×, top right 40×, bottom right 40×. Passage numbers 2, 4 and 5 are indicated on the figure. (C) Antibody staining of H+C+ cells in culture for six passages compared to ES cell controls. Cells were immunostained with anti-FoxA2, anti-Cer1, anti-Oct4 and anti-E-cadherin and nucleic stained with DAPI, FoxA2 and Oct 4 red were detected using Alexa-568 secondary antibody and Cer1 and E-cadherin green were detected using Alexa −488 secondary antibody. (D) Antibody staining of passage 7 H+C+ cultures challenged to further differentiate towards pancreatic or hepatic fates. Top panel: cells were immunostained with anti-Nkx2.2, anti-Pdx1 and nucleic stained with DAPI. Nkx2.2 red was detected using Alexa-568 secondary antibody and Pdx1 green was detected using Alexa-488 secondary antibody. Bottom panel: cells were immunostained with anti-albumin, anti-AFP and nucleic stained with DAPI. Green albumin positive cells were detected using an Alexa-488 secondary antibody and red AFP positive cells were detected using an Alexa-568 secondary antibody.

Figure 13:
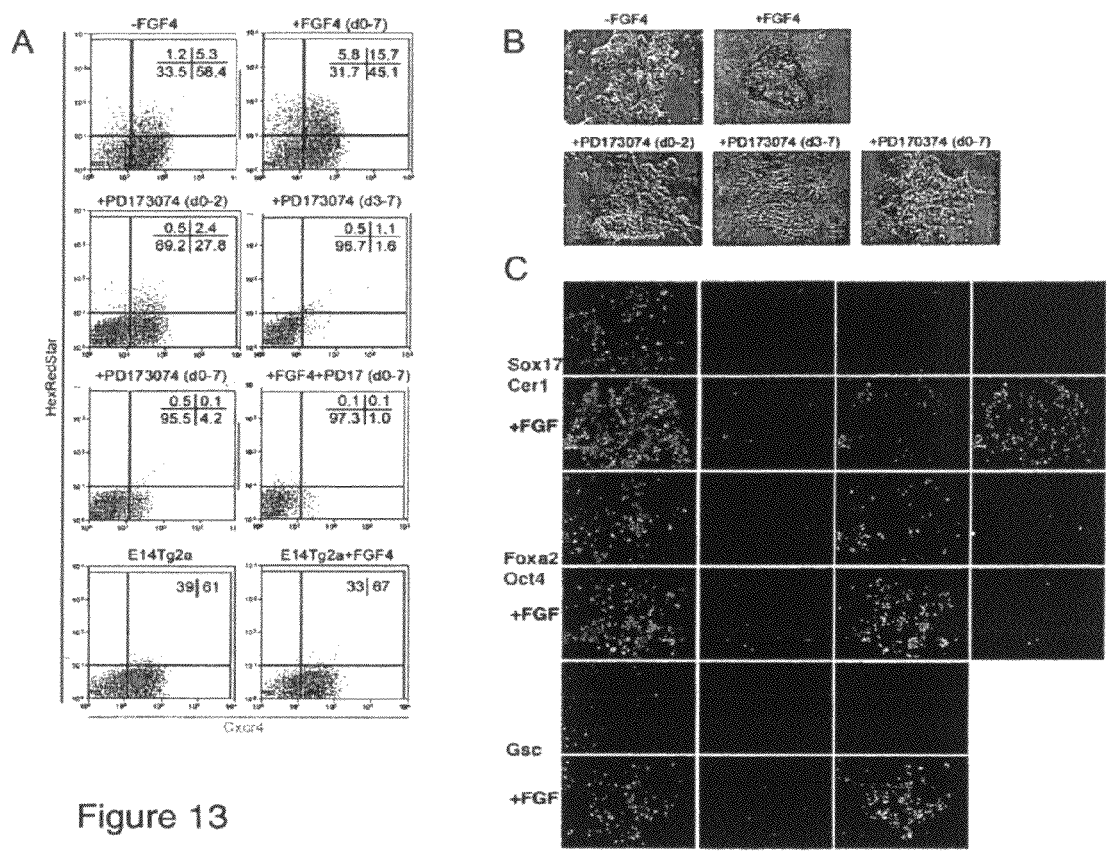
Figure 13:
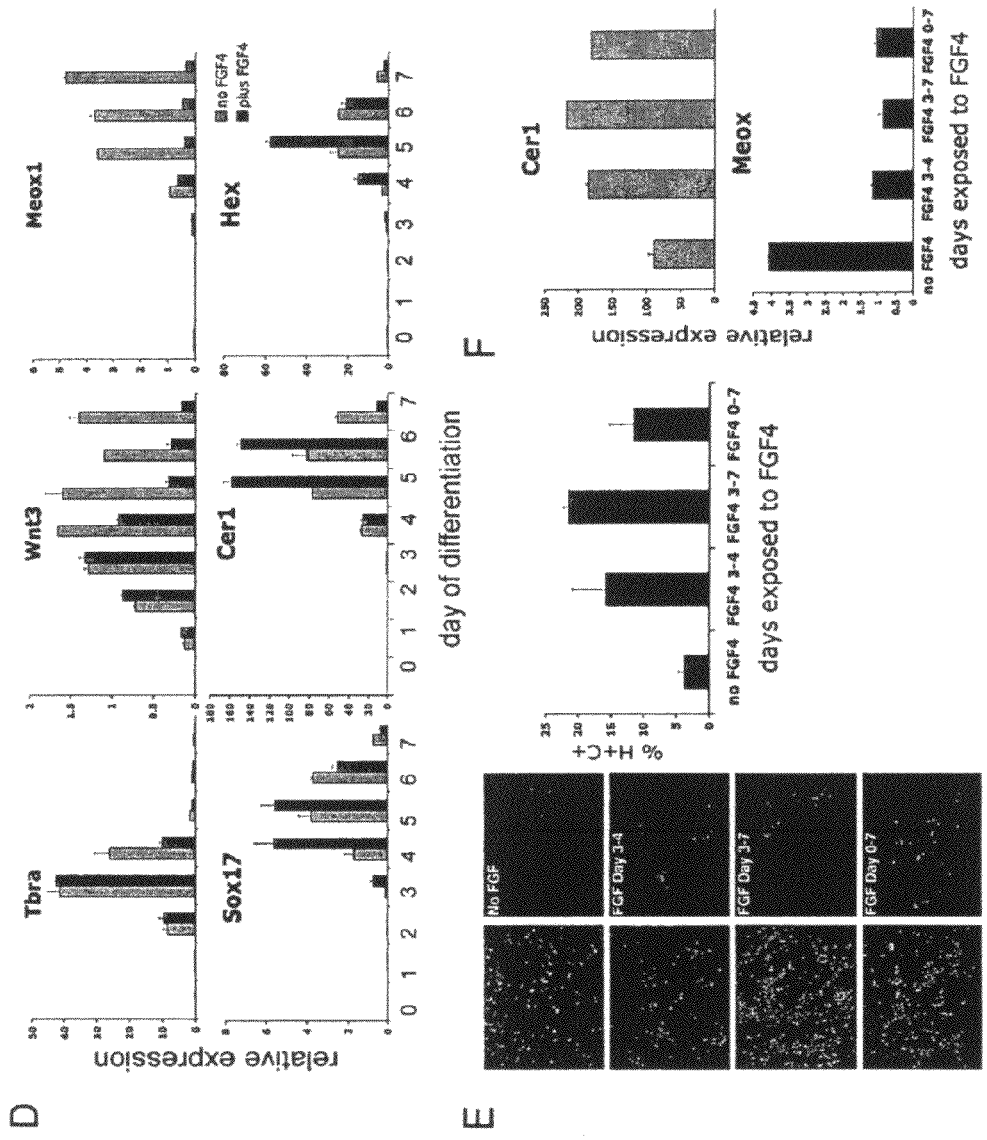

FIG. 13. Defining the requirement for ADE induction in chemically defined serum-free culture conditions reveals a novel requirement for FGF signalling (A) Flow cytometry of Hex$^{RS}$ and E14Tg2a ES cells differentiated in monolayer culture. All differentiation was carried out in N2B27 plus activin and Bmp4 for two days, followed by five days in SF03 plus activin and EGF or the FGF antagonist, PD173074 as indicated. (B) Fluorescence images of cell morphology. Cells were cultured as above with FGF4 or the Fgf antagonist PD173074 as indicated. (C) Immunohistochemistry showing the expression of anterior mesendoderm markers in response to FGF4 in defined monolayer culture. Nucleic were stained with DAPI. Green Ger1 and Oct4 positive cells were detected using Alexa-488 secondary antibody and red Sox17, Foxa2 and Gsc positive cells were detected using Alexa-568 secondary antibody. (D) Real time quantitative PCR from day 0 to day 7 of serum-free differentiation showing gene expression changes in respect to FGF4. The x axis represents the time in days at which the RNA was collected (timepoint 0—ES cells) and the y axis represents relative expression calculated by normalising the transcript number by to the Tata box-binding protein (TBp) transcript number. (E) Time course for FGF addition. Left panel, bright field and fluorescent images of cultures differentiated in monolayer with FGF added for the indicated times. Right panel, bar graph indicating the percentage H+C+ obtained in these experiments as determined by flow cytometry. (F) Optimal levels of H+C+ correlates with optimal levels of ADE marker expression. Real time quantitative PCR indicating the relative level of transcription of a representative set of markers in response to different periods of exposure to FGF4 in monolayer culture. The x axis represents the time in days at which the RNA was collected (timepoint 0=ES cells) and the y axis represents relative expression calculated by normalising the transcript number by to the Tata box-binding protein (TBP) transcript number.

Figure 14:
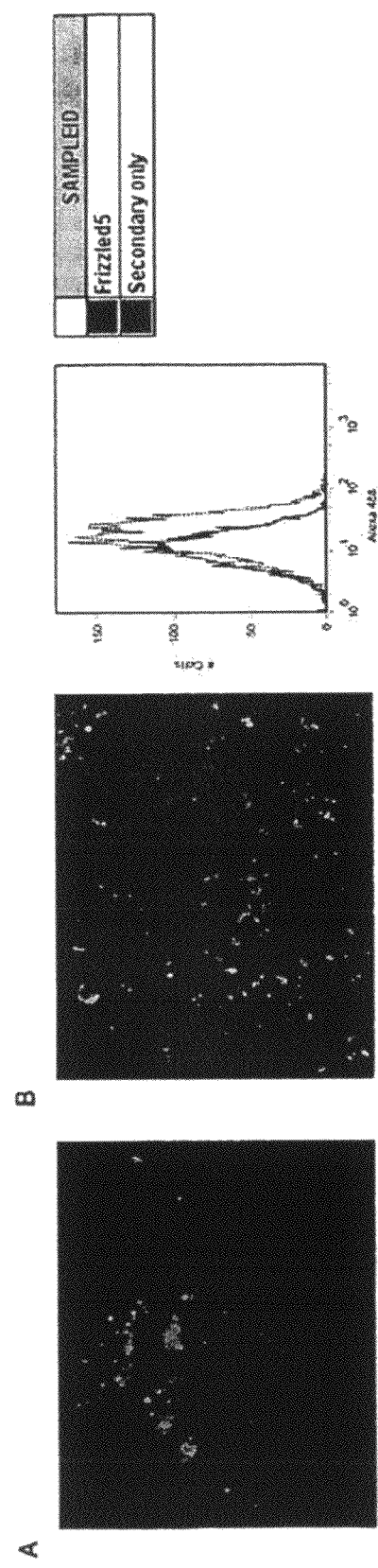
Figure 14:
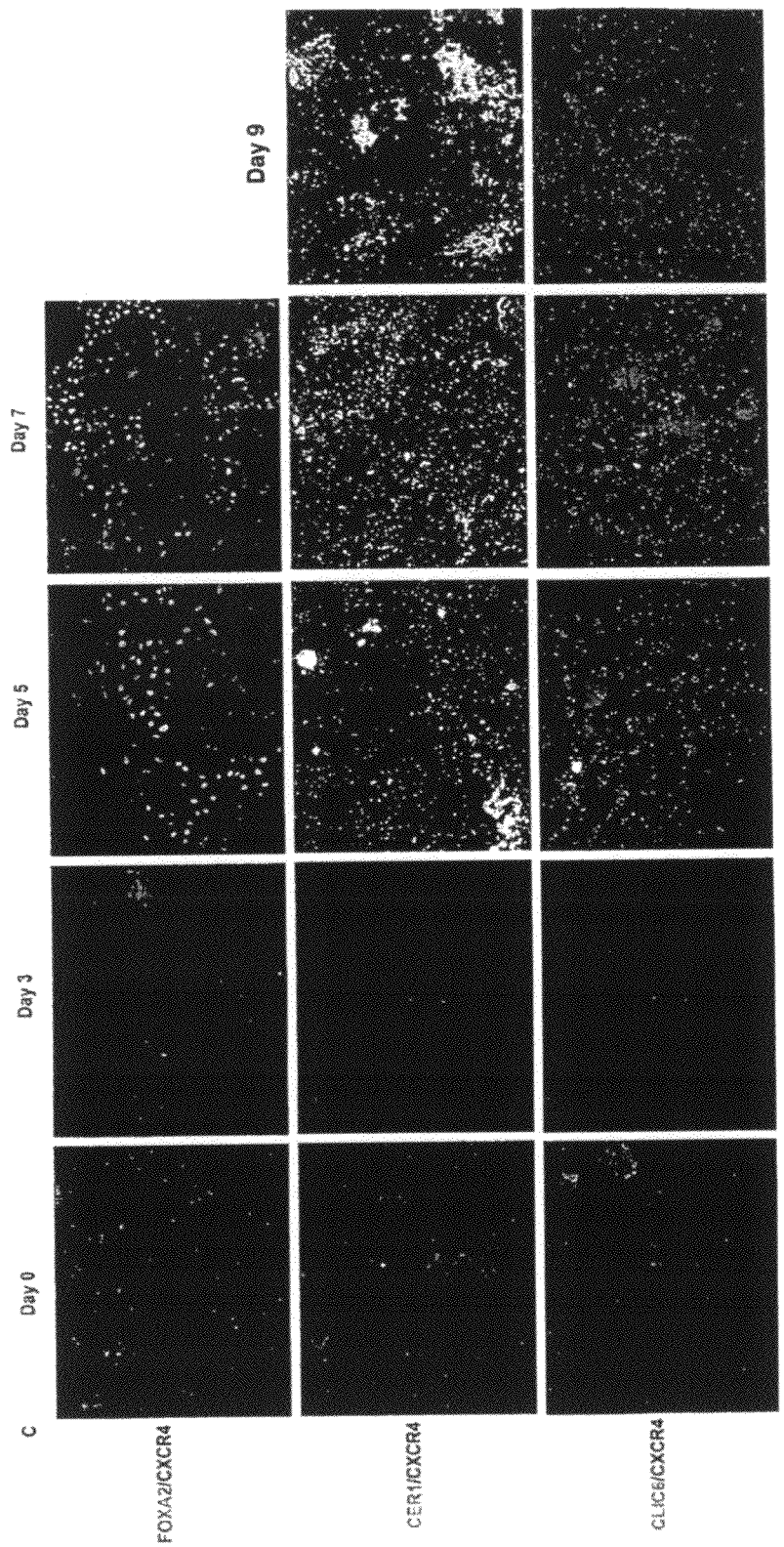

FIG. 14 shows the differentiation of human ES cells to anterior definitive endoderm Top panel (A) was differentiation with sodium burate and active as described in (Hay et al., 2008b) and the image in (B) is of cells differentiated with activin A and Wnt3a (Hay et al., 2008a). Cells were stained with anti-CER1 (Santa Cruz) in green and anti-Cxcr4 (BD Biosystems, APC conjugate) red. The figure shows that both protocols produce heterogeneous endodermal differentiation, with the activin and Wnt protocol producing higher numbers of CER1 positive cells. Flow cytometry is also shown in (B). Here the cells at the same stage of differentiation as those depicted in the image were analyzed by flow cytometry for FRZD5, one of the new markers identified and described in (Morrison et al., 2008). A similar proportion of these cells appear to FRZD5 positive as express CER 1 by immuno-histochemistry. Panel C shows data of cell staining following cells which have undergone differentiation in accordance with the present invention.

Figure 15:
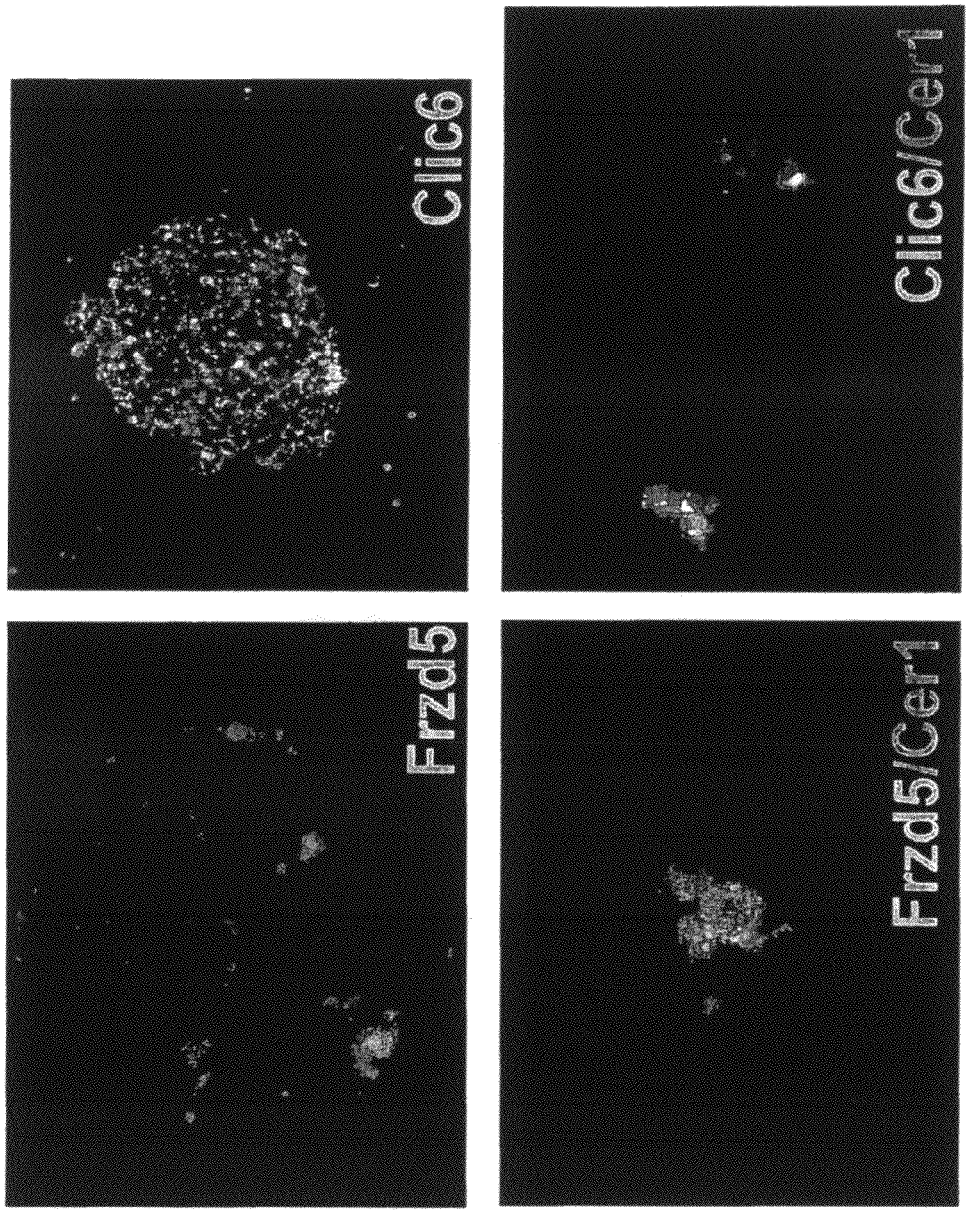

FIG. 15 shows an illustration of ADE staining by new cell surface markers identified in this work. Embryiod bodies were differentiated to make ADE and either stained with individual markers (top panel) or disassociated and stained with a combination of two antibodies (bottom panel). EBs differentiated under conditions used to generate ADE show an abundance of cells staining at their membrane (green) for either Frzd5 or Clic6. Nuclei are in blue and stained with Dapi. In the bottom panel, clumps of cells express both the ADE marker Cer1 (red or purple in the overlay) and either Frzd5 or Clic6.

Figure 16:
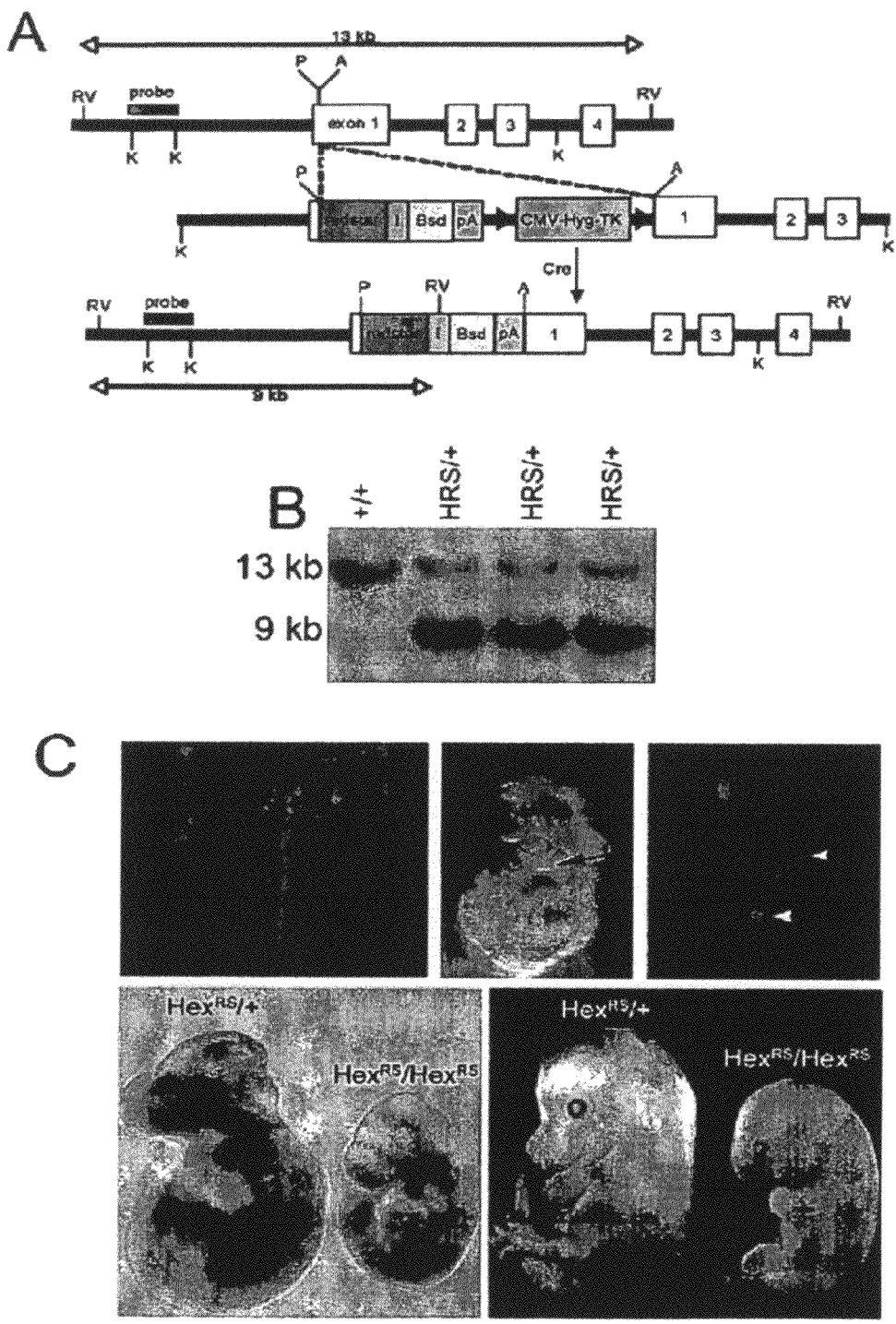

FIG. 16. RS protein recapitulates endogenous Hex expression (A) Schematic representation of the strategy used for the insertion of the redstar (RS) coding sequence into the Hex locus. (B) Southern blot indicating the correct insertion of the RedStar cassette into the Hex allele (9 kb band). Targeting frequency=40%. (C) The Hex$^{RS}$ mouse line recapitulates Hex expression and phenotype. Top panel, Hex$^{RS/+}$ embryos at E8, E8.5 and E9.5. RS expression is visible at E8 in the anterior definitive endoderm, at E8.5 in the ventral foregut (black arrow) and at E9.5 in the thryoid and liver primordial (white arrowheads). Lower panel, Hex$^{RS}$ homozygous mutant embryos and Hex$^{RS/+}$ littermates at E9.5 and E15.

Figure 17:
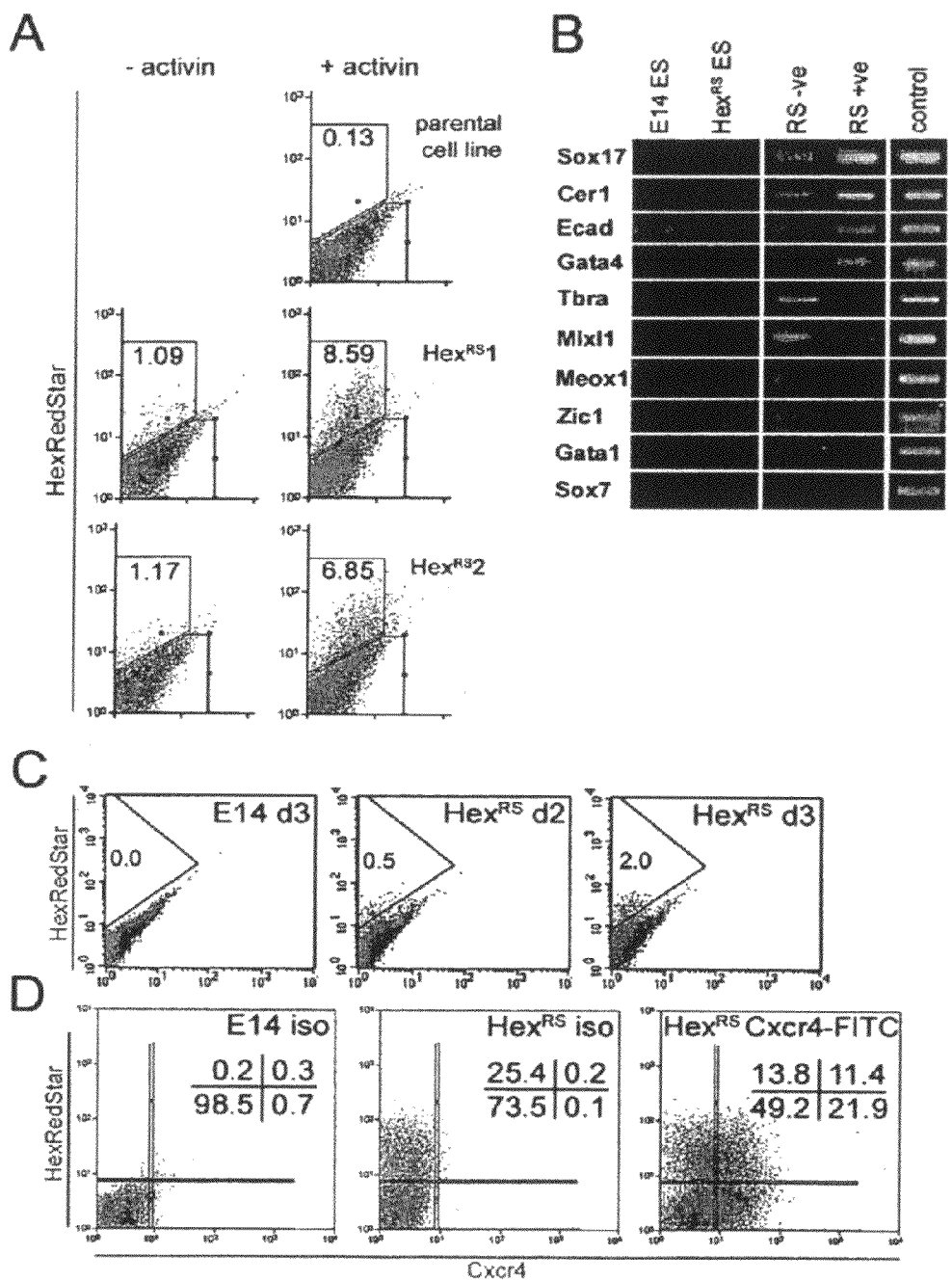

FIG. 17. In vitro expression of RS is specific to Hex expressing cell lineages.
(A) HRS and E14Tg2a (parental) ES cells cultured in serum containing media for 2 days followed by N2B27 plus or minus activin for 5 days. Percentages of RS expressing cells are indicated. (B) Semi-quantitative RT-PCR for a range of markers associated with endoderm (Sox17, Cer1, Ecadherin, Gata4), mesoderm (Tbra, Mixl1, Meox1, Gata1), ectoderm (Zic1) and parietal endoderm (Sox7) on RS positive and RS negative cell fractions sorted by flow cytometry. Samples were first analysed by quantitative RT-PCR for β-actin expression and normalised accordingly. (C) HRS and E14Tg2a ES cells cultured in early haematopoietic progenitor inducing conditions. Percentages of RS expressing cells are indicated. (D) Induction of H+C+ cells. Flow cytometry for RS and Cxcr4 (FITC) on day 7 cells differentiated as in 2A with the addition of activin and EGF.

Figure 18:
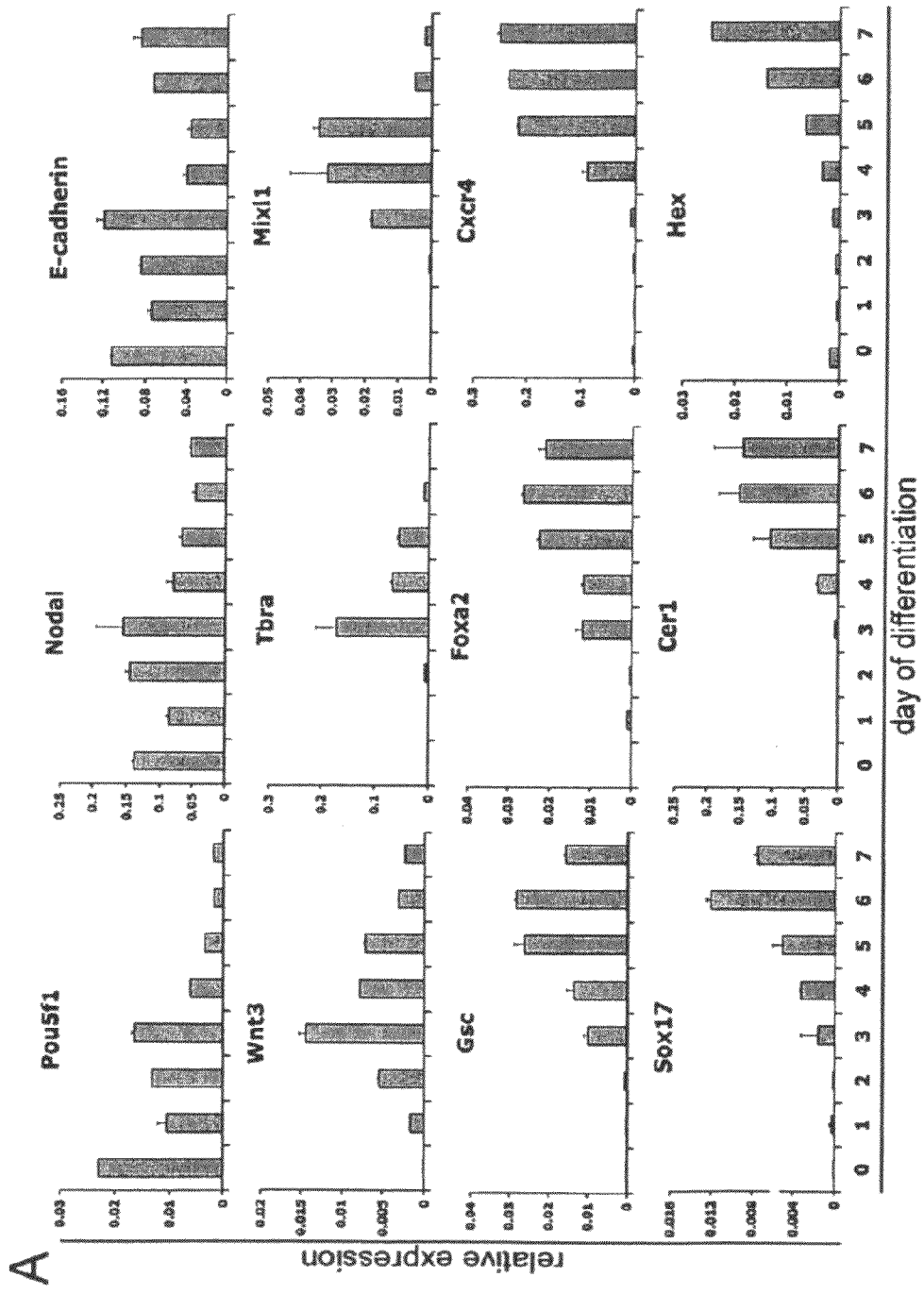
Figure 18:
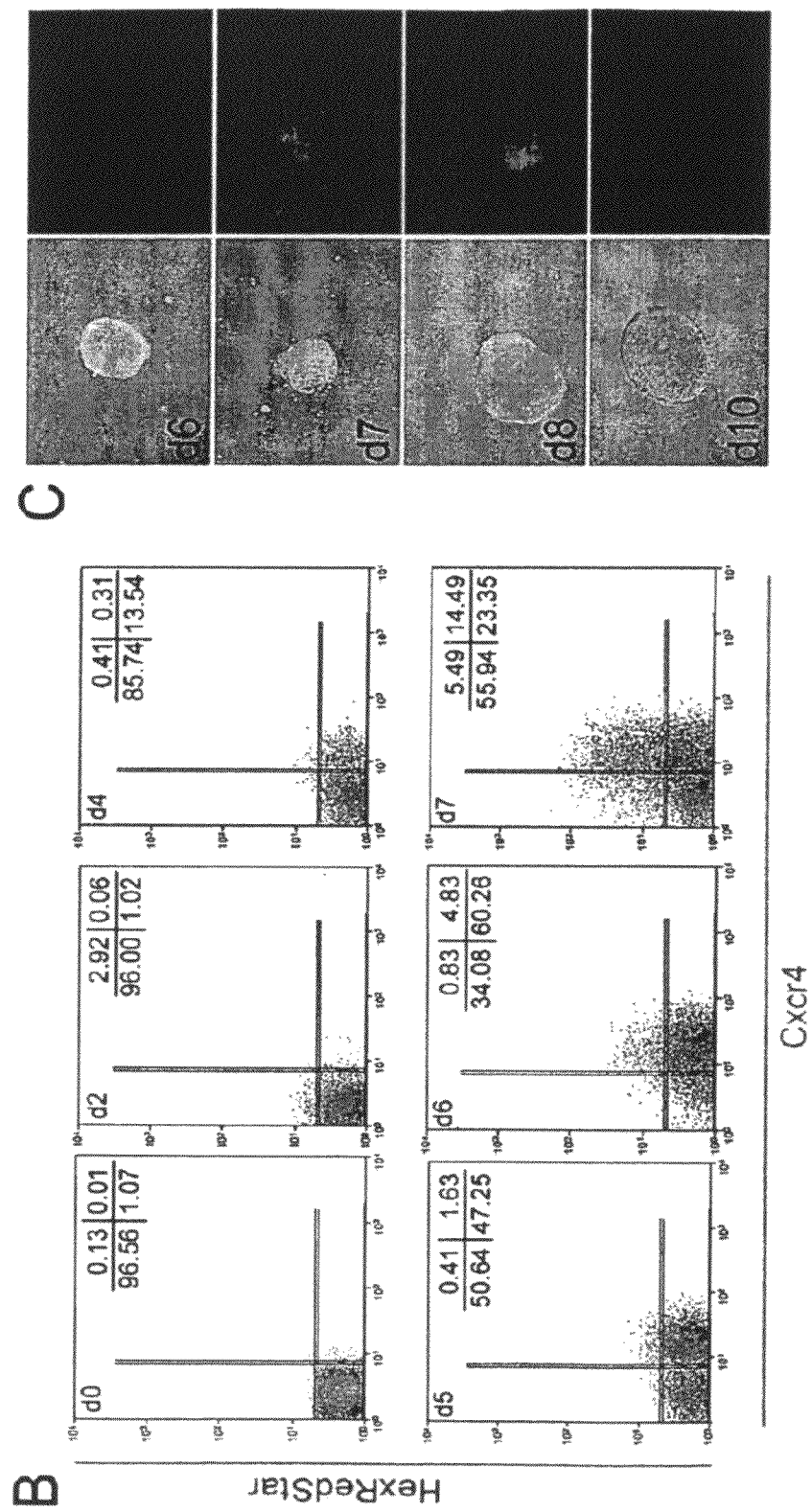

FIG. 18. In vitro differentiating cell cultures produce a gene expression dynamic similar to that observed during ADE induction in vivo
(A) Gene expression analysis during differentiation by quantitative real-time RT-PCR. The x axis represents the time in days when RNA was collected (timepoint 0=ES cells). The y axis represents relative expression calculated by normalising the transcript number by the β-actin transcript number. Values represent the mean of 2 independent experiments. Error bars represent the standard deviation. (B) Analysis of RS and CXCR4 expression by flow cytometry from day 0 to day 7 of differentiation. The percentages of the four cell fractions are indicated. (C) RS expression in differentiating cell aggregates. Images captured using a 10× objective.

Figure 19:
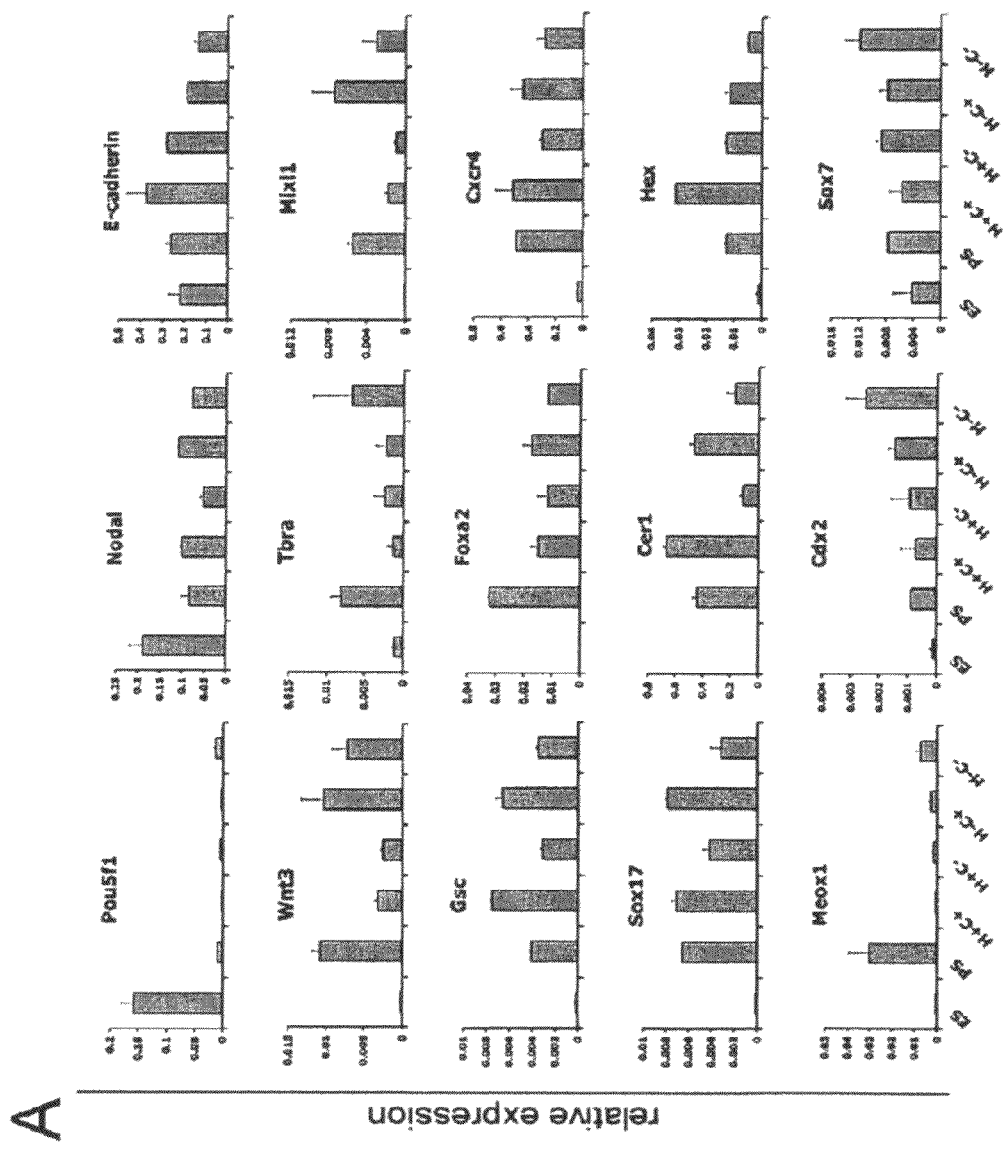
Figure 19:
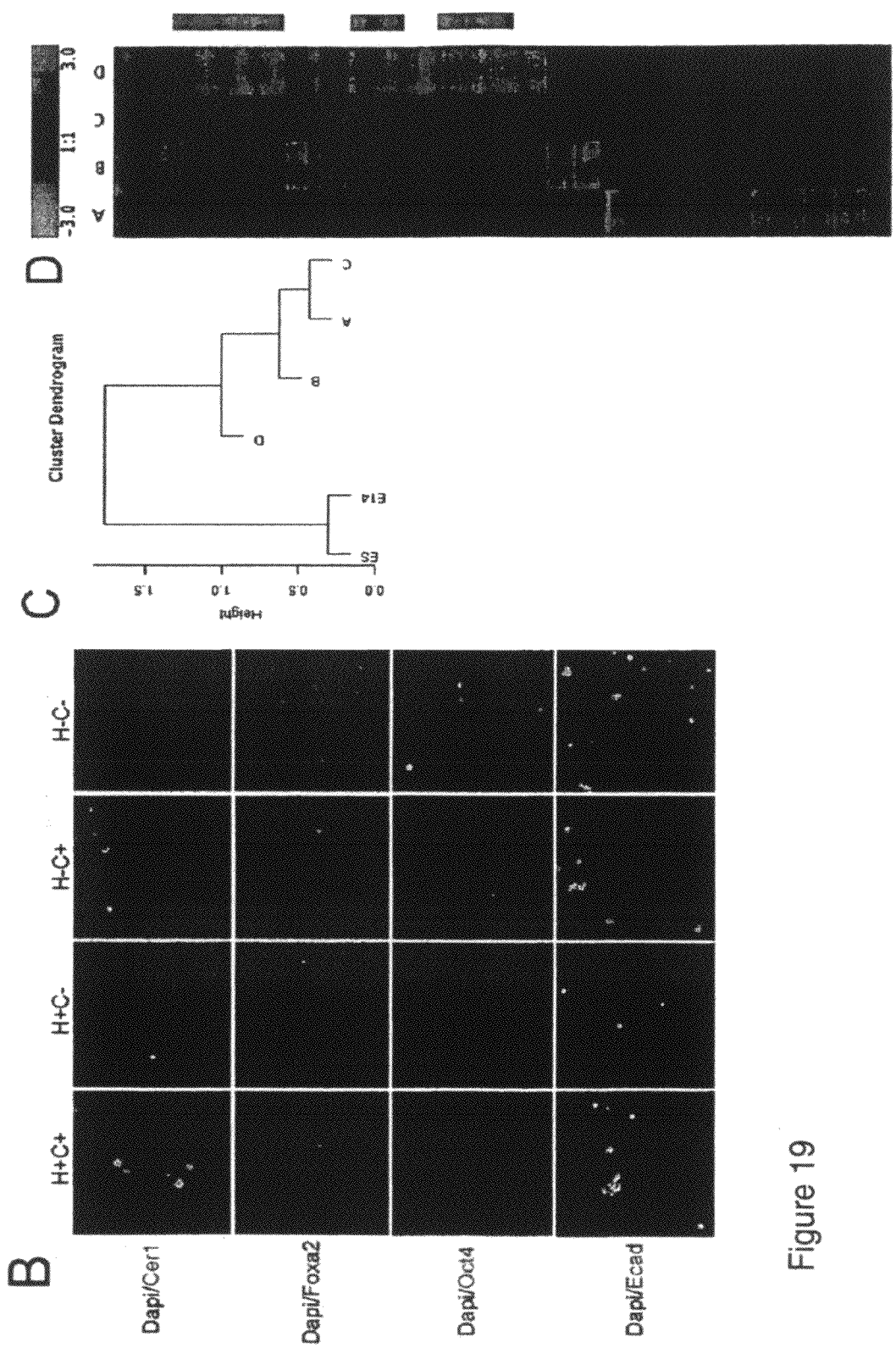
Figure 19:
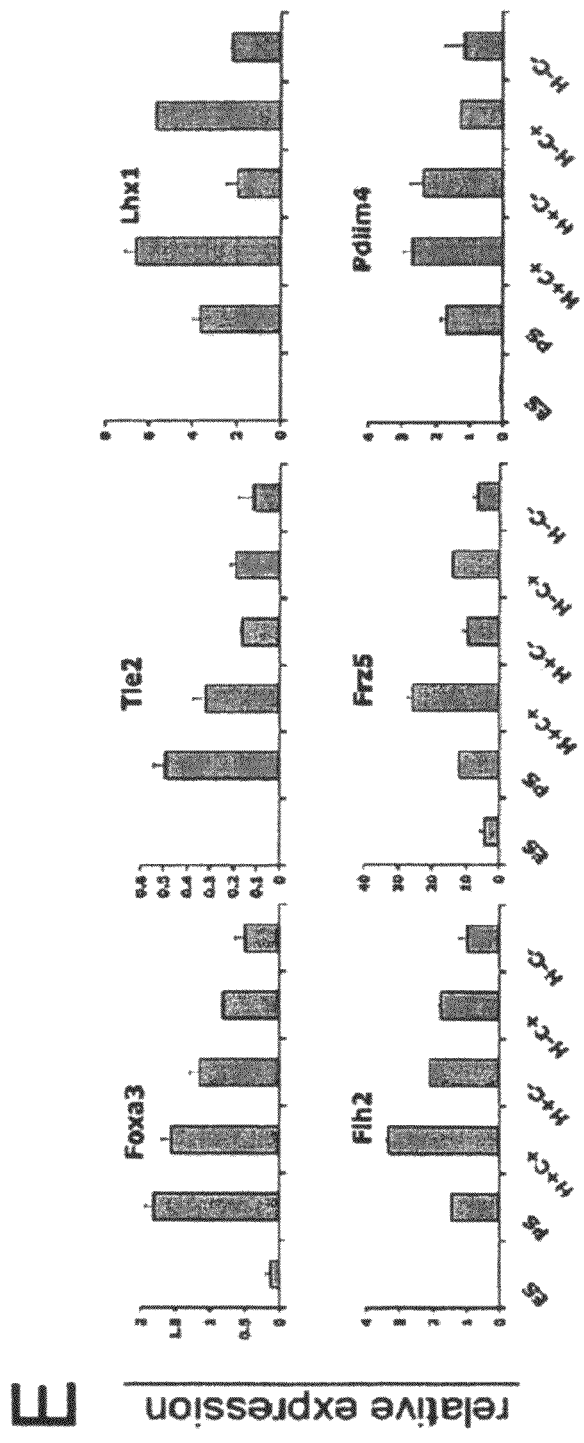

FIG. 19. Hex and Cxcr4 marks the emerging ADE cell population
(A) Quantitative real-time RT-PCR. RNA was prepared from the four cell fractions sorted by flow cytometry following 7 days of differentiation. The differentiation conditions were the same as FIG. 2D. The y axis represents relative expression calculated by normalising the transcript number to the β-actin transcript number. Values represent the mean from 2 independent experiments. Error bars represent standard deviations. Purity checks on these populations were typically greater than 96% for the H+C+ and H−C+ populations and 91-93% for the H+C− and H−C− populations. RT-PCR values for cells prior to sorting (PS) and ES cells (ES) are included for reference. (B) Immunostaining on ADE differentiated cells. The four cell fractions were sorted by flow cytometry following 7 days of differentiation. Cells were immunostained by anti-Cer1 (green), anti-Foxa2 (red), anti-Oct4 (green) and anti-Ecadherin (green). Nuclei were stained with DAPI (blue). Images captured using a 20× objective. (C) Gene expression profiling of Hex (RS) and CXCR4 sorted cell populations. Cluster dendrogram showing the relationships between the different cell populations and ES cells. Clustered normalised data using the 1—Pearson's correlation coefficient as a measure of similarity. A=H+C+, B=H+C−, C=H−C+, D=H−C−, ES=Hex$^{RS}$ ES cells, E14=E14Tg2a wild-type ES cells. The figure indicates that the H+C+ fraction is most closely related to the H−C+ and all four fractions are closer to each other, than any fraction is to ES cells. (D) Hierarchical clustering of the differentially expressed genes identified in a pairwise analysis of populations A, B, C and D (see methods). Based on the observations in C, this comparison is made in the absence of the ES cell dataset. Red bars indicate expression cluster. (E) Quantitative real-time RT-PCR of genes differentially expressed in the ADE-like fraction by micorarray analysis. RNA was prepared from the four Hex/Cxcr4 cell fractions sorted by flow cytometry following 7 days of differentiation. The differentiation conditions were the same as FIG. 2D. RT-PCR values for cells prior to sorting (PS) and ES cells (ES) are included for reference. The y axis represents relative expression calculated by normalising the transcript number to the Tata box-binding protein (TBP) transcript number. Values represent the mean from 3 independent experiments. Error bars represent standard deviations.

Figure 20:
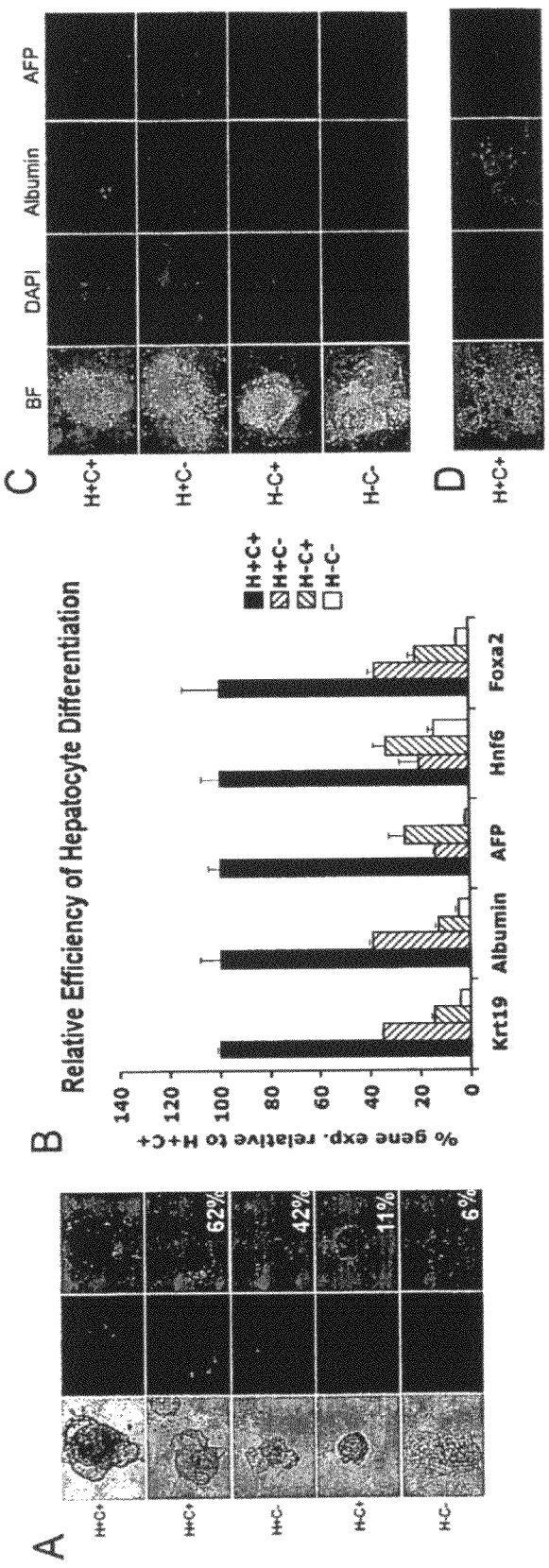
Figure 20:
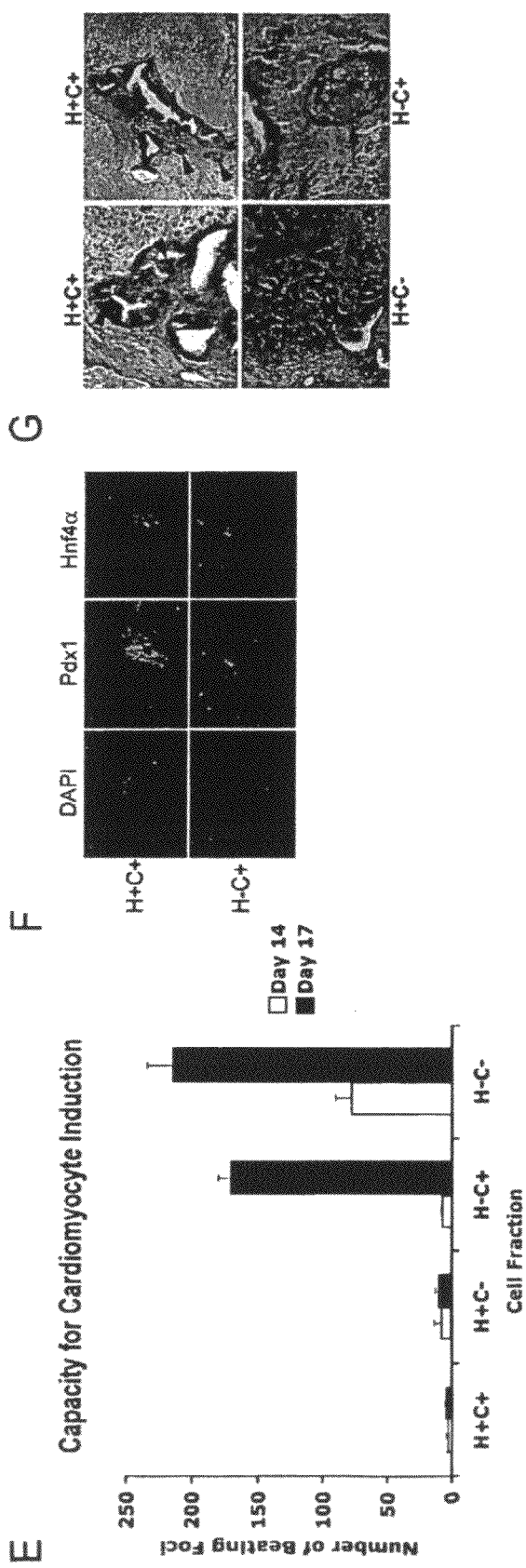

FIG. 20. ADE cell cultures can be further differentiated towards mature endodermal lineages in vitro and in vivo
(A) Induction of hepatocytes. Day 7 ADE cultures were sorted into 4 cell fractions and plated into hepatocyte inducing conditions as aggregates for 2 days. At this timepoint RS protein was only observed in the H+C+ and H+C− cell aggregates. White numbers shown on panels represent the percentage of Hex positive cells present in these cultures as measured by flow cytometry. Images captured using a 10× objective. (B) Quantitative real time RT-PCR for genes expressed at day 9 of hepatic differentiation. Expression levels are represented as a percentage of that achieved in cells derived from the H+C+ fraction. Values are based on relative expression calculated by normalising the transcript number to the Tata box-binding protein (TBP) transcript number. (C) Hepatocyte cell outgrowths on day 12 of total culture period. Cells were immunostained with anti-Albumin (green), anti-AFP (red) and nuclei stained with DAPI (blue). A few Albumin positive cells were observed in the H+C+ and H+C− samples and these samples contained the highest percentage of AFP positive cells. Images captured using a 10× objective. (D) Hepatocyte cultures on day 20 of the total culture period. Many Albumin positive cells can be observed in the H+C+ cultures. Images captured using a 10× objective. (E) Capacity for cardiomyocyte induction. Quantification of beating foci. Data represents the average of four independent wells and error bars the standard deviation. Cells were differentiated as in C and D. (F) Induction of pancreatic progenitors. Day 7 differentiated cultures were sorted into 4 cell fractions and plated in pancreatic progenitor inducing conditions for 5 days (see methods). Cells were immunostained with anti-Pdx1 (green) and anti-HNF4α (red) and nuclei stained with DAPI (blue). The H+C+ fraction was both quantitatively and qualitatively more efficient at generating Pdx1/HNF4α clusters. Nine Pdx1/HNF4α were obtained from the H+C+ cultures, four from H−C+ cultures, one from H−C− cultures and none from the H−C+ cultures. Images captured using a 20× objective. (G) Analysis of sorted cell populations in kidney capsule explants. Sections of growths were stained with PAS and counterstained with Hematoxylin and Eosin. Gut-like epithelial structures containing PAS positive secretory granules (deep red, black arrowheads) were present in H+C+ and H+C− growths. Cartilage (black arrow) was observed in the H−C+ growths. Images captured using a 20× objective.

Figure 21:
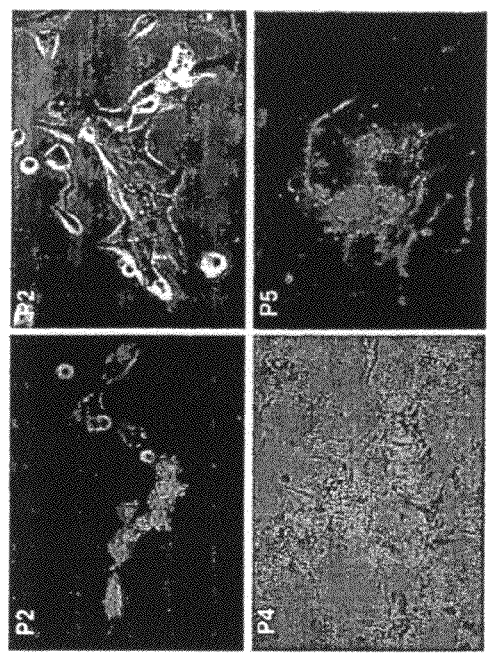
Figure 21:
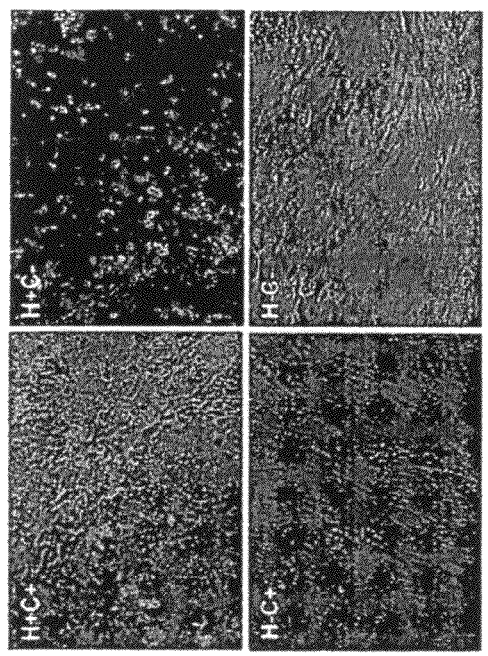
Figure 21:
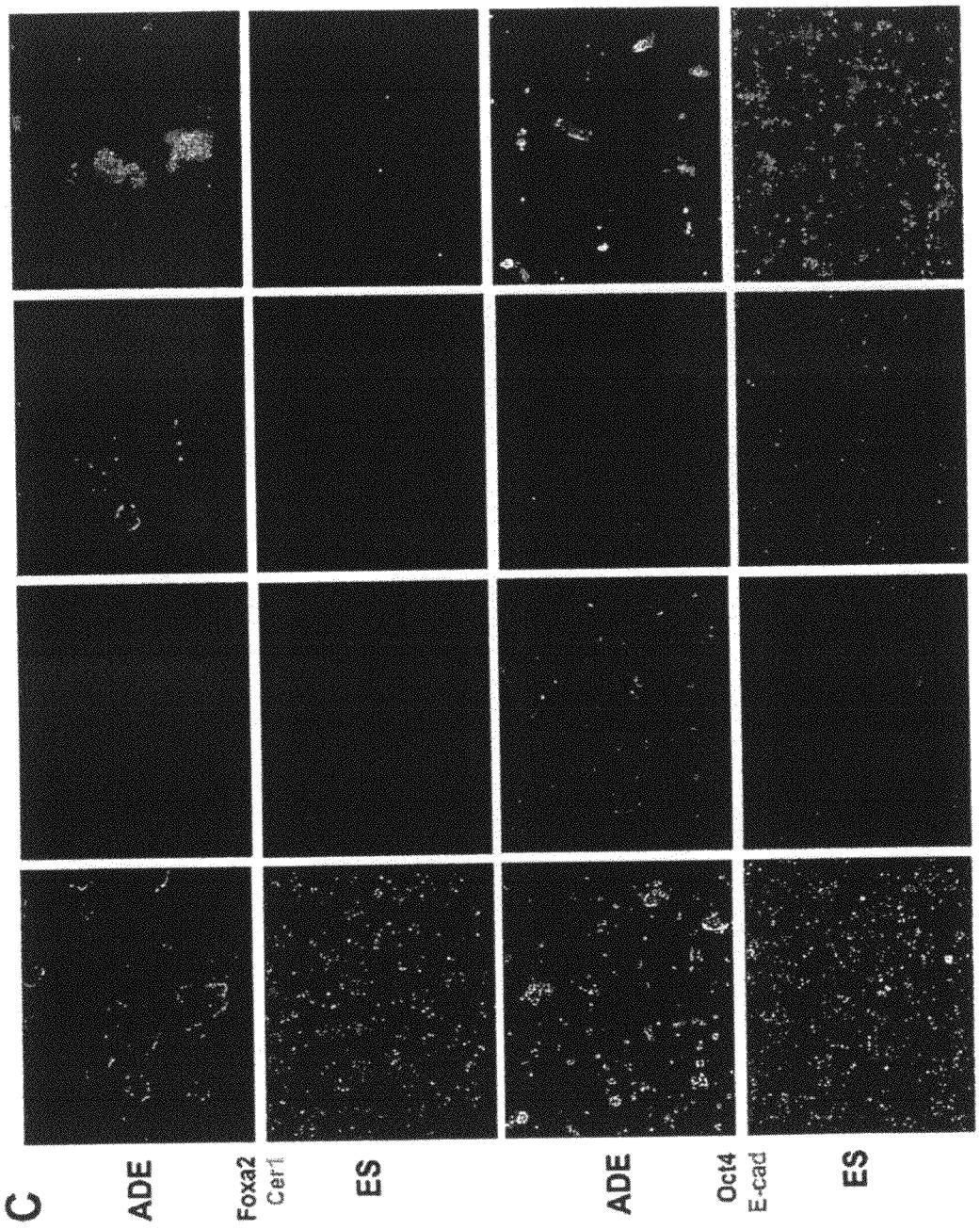
Figure 21:
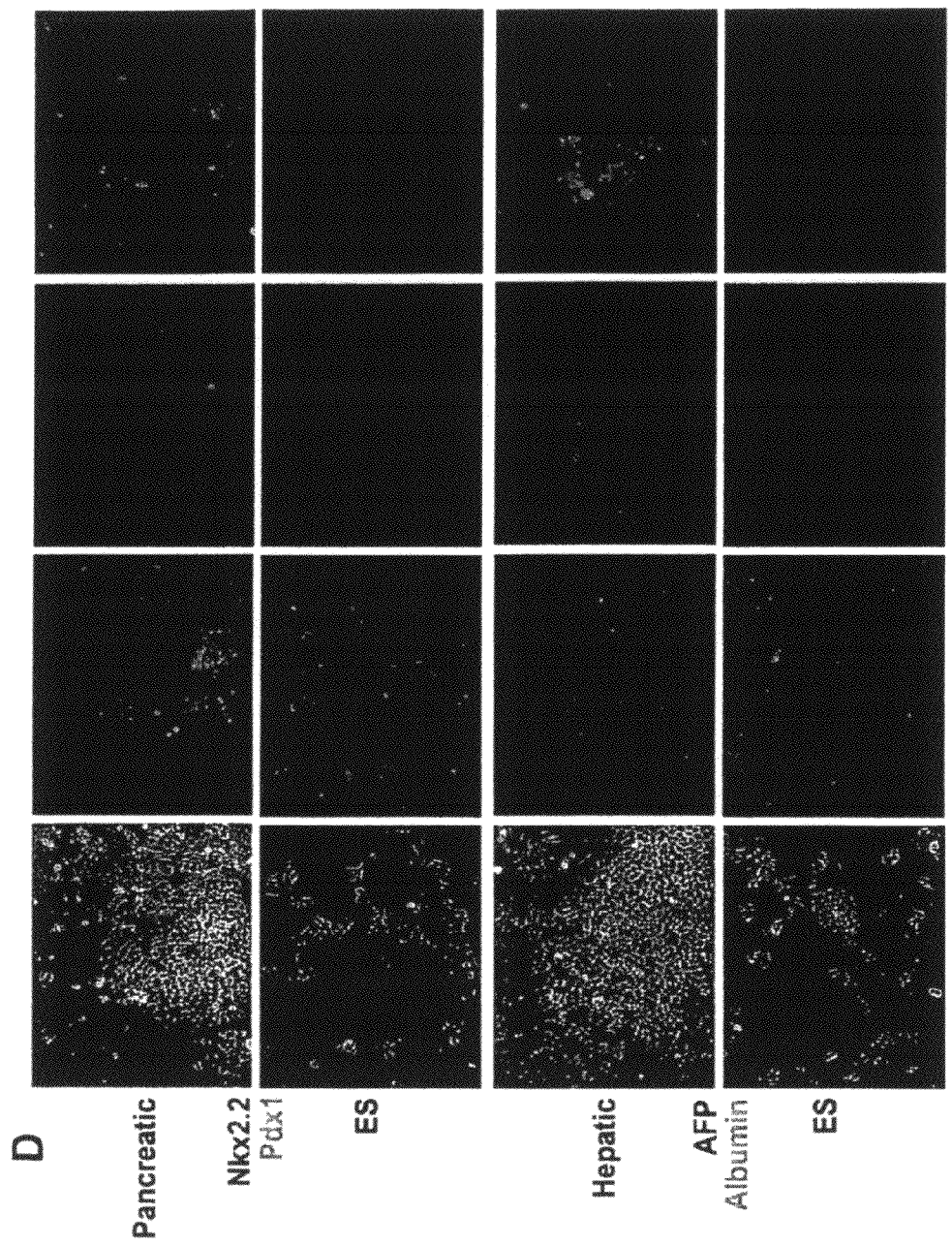

FIG. 21. Expansion of ADE-like progenitors purified from differentiating ES cell culture. (A) Flow cytometry purified fractions from differentiating ES cell cultures plated and grown on gelatin for 12 days. The images are overlays of phase contrast and red fluorescence. Images captured with 10× objective (B) Images of colonies and cells growing in culture from the double positive H+C+ fraction. Images captured using the following objectives: top left 20×, bottom left 10×, top right 20×, bottom right 40×. Passage numbers (P) are as indicated. (C) Immunostaining of H+C+ cells in culture for five passages compared to ES cell controls. Cells were immunostained with anti-Foxa2 (red), anti-Cer1 (green), anti-Oct4 (red) and anti-E-cadherin (green) and nuclei stained with DAPI (blue). (D) Immunostaining of passage 7 H+C+ cultures challenged to further differentiate towards pancreatic or hepatic fates compared to ES cell controls. Top panel; cells were immunostained with anti-Nkx2.2 (red), anti-Pdx 1 (green) and nuclei stained with DAPI (blue). Bottom panel; cells were immunostained with anti-Albumin (green), anti-AFP (red) and nuclei stained with DAPI (blue). All images C-D captured using a 10× objective.

Figure 22:
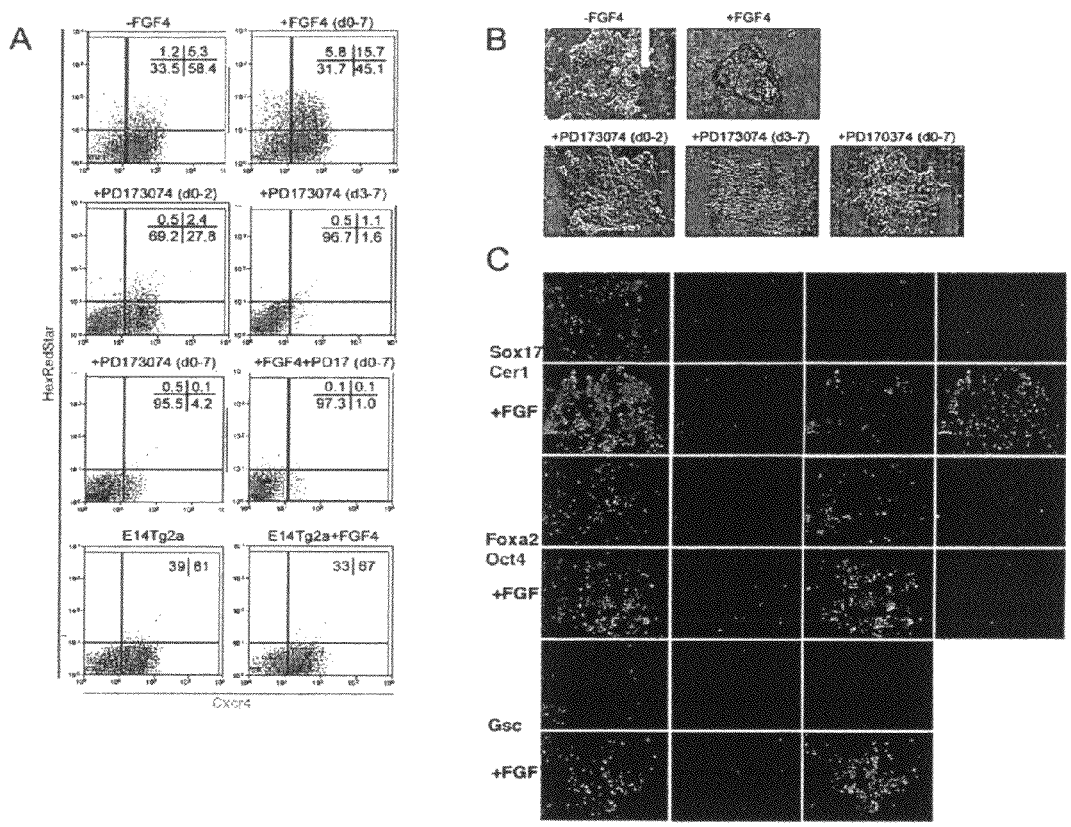
Figure 22:
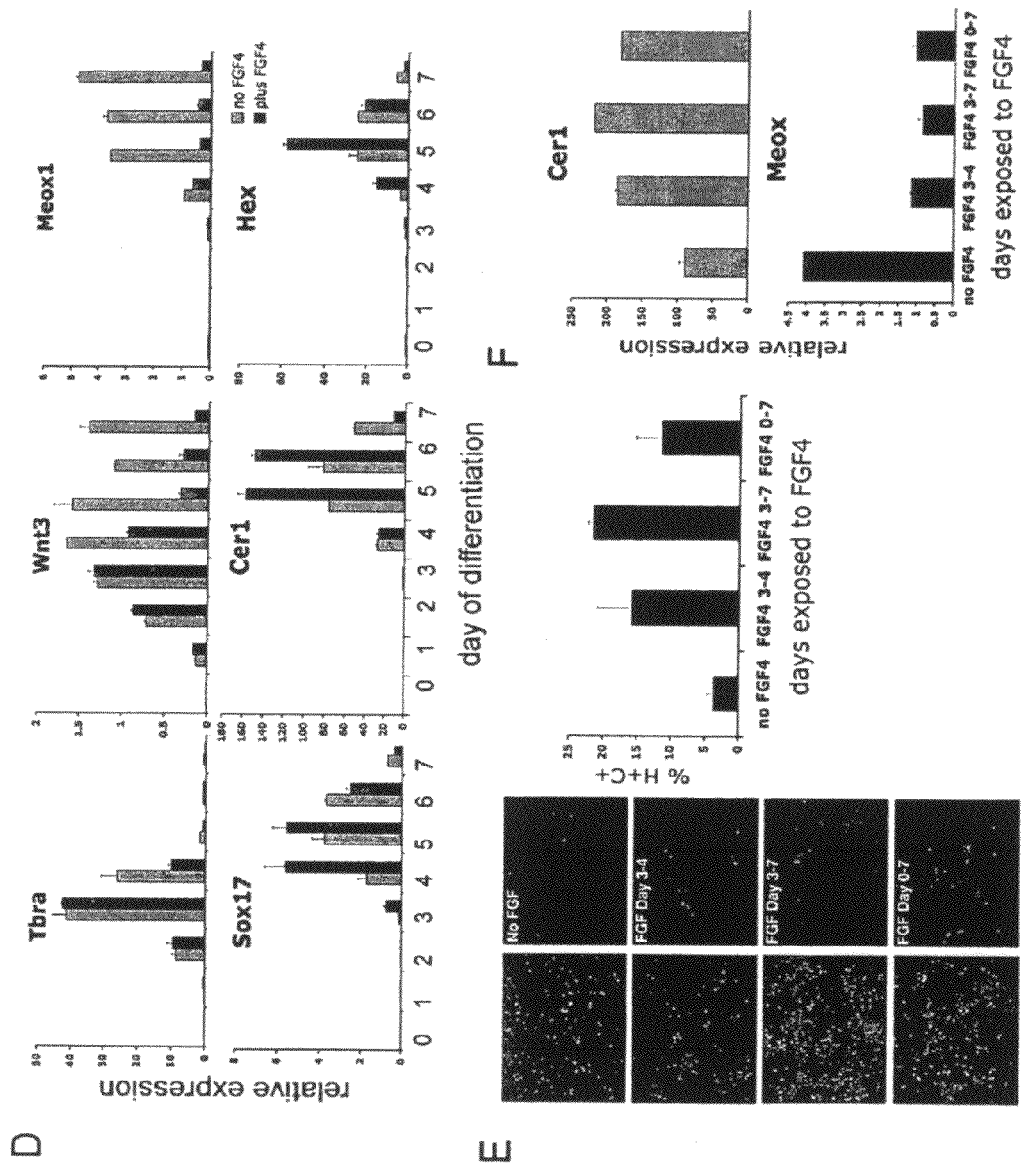

FIG. 22. Defining the requirements for ADE induction in chemically defined serum-free culture conditions reveals a novel requirement for FGF signalling
(A) Flow cytometry of $Hex^{RS}$ and E14Tg2a ES cells differentiated in monolayer culture. All differentiation was carried out in N2B27 plus activin and Bmp4 for two days, followed by four to five days in SF03 plus activin and EGF. FGF4 or the FGF antagonist, PD173074 were added as indicated. Flow cytometry was used to quantitate the size of the H+C+ fraction on day 6. (B) Fluorescence images of cell morphology. Cells were cultured as above with FGF4 or the FGF antagonist PD173074 as indicated. Images captured using a 20× objective on day 6. (C) Immunostaining showing the expression of anterior mesendoderm markers in response to FGF4 in defined monolayer culture. Differentiation was carried out in the presence or absence of FGF4 as indicated by +FGF. Nuclei were stained with DAPI (blue), Cer1 and Oct4 are green, Sox17, Foxa2 and Gsc are red. Images captured using a 10× objective on cultures stained on day 5. (D) Real time quantitative PCR from day 0 to day 7 of serum-free differentiation showing gene expression changes in response to FGF4. The x axis represents the time in days at which the RNA was collected (timepoint 0=ES cells) and the y axis represents relative expression calculated by normalising the transcript number by to the Tata box-binding protein (TBP) transcript number. (E) Time course for FGF addition. Left panel, bright field and fluorescent images of cultures differentiated in monolayer with FGF added for the indicated times. Images captured with a 10× objective on day 6. Right panel, bar graph indicating the percentage H+C+ obtained in these experiments as determined by flow cytometry for the same day. Error bars represent the standard deviation in two independent experiments. (F) Optimal levels of H+C+ induction correlates with peak levels of ADE gene expression (Cer1) and reduced mesodermal gene expression (Meox). Real time quantitative PCR indicating the relative level of transcription of a representative set of markers in response to different periods of exposure to FGF4 in monolayer culture. The x axis represents the time window during differentiation over which cells were exposed to FGF4 and the y axis represents relative expression calculated by normalising the transcript number by to the Tata box-binding protein (TBP) transcript number. RNA was collected at day 6.

Figure 23:
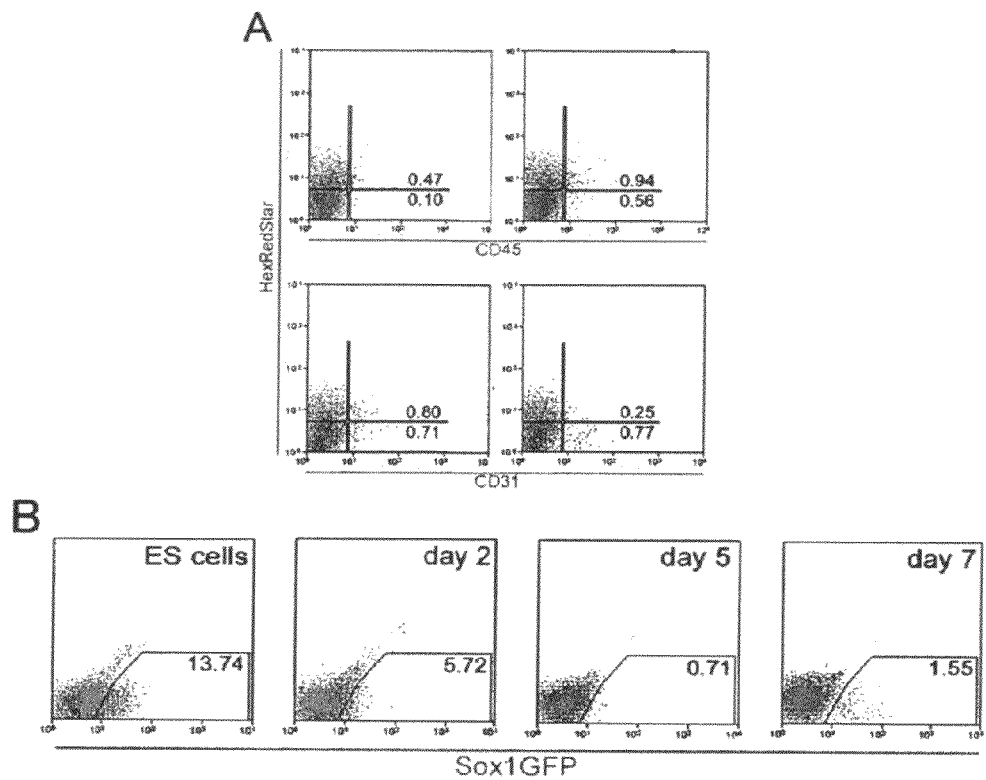

FIG. 23. Activin treated ES cell cultures do not produce haematopoeitic, endothelial or neurectodermal cells. (A) $Hex^{RS}$ ES cells cultured in endoderm inducing conditions for 7 days and sorted for CD45 (haematopoietic) and CD31 (endothelial) expression. (B) $Sox1^{GFP}/+$ ES cells cultured in endoderm inducing conditions for 7 days. The presence of Sox1 positive cells in the ES cell culture is typically encountered when culturing the cells in serum containing media (Stavridis et al., 2007).

Figure 24:
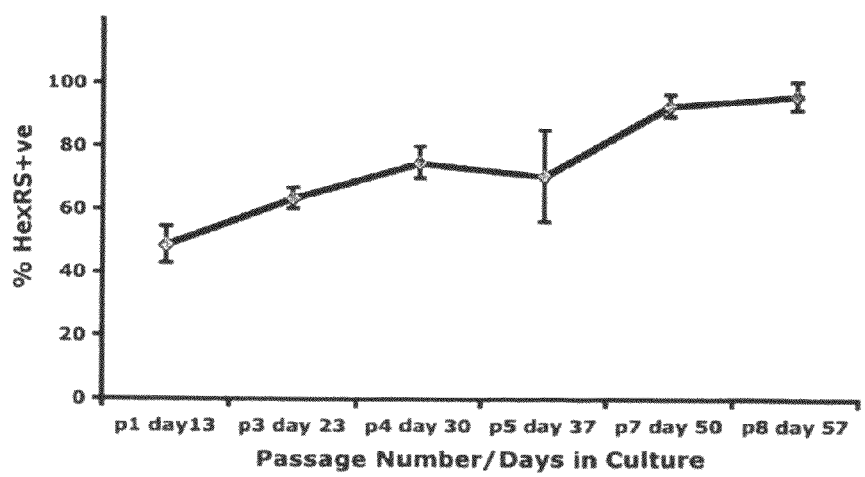

FIG. 24. Quantitation of the number of Hex positive cells, derived from the H+C+ ADE fraction, maintained in culture over multiple passages. The number of $Hex^{RS}$ positive cells was assessed at each passage using fluorescent microscopy and expressed as a percentage of the total number of cells in the culture. The passage number and time point (days) is indicated on the X axis of the graph. Three or four representative fields were counted and the error bars represent the standard deviation between the measurements.

Figure 25:
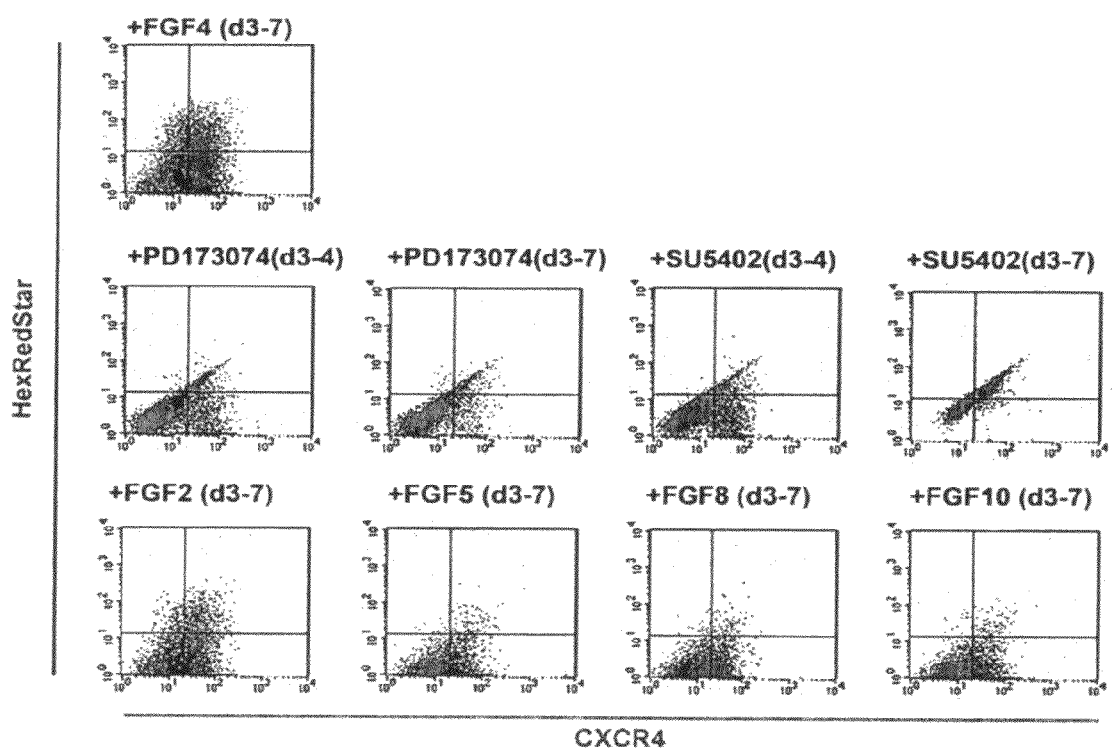

FIG. 25. Treatment of monolayer cultures with FGF2 and FGFR inhibitor SU5402 provide additional evidence that FGF signalling promotes ADE production. Treatment of cultures with different FGFs, suggest that FGF2 and FGF4 but not FGF5, 8b and 10 have the ability to promote ADE formation. Inhibition of ADE by a second FGF receptor inhibitor, SU5402 further supports a requirement for FGF signalling during ADE differentiation. Both PD173074 and SU5402 were added to cultures for days 3-4 or days 3-7 and found to inhibit ADE differentiation. Inhibitors and FGFs are indicated above each graph. In this figure we have not quoted percentages because these inhibitors have induced morphological changes with high levels of autofluorescence indicated by an abundance of cells fluorescing equivalently in both the green and red. Altered morphologies in response to FGF inhibitors can also be observed microscopically (see FIG. 7B) and low (FIG. 7A) to modest (this figure) levels of autofluorescence can be observed when the inhibitors are included from day three of the differentiation protocol.

MATERIALS AND METHODS

Sequences of the oligonucleotides used herein are disclosed in Table 9.
Gene Targeting and Production of $Hex^{RedStar}$ ($Hex^{RS}$) Mouse Line.

Figure 1:
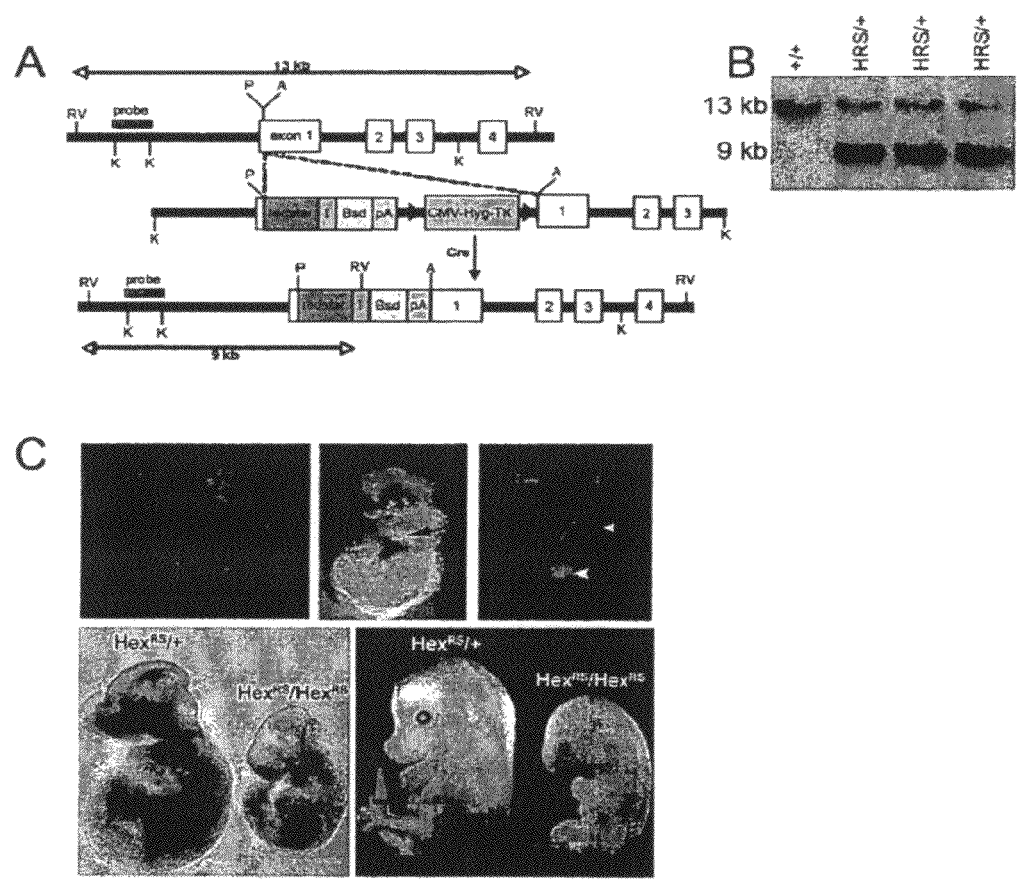
FIG. 1 shows that RS protein recapitulates endogenous Hex expression. (A) Schematic representation of the strategy used for the insertion of the RS coding sequence into the Hex locus. (B) Southern blot indicating the correct insertion of the RedStar cassette into the Hex allele (9 kb band). Targeting frequency=40%. (C) The $Hex^{RS}$ mouse line was generated by blastocyst injection. 4 male chimeras were produced from HRS1 ES cells, all gave germline transmission. Top panel, HexRS/+ and $Hex^{RS}/Hex^{RS}$ embryos at E9.5 and E8. RS expression is visible in the thryoid and liver primordial (white arrowheads) and the ventral foregut (black arrow). Lower panel, HexRS homozygous mutant embryos and HexRS/+ littermates at E9.5 and E15.

The 5' and 3' targeting arms of the targeting construct homologous to the Hex genomic sequence were as described previously (Martinez Barbera et al. 2000) with an Asc1 and Pac1 site engineered downstream of the ATG at the Hex translation initiation site (a gift from Shankar Shrinivas). The RedStar gene was linked via an internal ribosome entry site (IRES) to the gene encoding blasticidin resistance (BSD) followed by a cytomegalovirus promoter-driven hygromycinR-thymidine kinase dual selection cassette flanked by loxP sites. This cassette was fused in frame with the ATG at the Hex translation initiation site via the engineered Asc1 and Pac1 restriction enzyme sites (FIG. 1A). Following electroporation into E14Tg2a ES cells and seven days of selection with hygromycin, resistant clones were selected and expanded. Correctly targeted clones were identified by Southern analysis with a flanking 5'probe (FIG. 1B). Three clones were selected for transient transfection with a Cre recombinase expression vector to remove the selection cassette. Clones that had undergone excision were selected for in the presence of ganciclovir and screened by Southern analysis. Two clones, HRS1-2, were selected for further analysis. The ES cell line HRS1 was injected into blastocysts and passed through the germ line of chimeras to generate the $Hex^{RS}$ mouse line. Mice were maintained on a mixed 129O1a x C57B1/6 background.
Culture and Differentiation of ES Cells.

Mouse ES cells were cultured in serum according to (Li et al. 1995) or serum-free according to (Ying et al. 2003). All ES cells and differentiated cultures were maintained in a 7% $CO_2$-air mixture at 37° C.

ADE was induced under serum-containing conditions using a 2-step protocol. ES cells were seeded onto non-coated 10 cm petri dishes (sterilin) at a density of $5 \times 10^3$ cells/ml in Glasgow minimum essential medium (G-MEM; GIBCO- BRL) supplemented with 10% fetal calf serum (FCS), 0.1 mM nonessential amino acids (GIBCO-BRL), 1 mM sodium pyruvate, 2 mM glutamine and 0.1 mM 2-mercaptoethanol (2ME). Following 2 days of culture the resulting embryoid bodies (EBs) were harvested by centrifugation at 500 rpm for 1 min and replated on 10 cm non-coated petri dishes at the same density in N2B27 culture medium (StemCellSciences) supplemented with 20 ng/ml activin A (R&D). The media was replaced 2 days later and then every 3 days for the duration of the experiment. For some experiments 20 ng/ml EGF, 10 ng/ml Bmp4, 20 ng/ml activin A (R&D), $1 \times 10^{-5}$ M all-trans retinoic acid (Sigma) and 3 µM CHIR99021 (a gift from StemCellSciences) were added to the culture at the indicated timepoints.

For ADE induction under serum-free conditions in suspension culture, ES cells were seeded onto non-coated 10 cm Petri dishes at $5 \times 10^3$ cells/ml in N2B27 culture medium supplemented with 10 ng/ml Bmp4 and 20 ng/ml activin A. Following 2 days of culture the resulting EBs were harvested as above and replated on non-coated Petri dishes at the same density in SF03 culture medium (ref Tada 2005) supplemented with 20 ng/ml activin A and 20 ng/ml EGF. The media was replaced 2 days later and then every 3 days for the duration of the experiment. For some experiments 10 ng/ml Fgf4 (R&D), 10 ng/ml Bmp4, 20 ng/ml Activin A, $1 \times 10^{-5}$ M all-trans retinoic acid, 100 ng/ml PD173074 (Sigma), 20 ng/ml EGF and 3 µM CHIR99021 were added to the culture at the indicated timepoints.

For ADE induction under serum-free conditions in adherent monolayer culture, ES cells were seeded onto gelatin coated 3 cm 6 well dishes (Iwaki) at a density of $1 \times 10^4$ cells/ml in N2B27 medium (StemCellSciences) supplemented with 10 ng/ml Bmp4, 20 ng/ml activin A and 10 ng/ml Fgf4. Following 2 days of culture the media was replaced with SF03 culture medium (Tada 2005) supplemented with 20 ng/ml activin A, 10 ng/ml Fgf4 and 20 ng/ml EGF. The media was replaced 2 days later and then every 3 days for the duration of the experiment. For some experiments $1 \times 10^{-5}$ M all-trans retinoic acid, 100 ng/ml PD173074 and 3 µM CHIR99021 were added to the culture at the indicated timepoints.

For the induction of pancreatic progenitor cells, sorted cell fractions were seeded onto gelatin coated 3 cm 6 well dishes (Iwaki) at $2.5 \times 10^5$ cells/ml in N2B27 media supplemented with 10 ng/ml Fgf4, 2 µM all trans retinoic acid and 0.25 µM KAAD-cyclopamine (Toronto Research Chemicals). Similar results were obtained with $1 \times 10^5$ cells in the absence of KAAK-cyclopmaine. Pdx positive cells appear within 3-5 days of plating onto Gelatin.

For the induction of hepatocytes, we adapted a protocol recently described by Gouon-Evans et al. (Gouon-Evans et al. 2006). Day 7 sorted cell fractions were re-aggregated in N2B27 medium supplemented with 0.5 mM ascorbic acid, $4.5 \times 10^{-4}$ M monothioglycerol (MTG), 50 ng/ml BMP4, 10 ng/ml bFGF (R&D) and 10 ng/ml VEGF (AMS Biotechnology Ltd) at a density of $2.5 \times 10^5$ cells/ml in ultra low cluster 24 well plates (Costar). Aggregates were harvested at 48 hr and replated in N2B27 medium supplemented with 10 ng/ml EGF, 10 ng/ml bFGF, 20 ng/ml HGF (Autogen Bioclear), 20 ng/ml TGF-β (AMS Biotechnology Ltd), 10 ng/ml VEGF and $10^{-7}$ M dexamethasone (Sigma) on gelatin-coated 3 cm tissue culture coated dishes (Nunc). The media was replaced every 3 days for the duration of the experiment.

For the induction of haematopoietic precursors we used a similar protocol to that described by Kennedy and Keller (Kennedy and Keller 2003). Briefly, ES cells were seeded onto non-coated 10 cm petri dishes at a density of $1 \times 10^4$ cells/ml in IMDM (GIBCO-BRL) supplemented with 15% FCS, 2 mM glutamine, 300 µg/ml transferrin (Roche), $4 \times 10^{-4}$ M MTG (Sigma), 50 µg/ml ascorbic acid (Sigma) and the cells analysed at 48 hr and 72 hr.

Flow Cytometry and Cell Sorting.

FITC-conjugated rat anti-CD184 (CXCR4), FITC-conjugated rat anti-CD31 and FITC conjugated rat anti-CD45 were purchased from BD Pharmingen. EBs generated under various different differentiation conditions were dissociated by treatment with cell dissociation buffer (PBS based) (GIBCO-BRL). Cells were washed in PBS supplemented with 10% FCS (FB) and resuspended at a maximum density of $5 \times 10^6$ cells/ml. For surface staining 200 µl of cells were plated in a V shape 96 well polystyrene plate (Sterilin) in PBS supplemented with 1% serum of the species in which the antibody was manufactured. The FITC-conjugated antibody or a FITC-conjugated isotype control was added at a 1:100 dilution. Cells were incubated in the dark for 20 mins, washed 3 times with FB and resuspended in FB supplemented with Topro3-iodide (Invitrogen) to exclude dead cell from the analysis. Cells were analysed using a FACS Calibur (BD Biosciences) or sorted using a MoFlo MLS flow cytometer (DakoCytomation).

Gene Expression Analysis.

Total RNA was prepared from a minimum of $1 \times 10^4$ cells from sorted cell fractions, EBs, monolayer differentiated cells or ES cells using Trizol reagent (Invitrogen). 1 µg of RNA was used as a template for cDNA synthesis using Superscript III (Invitrogen). Real-time RT-PCR was performed using a LightCycler 480 (Roche) and LightCycler 480 SYBR Green 1 Master (Roche). The following cycling conditions were used: denaturation: 95° C. 5 sec, amplification: 95° C. 5 sec, 58° C. 10 sec, 72° C. 20 sec (45 cycles), 81° C. 1 sec, melt: 95° C. 1 sec, 65° C. 10 sec, 95° C. –ramp 5 C per sec continuous, cool: –40° C. 10 sec. Standard curves were generated from plasmid. Samples were normalized to β-actin or TATA-box binding protein (TBP) expression levels. PCR primers and conditions are listed in Table 9.

Immunostaining.

Sorted cells were seeded onto gelatin coated 24 well dishes (Iwaki). Adherence of cells to the substrate was enhanced by centrifugation at 1200 rpm for 3 mins. Sorted cells, monolayer differentiated cells and ES cells were washed in PBS, fixed in 4% paraformaldehyde for 10 mins and permeabilised by washing in PBS supplemented with 0.1% Triton X (PBST). Cells were treated with a blocking reagent (3% serum of same species as secondary antibody, 1% BSA in PBST) for 15 min before incubation with the primary antibody at 4° C. overnight. The cells were washed with PBST and incubated with the appropriate fluorescence-tagged secondary antibody for 2 hr at room temperature. The cells were washed with PBST and DAPI added during the final wash. The following primary antibodies were used, all are anti-mouse: anti-Oct3/4, anti-HNF-3β (Foxa2), anti-HNF-4α (Santa Cruz), anti-Cer11 (R&D), anti-E-cadherin (Takara Bio Inc) anti-alpha fetoprotein (NeoMarkers), anti-albumin (Bethyl laboratories inc). Anti-Pdx1 was a gift from P. Serup.

Kidney Capsule Transplantations.

Cells were sorted at day 7 and approximately $5-10 \times 10^4$ cells of each population were transplanted under the kidney capsule of adult 129 mice. Four to eight weeks after transplantation any live mice were sacrificed and the kidneys removed and fixed in 4% paraformaldehyde (PFA). Following fixation the kidneys were embedded in paraffin wax, sectioned and stained with hematoxylin and eosin and PAS reagent (Sigma).

DNA Microarray Analysis

RNA was prepared from Hex$^{RS}$ ES cells, E14Tg2a ES cells and the four RS/CXCR4 sorted populations of differentiated Hex$^{RS}$ ES cells from three independent experiments. 2 μg was used to prepare a probe for hybridsation to the Illumina Mouse-6-v1 Beadchip. The data was filtered so that any probe with a detection score <0.95 across all samples was removed from the analysis prior to log transformation (base2) and quantile normalisation. Initial inspection of the data suggested the samples clustered loosely according to when they were processed, therefore a model based analysis was used. Differentially expressed probes were identified using LIMMA (Smyth 2004) modeling the sample effect and the date when the samples were processed once grouped. Those with an adjusted B-value >1.0 were deemed differential. Data was also analyzed in a pairwise fashion to determine significant differentiatials between each of the four populations. This was used to produce a molecular signature for the H+C+ double positive population.

Results

Generation of Hex Reporter ES Cells

During embryonic development Hex is expressed in the newly specified ADE cells and therefore represents an ideal early marker for anterior endoderm formation. We created an ES cell line containing the marker gene, RedStar (RS) (Knop et al. 2002) under the control of the Hex locus (FIG. 1A). These cells allowed us to monitor the emergence of newly formed ADE cells during in vitro differentiation. The RS coding sequence was introduced into the first exon of the Hex locus by homologuous recombination in ES cells. The insertion of the RS targeting cassette into this exon terminates the endogenous Hex transcript and should produce a null Hex allele. Correctly targeted clones (FIG. 1B) were transfected with Cre recombinase to remove the selection cassette and two independent clones with normal karotype, HexRedStar (Hex$^{RS}$) 1-2, were selected for further analysis.

To confirm that the RS protein accurately reflects endogenous Hex expression, Hex$^{RS}$1 ES cells were used to generate a Hex$^{RS}$ mouse line. Embryos from Hex$^{RS/+}$ intercrosses are shown in FIG. 1C. At E8.5 red fluorescence was detected in the foregut and by E9.5 was present in the liver and thyroid primordia and weakly expressed in the intersomitic blood vessels. Thus, RS protein reflects the expression of endogenous Hex protein as reported by Thomas et al, (Thomas et al. 1998). No live Hex$^{RS}$/Hex$^{RS}$ mice were born (Table 1) and Hex$^{RS}$/Hex$^{RS}$ embryos exhibited anterior defects and reduced hepatic tissue mass (FIG. 1C). This phenotype is consistent with the Hex null phenotype (Martinez Barbera et al. 2000) and confirms the loss of the endogenous Hex transcript from the targeted Hex$^{RS}$ allele. Moreover, no phenotype was detected in Hex$^{RS/+}$ embryos or mice (FIG. 1C, Table 1), indicating that any reduced Hex dosage in heterozygous cells will not impact on the ability of the cells to form ADE in vitro.

Expression of the HexRedStar Reporter During ES Cell Differentiation.

Figure 2:
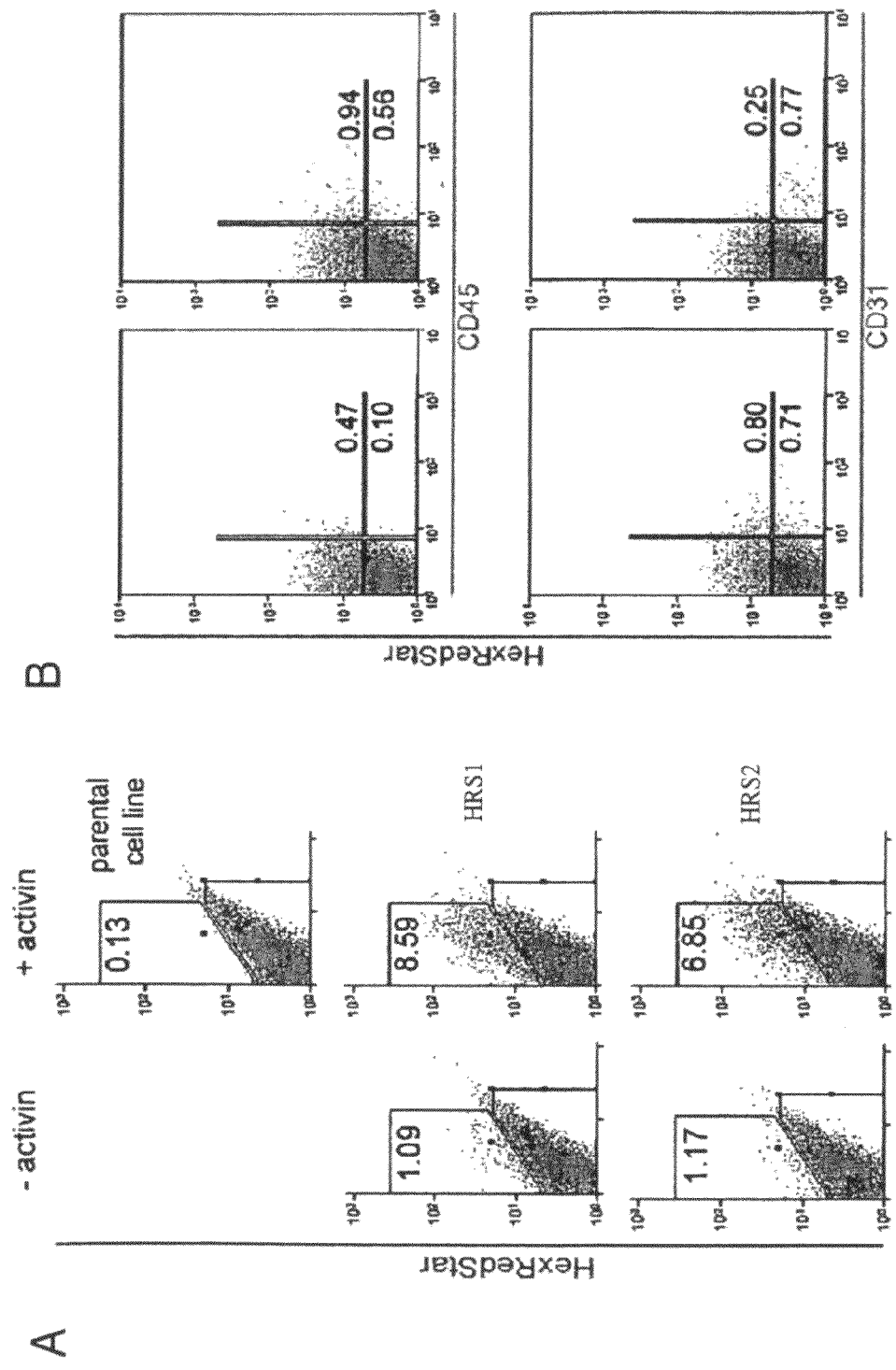
FIG. 2 shows In vitro expression of RS is specific to Hex expressing cell lineages. (A) HRS and E14Tg2a (parental) ES cells cultured in serum containing media for 2 days followed by N2B27 plus or minus activin for 5 days. Percentages of RS expressing cells are indicated. (B) HRS ES cells cultured in endoderm inducing conditions for 7 days and sorted for CD45 (haematopoietic) and CD31 (endothelial) expression. (C) Sox $1^{GFP}$/+ES cells cultured in endoderm inducing conditions for 7 days. The presence of sox 1 positive cells in the ES cell culture is typically encountered when culturing the cells in serum containing media (ref or personal communication?) (D) HRS and E14Tg2a (parental) ES cells cultured in early haematopoietic progenitor inducing conditions. Percentages of RS expressing cells are indicated. (E) Semiquantitative RT-PCR for a range of markers associated with endoderm (Sox17, Cerl1 . Ecadherin, Gata4), mesoderm (Tbra, Mixl1, Meoxl. Gata1), ectoderm (Zic1) and parietal endoderm (Sox7) on RS positive and RS negative cell fractions sorted by flow cytometry. Samples were first analysed by quantitative RT-PCR for B-actin expression and normalised accordingly.
Figure 2:
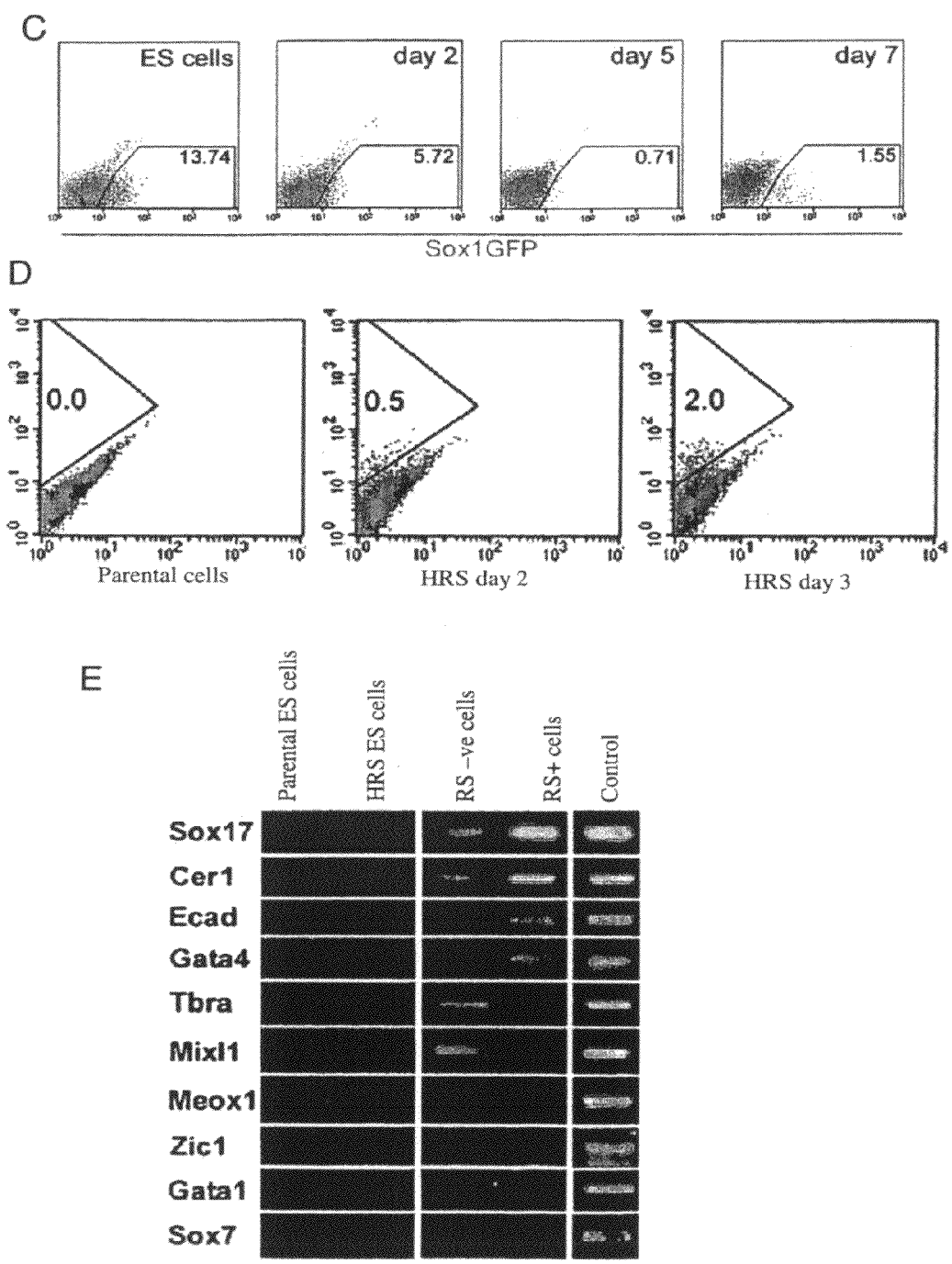

The secreted TGFβ ligand activin, has previously been shown to induce markers of endoderm in Xenopus animal cap assays (reviewed by (Okabayashi and Asashima 2003)) and to induce a mesendodermal cell population from ES cells in culture (Kubo et al. 2004; Tada et al. 2005). In these early embryonic tissues, activin can induce the same spectrum of mesendodermal gene expression as the endogenous inducer, Nodal. To test the ability of activin to induce Hex$^{RS}$ expression, ES cells were differentiated in a two-step aggregation culture system in serum containing media for 48 hr followed by serum free media supplemented with activin for 5 days. Under these conditions, 6.8-8.6% of cells were RS positive at day 7 (FIG. 2A). This induction was shown to be dependent upon activin treatment and was consistent in two independently derived Hex$^{RS}$ ES cell lines (FIG. 2A).

Hex expression in the developing embryo is not exclusive to endodermally derived cells since it is also expressed in a specific mesodermal cell population that may represent a bipotent haematopoietic and endothelial precursor often termed a haemangioblast (Kubo et al. 2005). In developing embryos Hex is also expressed in angioblastic and endothelial precursor populations in the dorsal aorta, in intersomitic vessels and the visceral yolk sac and later in the endocaridium of the heart (Thomas et al. 1998; Rodriguez et al. 2001). To ensure that the activin induced HexRS positive cells do not represent these cell populations we analysed the differentiated cells by flow cytometry for the presence of endothelial and haematopoietic markers. FIG. 2B shows that our activin treated cell cultures do not contain significant numbers of endothelial (CD31 positive) or haematopoietic (CD45 positive) cells. In addition, a Sox-1 GFP reporter ES cell line was used to demonstrate the absence of neurectodermal cell types during our activin induced differentiation protocol (FIG. 2C).

Despite the absence of haematopoetic precursors in these activin treated cultures, it was important to confirm that Hex$^{RS}$ ES cells could give a reliable read out of haematopoetic differentiation in vitro. Using culture conditions tailored towards the specific induction of early haemopoietic cell populations (Kubo et al. 2005) we see a modest but significant induction of RS positive cells at day 3 (FIG. 2D) whereas under our endodermal differentiation conditions, significant numbers of RS+ cells were not detected until day 6 (see FIG. 3A).

In summary, our analysis of multiple cell lineages indicates that activin induced Hex$^{RS}$ positive cells represents endoderm. This was confirmed by profiling the flow cytometry purified RS positive cell population by RT-PCR (FIG. 2E).

Purification of ADE from Differentiating ES Cells

Figure 3:
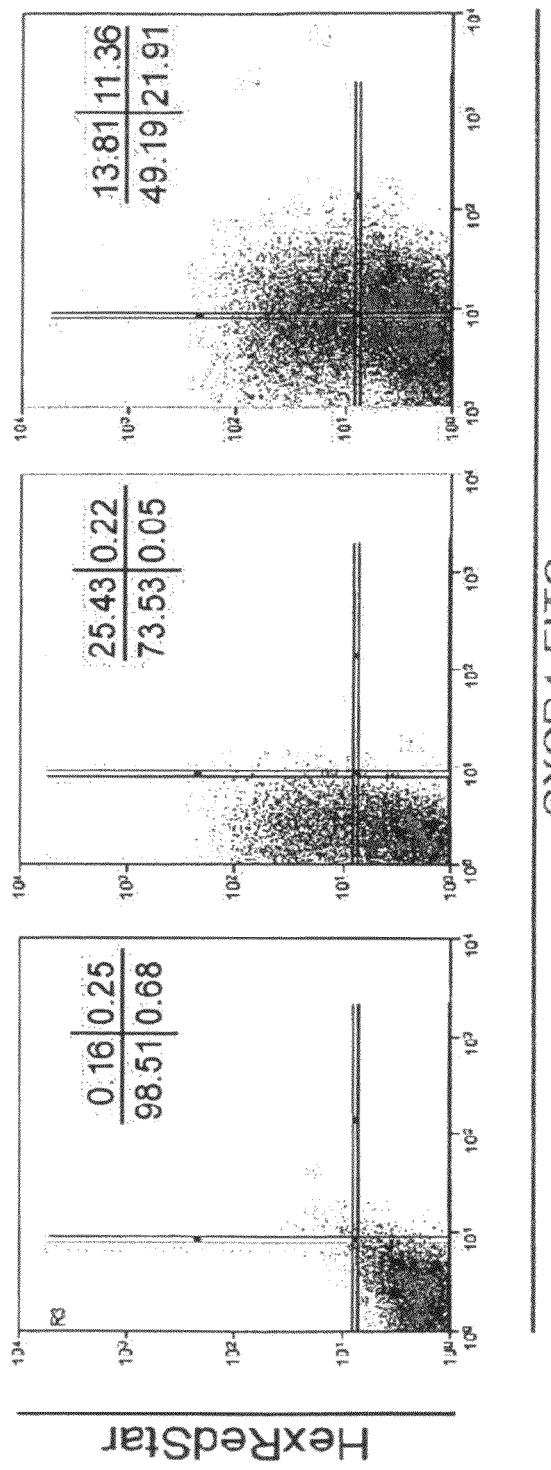
FIG. 3 shows that Activin and EGF induce H+C+ cells following culture in serum containing media.

In addition to being a marker of early ADE specification, Hex is also expressed in the extra-embryonic primitive and visceral endoderm lineages. In particular, Hex is expressed in a visceral endoderm population known to have similar signalling properties to the ADE, the anterior visceral endoderm (AVE) (Thomas and Beddington 1996; Beddington and Robertson 1998). Unlike ADE which contributes to the foregut, AVE will contribute predominately to the visceral yolk sac (Lawson and Pedersen 1987). At the level of marker gene expression, the AVE is very difficult to distinguish from the ADE. While expression levels of the visceral endoderm associated gene Sox7, was low during our differentiation protocol (FIG. 2E), this marker is not expressed in the AVE region of the visceral endoderm in vivo. To confirm that the Hex$^{RS}$ positive population was ADE rather than AVE, we used expression of a second marker, the chemokine receptor Cxcr4. Cxcr4 is expressed in definitive mesoderm and endoderm populations, but excluded from all yolk sac visceral endoderm (McGrath et al. 1999; Yusuf et al. 2005). We used flow cytometry to analyze a Cxcr4, RS double positive cell population we believed was putative ADE (FIG. 3). Quantification of this population enabled us to determine media conditions optimal for the production of this putative ADE population of RS/Cxcr4 double positive (H+C+) cells. Table 2 summarises the different culture conditions tested. Optimal H+C+ induction was obtained with ES cells in suspension culture for two days in the presence of serum and then an additional five days serum free in the presence of activin and EGF. This culture condition was the one used for the induction of ADE with the exception of the serum-free experiments. Optimal induction conditions were also sensitive to cell density (Table 3).

During the ADE optimisation process we also observed that the addition of Bmp4 and retinoic acid (either at day 0 or day 3) completely blocked the induction of the RS positive population (Table 2), without effecting CXCR4 induction (data not shown). This suggests that the induction of ADE from non-committed precursors is particularly sensitive to manipulation of these signalling pathways. Thus these pathways either block the progression of mesendodermal progenitors toward ADE or shift the differentiation of these progenitors towards more posterior or mesodermal lineages. Interestingly, both BMPs and retinoic acid have been shown to posteriorize anterior endoderm (Kumar et al. 2003) and thus may be acting during differentiation to modify the regional identity of these cultures.

We were surprised by the inability of a Wnt agonist, CHIR99021(Bennett et al. 2002) to stimulate the induction of significant H+C+ populations. To the contrary, addition of CHIR99021 at day 0-2 completely blocked the induction of the H+C+ cell population. While these observations may be relevant to lineage specification in the anterior endoderm, it is hard to resolve the effects of specific signalling angonists and antagonists in the presence of serum.

Molecular Analysis of ADE Derived from ES Cells

To date, no markers have been identified that are exclusively expressed in the ADE. Therefore, in order to be confident that our cultures were producing ADE we characterised differentiating populations of $Hex^{RS}$ ES cells using a comprehensive range of markers and techniques.

To assess whether our cell cultures produce a gene expression dynamic similar to that observed during ADE induction in the gastrulating embryo we examined the kinetics of gene expression from day 0-7 of the differentiation process. Markers associated with ES cells, early epiblast, the primitive streak, ectoderm, mesoderm and endoderm were examined by quantitative real-time PCR (FIG. 4A). As in the mouse epiblast, Oct4 (Pou5f1), Nodal and E-cadherin are expressed at high levels in ES cells. Significant levels of all three of these markers are maintained during the early phase of ES cell differentiation and they are then rapidly down regulated. Both Nodal (Norris et al. 2002) and Oct4 (Perea-Gomez et al. 1999) expression are maintained during epiblast development and become restricted to the posterior epiblast region surrounding the primitive streak. Interestingly the expression of these early markers was maintained alongside the peak expression of early primitive streak markers (Wnt3a, Brachyury (reviewed in (Beddington and Robertson 1999)). Early during primitive streak formation node-associated markers such as Mixer like 1 (Mix11) Goosecoid (Gsc) and FoxA2 are expressed, first through out the streak region and then in the prospective axial mesendoderm (notochord, prechordal plate and ADE) (Robb et al. 2000; Kinder et al. 2001). Similarly, our cultures expressed these markers and Cxcr4 beginning at day 3, the peak of Wnt3a and Brachyury (Tbra) expression, and peaking from day 5-6. During gastrulation, the first discrete ADE markers appear in cells at the anterior end of the primitive streak and are then are maintained in those cells as they migrate forward along the midline (Kinder et al. 2001). These region or lineage specific genes, such as Cerberus 1 homologue (Cer1), Hex and Sox17 appeared between days 5-7 in our cultures.

Although Mix11 and Wnt signalling, are required for endoderm induction, (Hart et al. 2002) ((Lickert et al. 2002) Wnt3 and Mix11 are not expressed in definitive endoderm. In our culture conditions these markers are significantly expressed from day 3-5 and are then down regulated concordant with the emergence of markers of endoderm such as Sox17, Cer1 and Hex.

Based on the expression of these gastrulation stage markers, the dynamic pattern of expression evident in our differentiating ES cell cultures reflects the progression of markers during ADE specification in embryos. Similarly, FIGS. 4B and C show that both RS fluoresence and CXCR4 protein were produced several days after activin treatment and that CXCR4 production precedes Hex. This is consistent with the expression of these markers in vivo (McGrath et al. 1999; Yasunaga et al. 2005; Yusuf et al. 2005) and suggests that the Cxcr4 single positive population may represent non-committed mesendoderm, whereas the H+C+ population is committed ADE.

The sequential expression of a number of markers observed in FIG. 4A appears inconsistent with differentiation towards the visceral endoderm population that expresses Hex, AVE. During embryogenesis Hex expression in the AVE proceeds Brachyury by at least one day (Thomas et al. 1998) and this is the opposite of what we observe. While Gsc and Cer1 are expressed in the AVE, Hex expression throughout the primitive endoderm precedes the induction of these markers ((Thomas et al. 1997; Thomas et al. 1998) and Brickman and Beddington, unpublished observations). Finally, while Sox17 is expressed in the visceral endoderm, it is not expressed alongside Hex in the AVE (Kanai-Azuma et al. 2002), whereas Sox17 is expressed during ADE induction and is expressed with similar kinetics to Hex during differentiation. ADE identity is therefore also consistent with the expression of Sox17 in the H+C+ population (see FIG. 5A). The parietal endoderm marker, Sox7 was barely detectable by Q-PCR during the differentiation process and therefore not considered to be significantly expressed (see FIG. 9). We conclude that our H+C+ populations represent ADE.

We found the majority of committed cells generated using our protocol appear to be endoderm rather than mesoderm. E-cadherin is expressed in ES cells and in the preimplantation stage embryo. Cells destined to become mesoderm lose E-cadherin expression at the gastrulation stage whereas cells destined to become endoderm remain E-cadherin positive. E-cadherin expression can therefore be used to distinguish mesoderm cells from ectoderm and endoderm (Huber et al. 1996). We found E-cadherin to be expressed at significant levels during the late stages of the differentiation protocol, indicating that this protocol did not favour the production of mesoderm. Immunostaining confirmed that the majority of cells in the day 7 cultures were E-cadherin positive (see FIG. 5B).

To better understand the spectrum of cell types produced in our ES cell differentiation protocol and gain a more comprehensive picture of the H+C+ cells, $Hex^{RS}$ cultures were sorted into four populations based on RS and CXCR4 protein levels and profiled by quantitative RT-PCR, immunostaining and microarray. Surprisingly we found that the transcript level of Hex in the RShigh/CXCR4low (H+C−) and RSlow/CXCR4high (H−C+) populations were very similar and significantly less than the RShigh/CXCR4high (H+C+) population (FIG. 5A). This may reflect the time lag between the production of Hex transcript and mature RS protein. Thus the H+C− cell population which appears to be formed from the H+C+ population (FIG. 4B) is likely to consist of cells in which CXCR4 has been switched off and Hex is also being downregulated at the transcript level, but the RS protein is still present. Similarly, the H−C+ cell population may contain cells in which Hex transcripts have begun to be produced but not the RS protein. Such a large difference between protein and transcript level was not observed for CXCR4 and may reflect the shorter maturity rate and half-life of the CXCR4 protein. The transcript level of both Hex and CXCR4 was highest in the H+C+ sorted population and allows us to be confident that the H+C+ sorted population is positive for both the Hex transcript and protein.

The H+C+ cell population expressed the highest levels of E-cadherin, Cxcr4, Cer1 and Hex transcript (FIG. 5A). All of these genes are expressed in the anterior definitive endoderm. Importantly, the expression of markers Tbra, Wnt3 and Mix11 that are associated with the early primitive streak but not the anterior definitive endoderm, were lowest in the H+C+ population as was the paraxial mesoderm marker Meox1. Cdx2 is also expressed in the early primitive streak cell population (Beck et al. 1995) and is then restricted to the posterior endoderm. Both Cdx2 and the parietal endoderm marker Sox7 were only detected at very low levels during differentiation and were expressed at the lowest level in the H+C+ cell population (FIG. 5A).

We performed immunostaining to analyse marker expression at the single cell level. In accordance with the PCR data we found almost all of the H+C+ cells to express the anterior definitive endoderm marker Cer1, and the definitive endoderm markers Foxa2 and E-cadherin but not the ES cell marker Oct4 (FIG. 5B).

Microarray analysis was performed on Illumina Mouse-6-v1 Beadchip. Three chips were used for each of the four differentiated populations and Hex$^{RS}$ and wild type E14Tg2a ES cells. Initial inspection of the data suggested the differentiated samples cluster close to each other as do the two ES cell lines (FIG. 6B). The close proximity of the two ES cell lines indicates there is little difference in gene expression in Hex$^{RS}$ heterozygote and wild-type ES cells. Of the differentiated populations, the H+C+ population is most closely related to the H−C+ population, consistent with the view that the H+C+ ADE arises from the H−C+ mesendodermal population. Differentially expressed genes were identified using LIMMA (Smyth 2004) modeling the sample effect and the date when the samples were processed once grouped. Those with an adjusted B-value >1.0 were deemed differential. Clustering of these differentials is shown in FIG. 6A. Interestingly, the H+C+ population is enriched for a number of anterior endoderm markers such as Frizled 5 (Finley et al. 2003), Cer1 (confirming the data in FIG. 5), Lim1 (Shawlot and Behringer 1995) and FoxA2/FoxA3 (Friedman and Kaestner 2006). We conclude from this data that the H+C+ population is axial mesodendoderm that is enriched for the expression of anterior markers, normally expressed in the ADE. FIG. 6C shows qRT-PCR validation on the expression of these genes and a number of novel transcripts and potential new ADE markers.

ES Cell Derived ADE has Increased Potential to form Pancreatic Progenitors and Hepatocytes.

To examine the potential of the sorted cell populations to differentiate further down the endodermal lineage, we cultured the cell fractions in conditions conducive for the formation of foregut, pancreatic and liver progenitors. During gut tube formation, the ADE loops around and migrates in a posterior direction to form the ventral foregut. Thus the anterior most component of the definitive endoderm ends up in a more posterior location that gives rise to liver and pancreas. The pancreas is formed by two budding outgrowths from this region of foregut and their induction and the subsequent specification of pancreatic progenitors is dependent on interactions with the surrounding tissues. In explants and grafting experiments, posterior mesoderm and signalling molecules associated with it (BMP, FGF and RA) can induce more posterior, pancreatic identity, on the anterior end of the gut tube (Wells and Melton 2000; Kumar et al. 2003). One of the earliest markers of emerging pancreatic buds is the transcription factor Pdx1(Offield et al. 1996). Induction of Pdx1 and formation of the dorsal pancreatic bud also requires inhibition of sonic hedgehog (Hebrok et al. 1998).

We attempted to differentiate our ES cell derived ADE to pancreatic progenitors using retinoic acid, FGF4 and the sonic hedgehog inhibitor cyclopamine. After 5 days in culture we could detect Pdx 1 positive cells in the H+C+ sorted cell fraction (FIG. 6A). Pdx1 positive cells were also present in the H−C+ and H−C− cells, however both the intensity of Pdx1 staining and the number of positive cell clusters was lower than for the H+C+ cells (FIG. 6A and Figure legend). The ability of H−C+ populations to form Pdx1 positive pancreatic progenitors with reduced efficiency may reflect the ability of putative non-committed mesendoderm to generate ADE upon further culture. Undifferentiated ES cells did not generate any Pdx1 positive cells (data not shown). We were unable to culture H+C− cells in this culture condition and it is possible that these cells have become more restricted in their differentiation potential. Interestingly Hex expression does persist in the ventral foregut that will give rise to the liver primoidium and thyroid (Thomas et al. 1998) and it is possible that these cells have progressed further towards one of these lineages and can no longer generate Pdx1 positive pancreatic progenitors.

Since both the pancreas and the liver are derived from ADE we would predict that our H+C+ ADE cells would also be capable of generating hepatocytes. Using a method adapted from Gouon-Evans et al (Gouon-Evans et al. 2006), day 7 H/C sorted cell fractions were cultured in hepatocyte differentiation conditions for 5-13 days (total culture period 12-20 days). Hex is expressed in the liver primordial at E9 ((Thomas et al. 1998) and FIG. 1B) therefore we would expect to see RS protein in cells forming hepatocytes. RS positive cells were present at day 9 of the total culture period in aggregates formed from the H+C+ and H+C− sorted cells only (FIG. 6B). While some AFP positive hepatocytes were observed at day 12 in the H−C+ and H−C− cell populations the efficiency of differentiation was always lower. No AFP positive hepatocytes were formed from non-induced ES cells cultured in the same conditions (data not shown). At day 12, AFP positive hepatocytes could be detected in all four cultured cell fractions, however the number of positive cells was highest in the H+C+ cell fraction (FIG. 6C). By day 20, AFP expression was reduced and the number of albumen positive cells had increased significantly in the H+C+ population (FIG. 6D).

To evaluate the level of commitment established by cells in each fraction, the cultures were sorted into the four RS/CXCR4 fractions following 7 days of differentiation, and immediately transplanted under the kidney capsule of adult 129 mice. Eight weeks after transplantation the mice were sacrificed and the grafts analysed. From the nine H+C+ transplants performed only one small growth was observed. In contrast 5 large teratomas were observed from the transplanted H−C− cells, most likely due to the presence of low numbers of ES cells within this cell fraction (see FIG. 4B). The H+C− and H−C+ transplants resulted in 3 and 4 growths respectively (Table 4). The small H+C+ growth contained endodermal derivatives indicated by the presence of ductal epithelial structures containing PAS positive secretory granules (FIG. 6E). Similar epithelial structures were observed in the H+C− and H−C+ grafts. Interestingly, the H−C+ transplants were the only ones (excluding the H−C− teratomas) that contained cartilage (FIG. 6E). The appearance of both mesoderm and endoderm in these grafts suggest that H−C+ fraction contains non-committed mesendodermal progenitors.

Differentiation Potential of ES Cell Derived ADE.

Since both pancreas and liver arise from ADE, we tested the hepatic potential of the H+C+ population using a method adapted from Gouon-Evans et al., (2006), which involves upto 13 additional days of hepatocyte differentiation (total culture period 20 days). By day 12, AFP positive hepatoblasts were apparent in the H+C+ cell fraction and while some AFP expression was observed in all four fractions, it was significantly higher in the double positive fraction (FIG. 11C). No AFP positive cells were formed from non-induced ES cells cultured in the same conditions (data not shown). This trend was already apparent at the RNA level from day 9, where the H+C+ fraction expressed at least 3-4 fold higher levels of Krt19, Albumin, AFP, Hnf6 and Foxa2 transcript than any of the other fractions (FIG. 11B). The pattern of Hex expression during the differentiation period is also consistent with its later expression in the liver primordia (Thomas et al., (1998) and FIG. 1C) with RS protein detected at day 9 in forming hepatocytes but only in the H+C+ and weakly in H+C− sorted cells (FIG. 11B). Flow cytometry at this stage of differentiation also supports the quantitative capacity of the H+C+ fraction to differentiate towards liver, as 62% of the H+C+ cess are Hex positive forming hepatocytes, whereas only 11% of the H−C+ population were weakly fluorescent (FIG. 11A). By day 20, AFP expression was reduced and the number of albumin positive cells had increased significantly in the H+C+ population reflecting the maturation of hepatoblasts to hepatocytes (FIG. 11D). At this stage, Albumin expression was not detected in the other fractions (data not shown). On the contrary, under these conditions large numbers of cardiomyocytes were observed in H−C+ and double negative fractions (FIG. 11E). Taken together these results suggest H+C+ fraction contains lineage restricted endodermal progenitors.

To examine the pancreatic potential of the sorted cell populations we cultured them with cytokines implicated in pancreatic specification (Hebrok et al., 1998; Kumar et al., 2003); retinoic acid, FGF4 and the sonic hedgehog inhibitor cyclopamine. H+C+ sorted cells generated clusters expressing markers of the emerging pancreatic buds, Pdx1 and Hnf4α with the highest efficiency, indicating their pancreatic differentiation potential in vitro (FIG. 11). In contrast H+C− fractions did not give rise to co-expressing clusters. Limited activity (2 and 9-fold reduced cluster number respectively and reduced staining intensity) was detected from the H−C+ and H−C− fractions (FIG. 11F), presumable reflecting the ability of non-committed cells to generate ADE upon further culture. Using undifferentiated ES cells as a starting population from this 5 day protocol did not generate any Pdx1 or Hnf4α positive cells (data not shown). When this was repeated with FGFIO (D'Amour et al., 2006) in place of FGF4, we obtained a similar (3-fold) quantitative enhancement in cluster formation in the H+C+ fraction (data not shown).

To evaluate the in vivo potency exhibited by cells in each H/C fraction following 7 days of differentiation they were sorted and immediately transplanted under the kidney capsule of adult mice. Nine transplants were performed for each sorted fraction. The H−C− transplants gave rise to large teratomas (5 out of 9) indicating this fraction still contains ES cells. In contrast, no teratomas were generated from the H+C+ transplants. The H+C+ cells in one animal gave rise to a small growth that contained endodermal derivatives indicated by the presence of ductal epithelial structures containing PAS positive secretory granules (FIG. 11E). Similar epithelial structures were observed in the growths from the H−C+ grafts (4 out of 9) and H+C− grafts (3 out of 9). The H−C+ transplants were the only ones (excluding the H−C− teratomas) that contained cartilage (FIG. 11E), consistent with the notion that this fraction still contains cells competent to generate both mesoderm and endoderm.

Expansion Potential of ES Cell Derived ADE.

During the early phase of further ADE differentiation we noticed that purified H+C+ ADE proliferated in the presence of FGF2, BMP4 and VEGF. To test whether these conditions could be used to expand H+C+ ADE progenitors we plated FACS purified fractions in defined media incorporating these cytokines. Initially all four population were able to grow, but only the H+C+ fraction contained significant numbers of Hex positive cells (FIG. 12A). While, these cultures were not homogenous, the H+C+ fractions were able to give rise to new Hex positive colonies upon repeated passaging (FIG. 12B). The remaining three fractions were unable to survive four passages. The percentage of Hex positive cells in these cultures expanded over time, reacting as high as 96%. All four populations were seeded at approximately 10% confluence and the growth of the red population observed over time. Initially all four population were able to grow, but only the H+C+ fraction contained significant numbers of Hex positive cells (FIG. 6A). While these cultures were not homogeneous, the H+C+ fractions were able to give rise to Hex positive colonies upon repeated passaging (FIG. 6B) and the percentage of Hex positive cells in these cultures expanded over time, reaching as high as 96%.

To confirm the identity of cultures H+C+ cells, we examined the expression of the endoderm markers FoxA2, and E-cadherin, the ADE marker Cerberus and ES cell marker Oct4 at passage 6. Indeed the vast majority of these cultures expressed Cerberus, FoxA2 and E cadherin, but not Oct4 (FIG. 12C), indicating these cells represent a form of proliferating ADE progenitor. We also tested the ability of these cultures to further differentiate towards hepatic and pancreatic cell types. Passage 7 ADE cultures were differentiated as described above. Pancreatic differentiation produced clusters of Nkx2.2 and Pdx 1 expression cells (FIG. 12D) whereas hepatic differentiation resulted in field of cells with the morphology of immature hepatocytes expressing both AFP and albumin (FIG. 12D).

Defined Conditions for ADE Induction Suggest Novel Roles for FGF and BMP Signalling.

The ability of H+C+ ADE to recapitulate foregut development in vivo and in vitro encouraged us to define the conditions required for the specification of this ADE population in vitro. In the presence of serum, H+C+ cells can only be derived in a multicellular aggregation suspension system (embryoid body). An adherent monolayer culture system would greatly improve our ability to investigate lineage specification in vitro. We therefore investigated whether it was possible to differentiate $Hex^{RS}$ ES cells to ADE under defined conditions in both multicellular aggregation and a monolayer culture system.

As anterior endoderm specification in vivo occurs during a series of complex morphogenetic movements, it is possible that differentiation cannot be uncoupled from the multicellular interactions present within an embryoid body. Mesendoderm induction has been reported using the serum-free media SF03 in an adherent monolayer culture system (Tada et al. 2005). However, these cultures appear to express significant levels of mesodermal marker genes and have no established positional identity. Moroever, the extent to which these cultures can be differentiated further towards specific endodermal lineages is not clear.

Our attempts to culture Hex$^{RS}$ cells in SF03 and activin, both as aggregates and in monolayer, resulted in cell death (Table 5,6). A very low percentage of live cells could be obtained in monolayer with SF03 by increasing the plating density and adding Bmp4 and EGF to the media, however, the very low cell yield obtained with this adapted SF03 protocol did not make it a viable option for in vitro culture of ADE (data not shown).

Our previous experiments showed that switching to N2B27 serum-free media following serum induced the highest percentage of ADE (Table 2, FIG. 3A). We therefore tried N2B27 media, in combination with various growth factors, for the entire differentiation process. In both suspension and monolayer systems, culturing with N2B27 resulted in no induction of Hex at day 7 (Table 5,6). Changing the insulin content of the N2B27 media and the plating density of the starting culture did not alter this result (data not shown).

Following extensive optimisation, we found that a significant H+C+ cell population could be induced in both suspension culture and monolayer following a two-step serum-free differentiation protocol. Cells cultured in N2B27 plus Bmp4 for 2 days and then switched to SF03 plus activin and EGF for 5 days resulted in an average H+C+ induction of 13.3% and 5.7% in suspension and monolayer culture respectively. Interestingly, we found that adding either BMP4 or the Wnt signalling agonist, CHIR99021 during the first two days of differentiation significantly increased the total number of surviving cells at the end of the 7 day differentiation process (Table 7). Activin had a similar effect but only in aggregation culture. Surprisingly the addition of CHIR99021 had either no or only very minor effects on the total number of H+C+ cells produced. Conversely, Bmp4 increased the H+C+ percentage in monolayer culture during differentiation. The addition of Bmp4 and activin during the initial stage of differentiation gave the overall highest yield of H+C+ cells in both suspension and monolayer (Table 7).

While we were able to obtain H+C+ positive populations in adherent monolayer culture, it was still significantly less efficient than aggregation differentiation. Since FGF signalling was recently shown to be required for transitions between ES cells and early states of differentiation in multiple lineages (Kunath et al. 2007; Stavridis et al. 2007), we tested whether the addition of FGF4 would improve our monolayer differentiation protocol. Inclusion of FGF4 in our differentiation protocol doubled the H+C+ cell number in monolayer cultures (Table 8). The Hex$^{RS}$ expressing cells form colony-like growths as illustrated in FIG. 8. The ability to consistently obtain high levels of H+C+ cells in adherent monolayer cultures allows for the production of significant quantities of ADE from ES cells. This protocol was repeated on wild-type E14Tg2a ES cells and resulted in the same percentage of Cxcr4 single positive cells, indicating its potential for producing ADE from genetically unmodified ES cells (FIG. 8).

To obtain optimal levels of H+C+ induction, Fgf4 was required for the entire differentiation protocol (FIG. 8, Table 8). Interestingly, the number of CXCR4 expressing cells did not increase with the addition of Fgf4 indicating that the effect of Fgf4 appears to be specific to the induction of H+C+ double positive ADE, and not a general effect on mesendoderm induction (FIG. 8). We were initially surprised by this observation, as FGF signalling has been shown to mediate mesoderm, but not endoderm induction (reviewed in (Bottcher and Niehrs 2005)). To confirm a role for FGF signalling in H+C+ induction, we blocked FGF signalling using PD17304, a highly specific inhibitor of the FGF receptor (Mohammadi et al. 1998). PD17304 was added to cultures either from day 0-2, day 3-7 or for the entire differentiation protocol. The presence of PD17304 in our cultures appears to inhibit both C+ single positives and H+C+ double positives. When PD17304 was present for the first two days of differentiation, but then removed, we were able to generate a reduced number of both C+ and H+C+ cells (FIG. 8). However, when PD17304 was present for the entire protocol, we were unable to generate either population. Interestingly, when Fgf signalling is blocked for days 3-7, it resulted in a complete loss of both H+C+ and C+ populations and also dramatically compromised cell survival such that any cells that did survive were morphologically distinct from those obtained in the presence of activin and FGF4 (FIG. 8). Thus in the presence of FGF signalling, Activin and Bmp4, ES cells may progress towards mesendoderm, but when FGF signalling is blocked they shift towards a lineage that is unable to survive in these conditions.

Differentiation of Human ES Cells to Anterior Definitive Endoderm.

We have also differentiated Human ES cells using the adherant monolayer protocol described herein and compared these cells to Human ES cells differentiated as described in two different established protocols for endoderm differentiation in the human ES cell line SHEF4. Similar results have been obtained with a second human ES cell line, SHEF6 (not shown). Cells were grown on mtesr (Stem Cell Technologies) and passaged with EDTA at a split ratio of 1:3. Cells were plated in mtesr and allowed to adhere overnight onto Matrigel (BD) and in the morning, media was changed to N2B27 and cells were differentiated as we have described for mouse ES cells(Morrison et al., 2008). The only exception being that cells were initially plated on Matrigel instead of gelatin. Cells were fixed at day 0, 3, 5, 7 and 9 in 4% PFA. Results are shown in FIG. 14.

Interestingly, the activin buturate protocol (panel A) produces an abundance of Cxcr4 positive, mesendoderm (see discussion) and only isolated clumps of CER1 expressing ADE. The activin/Wnt3a protocol, while more efficient, was highly also highly heterogenous. Thus, while it has been proposed that CXCR could be used to enrich for endoderm in Human ES cell differentiation (D'Amour et al., 2005), it appears to mark a heterogenous population of cells that contains a small proportion of ADE. Based on this new human data and our previous work in the mouse, the marker Cxcr4 is an early primitive streak marker that is expressed by both mesoderm and endoderm precursors. Even in conjunction with c-kit (Gouon-Evans et al., 2006), Sox17 or Goosecoid (Yasunaga et al., 2005), these enrichments will at best produce the equivalent of anterior primitive streak mesendoderm, a population that has not yet fixed its positional identity and still contains mesodermal as well as endodermal progenitors, and array data contained herein indicates these markers will at best produce a mixed population of H−C+, and H+C+ cells).

Panel C shows data from the differentiation protocol described herein. In mouse the defined monolayer differentiation protocol lasted 7 days, as Human ES cells are thought to potentially be related to a different state of embryonic development, we have done a carefully time course and analyzed differentiation by immuno-histochemistry for CXCR4, FOXA2, CLIC6. Human ES cells are thought to be a more mature epiblast like cell (slightly later stage of development (Brons et al., 2007; Tesar et al., 2007)) and the first stage of our protocol includes two factors, BMP4 and activin/Nodal recently shown to be involved in epiblast development (see discussion). As a result we thought this phase might promote synchronous growth and differentiation in HES cultures. This appears to be the case, as we are able to initiate this protocol at a relatively low density (left hand panel in C) and by day 3, obtain a relatively homogenous population of CXCR4 expressing mesendoderm. Moreover, this population of cells appears to convert to a culture consisting predominantly of FoxA2, CER1 and CLIC6 positive cells. Taken together this data shows that our conditions, defined initially for mouse, are extremely effective at driving HES cells towards ADE. This represents the first demonstration of the generation of positionally defined endoderm from HES.

Further Characterisation of Novel Markers of ES Cell Derived ADE

RN wass prepared from Hex$^{RS}$ ES cells, E14Tg2a ES cells and the four H/C sorted populations of differentiated Hex$^{RS}$ ES cells from three independent experiments. 2 μg was used to prepare a probe for hybridsation to the illumina Mouse-6-v1 Beadchip. The data was filtered so that any probe with a detection score <0.95 across all samples was removed from the analysis prior to log transformation (base2) and quantile normalisation. Initial inspection of the data suggested the samples clustered loosely according to when they were processed, therefore a model based analysis was used. Differentially expressed probes were identified using LIMMA (Smyth, 2004) modeling the sample effect and the date when the samples were processed once grouped. Data was also analyzed in a pairwise fashion to determine significant differentials between each of the four populations. This was used to produce a molecular signature for the H+C+ double positive population. This list contained 54 genes. We then refined this analysis by setting a fold filter on the list of H+C+ specific genes of 1.4 fold compared to H−C+ and 2.0 fold compared to H−C−. These filters were selected based on the behavior of the known ADE markers, Cer1 HHex and Foxa1, 2 and 3. When we include this analysis, the list of A specific probe sets now numbers, 73. Primers were designed to the genes represented by these 73 probes and RT-PCR used to validate their expression in both the A population, and through out differentiation in response to activin. Based on this analysis, we were able to reduce this gene list to 47 genes that behave in a similar manner to either Hex or Cer1 during in vitro differentiation. A number of genes are already known based on their appearance in the literature or their well defined roles in endoderm differentiation (e.g. HHex, Foxa3, Cer1). Our resulting markers contains the following markers which includes those already implicated as being involved in endoderm differentiation, but which may now used to identify and/or generate ADE: Sst, Pyy, Ghrl, Slc38a5, Chga, Exph5, Tmprss2, Clic6, 1110003E01Rik, Sstr2, 4732456N10Rik, Rab15, Rnase4, Slc6a4, Fxyd3, Slc12a2, 1700027A23Rik, Tm4sf2, 0610040B21Rik (aka txndc12), Apoa1, 2410021P16Rik (aka acad10), 4832420M10, Fzd5,Gckr, Enpp5, Syt5, Cklfsf8 (aka Cmtm8), Robo1, Ctsh, Rarres1, Sec1412, Ripk4, Slc7a8, Ng23, Krt2-7, Sfrp5, Pga5, foxa1, foxa2, foxa3, Cer1, Hhex, Otx2, Gatn3. From this list, the following are cell surface markers, which may be particularly useful in identifying and/or generating ADE cells. We have gone on to analyze these markers and two commercially available antibodies of these markers (Clic6 and Frzd5) when used to shown their applicability as specific markers of ADE cells (see FIG. 15).

Experimental Procedures

Gene Targeting and Production of the Hex$^{RS}$ Mouse Line

The 5' and 3' targeting arms used for homologous recombination were described by Martinez Barbera et al., (2000) with an Asc1 and Pac1 site engineered downstream of the Hex ATG (a gift from Shankar Shrinivas). The RedStar gene was linked via an internal ribosome entry site (IRES) to the gene encoding blasticidin resistance (BSD) followed by a cytomegalovirus promoter-driven hygromycinR-thymidine kinase dual selection cassette flanked by loxP sites. This cassette was fused in frame with the ATG of Hex. Following electroporation into E14Tg2a ES cells correctly targeted clones were expanded and characterized by Southern Blot. The selection cassette was excised from three clones and two of them, Hex$^{RS}$1-2, were selected for further analysis. The ES cell line Hex$^{RS}$1 was injected into blastocysts to generate the Hex$^{RS}$ mouse line. Mice were maintained on a mixed 129O1a x C57B1/6 background.

Culture and Differentiation of ES Cells

Mouse ES cells were cultured according to Li et al., (1995). ADE was induced under serum-containing conditions using a 2-step protocol. ES cells were seeded onto non-coated 10 cm petri dishes (Sterilin) at a density of 5×10³ cells/ml in GMEM supplemented as described in Li et al., (1995) except in the absence of LIF. EBs were harvested after two days by centrifugation and replated in N2B27 medium (StemCellSciences) supplemented with 20 ng/ml activin A (R&D) and 20 ng/ml EGF (R&D). This media was replaced again two days later. 10 ng/ml BMP4, 20 ng/ml activin A (R&D) and 1×10⁻⁵M all-trans retinoic acid (Sigma) were added where indicated.

For ADE induction under serum-free conditions in suspension culture, ES cells were seeded as above in N2B27 medium supplemented with 10 ng/ml BMP4 and 20 ng/ml activin A. Following 2 days of culture, EBs were harvested and cultured as above in SF03 medium (Iwai Chemicals Company) supplemented with 0.1 mM 2-mercaptoethanol (2ME), 0.1%BSA (Invitrogen), 20 ng/ml activin A and 20 ng/ml EGF. 10 ng/ml FGF4 (R&D), 10 ng/ml Bmp4, 20 ng/ml activin A, 10 μM all-trans retinoic acid were added as indicated. For ADE induction in adherent monolayer culture, ES cells were seeded onto gelatin coated 6 well dishes (Iwaki) at a density of 1×10⁴ cells/ml in N2B27 medium (StemCellSciences) supplemented with 10 ng/ml Bmp4, 20 ng/ml activin A and, where indicated, 10 ng/ml FGF4. Following 2 days of culture the media was replaced with SF03 medium supplemented with 0.1 mM 2-mercaptoethanol (2ME), 0.1%BSA (Invitrogen), 20 ng/ml activin A, 10 ng/ml FGF4 and 20 ng/ml EGF. The media was replaced every 2 days for the duration of the experiment. 100 ng/ml PD173074 (Sigma) or 25 μM SU5402 (Calbiochem) were added to the culture as indicated. FGF2, 5, 8b and 10 (R&D) were used at 10 ng/ml. For the induction of pancreatic progenitor cells, sorted cell fractions were seeded onto gelatin coated 3 cm 6 well dishes (Iwaki) at 2.5×10⁵ cells/ml in N2B27 media supplemented with 10 ng/ml FGF4, 2 μM all trans retinoic acid and 0.25 μM KAAD-cyclopamine (Toronto Research Chemicals). Hepatocyte differentiation was as described in Gouon-Evans et al., (2006) except N2B27 was used as the base media at all stages and activin was not included, while BMP4, FGF2 and VEGF were. Induction of haematopoietic precursors was described by Kennedy and Keller, (2003).

For expansion of sorted cell fractions, day 7 purified fractions were plated on gelatin in 24 well plates (Iwaki) in N2B27 medium supplemented with 0.5 mM ascorbic acid, 450 μM monothioglycerol (MTG), 50 ng/ml BMP4, 10 ng/ml FGF2 (R&D) and 10 ng/ml VEGF. 2.5×10⁵ cells were plated into each well of which 10% appeared to be viable and adherent after 24 hours. These cultures were expanded until confluence (approximately 14 days) and all subsequent passaging was done approximately every 7 days using Trypsin-EDTA (Sigma), splitting either 1:2 or 1:3. RedStar fluorescence was observed daily by microscopy. Quantitation of Hex$^{RS}$ expressing and antibody positive cells was done using fluorescent, phase and in the case of antibodies, DAPI overlays using Velocity 4.32 software (Improvision). Quantitation of the fold expansion was based on a 10-fold increase in cell number during the first passage multiplied by the split achieved at each passage to P7, a total of 216-fold. Cells were further differentiated as described above, except they were pre-treated for 24 hours in the above media supplemented with 20 ng/ml activin A.

Flow Cytometry and Cell Sorting

FITC-conjugated rat anti-CD184 (Cxcr4), FITC-conjugated rat anti-CD31 and FITC conjugated rat anti-CD45 were purchased from BD Pharmingen. Cells were stained with Topro3-iodide (Invitrogen) to exclude dead cells from the analysis. Cells were analysed using a FACS Calibur (BD Biosciences) or sorted using a MoFlo MLS flow cytometer (DakoCytomation).

Gene Expression Analysis

Total RNA was prepared from a minimum of $1 \times 10^4$ cells using Trizol reagent (Invitrogen). 1 µg of RNA was used as a template for cDNA synthesis using Superscript III (Invitrogen). Real-time RT-PCR was performed using a LightCycler 480 (Roche) and LightCycler 480 SYBR Green 1 Master (Roche). Primers and PCR conditions are listed in supplementary table 7.

Immunostaining

Sorted cells were seeded onto gelatin coated 24 well dishes (Iwaki). Adherence of cells was enhanced by centrifugation at 1200 rpm for 3 min. Sorted cells, monolayer differentiated cells and ES cells were washed in PBS, fixed in 4% paraformaldehyde for 10 min and permeabilised by washing in PBS supplemented with 0.1% Triton X (PBST). The following primary antibodies were used, all are anti-mouse: anti-Oct3/4, anti-Foxa2, anti-HNF-4α (Santa Cruz), anti-Cer1 (R&D), anti-Gsc (Santa Cruz), anti Sox17 (Santa Cruz), anti-E-cadherin (Takara Bio Inc) anti-alpha fetoprotein (NeoMarkers), anti-Albumin (Bethyl laboratories inc), anti-Nkx 2.2 (Santa Cruz). Anti-Pdx 1 was a gift from P. Serup or purchased from Santa Cruz. Alexa 488 and 568 (Molecular Probes) secondary antibodies were used.

Kidney Capsule Transplantations

Cells were sorted at day 7 and approximately $5\text{-}10 \times 10^4$ cells of each population were transplanted under the kidney capsule of adult 129 mice. Four to eight weeks after transplantation surviving mice were sacrificed and the kidneys removed and fixed in 4% paraformaldehyde (PFA). Following fixation the kidneys were embedded in paraffin wax, sectioned and stained with hematoxylin and eosin and PAS reagent (Sigma).

DNA Microarray Analysis

RNA was prepared from three independent experiments. 2 µg was used to prepare a probe for hybridsation to the Illumina Mouse-6-v1 Beadchip and the data deposited at Array Express (accession number E-TABM-515). The data was filtered so that any probe with a detection score <0.95 across all samples was removed from the analysis prior to log transformation (base2) and quantile normalisation. Initial inspection of the data suggested the samples clustered loosely according to when they were processed, therefore a model based analysis was used. Differentially expressed probes were identified using LIMMA (Smyth, 2004) modeling the sample effect and the date when the samples were processed once grouped. Data was also analyzed in a pairwise fashion to determine significant differentials between each of the four populations. This was used to produce a molecular signature for the H+C+ double positive population.

Results

Generation of Hex Reporter ES Cells

We created ES cell lines containing the marker gene, Red-Star (RS) (Knop et al., 2002) under the control of the Hex locus (FIG. 16A, B). These cells allowed us to monitor the emergence of newly formed ADE cells during in vitro differentiation. Two independent clones with normal karotype, HexRedStar (Hex$^{RS}$) 1 and 2, were selected for further analysis.

To confirm that expression of RS protein accurately reflects endogenous Hex expression, Hex$^{RS}$ 1 ES cells were used to generate a Hex$^{RS}$ mouse line. Embryos from Hex$^{RS}$/+ intercrosses are shown in FIG. 1C. Red fluorescence was detected in the anterior definitive endoderm, foregut as well as the liver and thyroid primordia, reflecting the expression of endogenous Hex protein as reported by Thomas et al., (1998). Weak expression was also observed in the inter-somitic vessels, endocardium of the heart and aspects of the dorsal aorta reflecting endogenous Hex expression in haematopoietic/endothelial precursors. Consistent with the previously described phenotype (Martinez Barbera et al., 2000) no live Hex$^{RS}$/Hex$^{RS}$ mice were born (table 1) and Hex$^{RS}$/Hex$^{RS}$ embryos appear to recapitulate the Hex null phenotype (FIG. 16C). Importantly, no phenotype was detected in Hex$^{RS/+}$ embryos or mice (FIG. 16C, table 1), indicating that any reduced Hex dosage in heterozygous cells will not impact on the ability of the cells to form ADE cells in vitro.

Expression of the HexRedStar Reporter During ES Cell Differentiation.

The secreted TGFβ ligand activin, has previously been shown to induce mesendoderm in Xenopus animal cap assays (reviewed in Okabayashi and Asashima, (2003)) and ES cells in culture (Kubo et al., 2004; Tada et al., 2005). To test the ability of activin to induce Hex$^{RS}$ expression, ES cells were differentiated in a two-step aggregation culture system in serum containing media for 48 hr followed by serum-free media supplemented with activin for 5 days. Under these conditions, 6.8-8.6% of cells were RS positive (RS+) at day 7 (FIG. 17A). RT-PCR analysis on purified RS+ cell populations revealed they expressed Sox17, Cer1, E-cadherin and Gata4, indicating these cells have an endoderm identity (FIG. 17B).

Hex is also expressed in mesodermal cell populations during early development including haemangioblast, angioblastic and endothelial precursor populations (Kubo et al., 2005; Rodriguez et al., 2001; Thomas et al., 1998). Flow cytometry analysis for the haematopoietic marker CD45 and endothelial marker CD31 showed that our activin treated cultures do not contain significant numbers of these cells (FIG. 23A), although the HRS cells can support haematopoetic differentiation (FIG. 17C). Using a Sox-1 GFP reporter ES cell line we also confirmed that our cultures do not contain neuroectodermal cells (FIG. 23B).

Isolation of Putative ADE Cells from Differentiating ES Cells

In addition to marking early ADE specification, Hex is also expressed in the AVE. To distinguish ADE from AVE we used the chemokine receptor Cxcr4 that is expressed in definitive mesoderm and endoderm populations, but excluded from all yolk sac visceral endoderm (McGrath et al., 1999; Yasunaga et al., 2005). Optimisation of media, additives and cell density (summarised in table 2 and table 3) identified a regimen in which ES cells cultured in suspension for two days and then five days serum-free in the presence of activin and EGF yielded significant numbers of RS/Cxcr4 double positive (H+C+) cells as assessed by flow cytometry (FIG. 17D). As might be expected, antagonists of ADE specification in vivo, Bmp4 and retinoic acid, blocked the induction of the RS positive population (table 2), without effecting Cxcr4 induction (data not shown).

Differentiating ES Cell Cultures have a Gene Expression Profile Similar to ADE.

To assess whether our differentiating ES cell cultures display a gene expression pattern similar to that observed during ADE induction we examined a range of markers during a timecourse (FIG. 3A). Epiblast markers, Oct4 (Pou5f1), Nodal and E-cadherin were expressed during the early phase of in vitro differentiation and then down-regulated concurrent with the expression of the early primitive streak markers Wnt3 and Brachyury (Tbra). Mixer-like 1 (Mixl1), Goosecoid (Gsc) and Foxa2, which define the streak region and prospective axial mesendoderm (notochord, prechordal plate and ADE), began to be expressed at day 3, and peaked at day 5-6. Importantly, genes expressed in the ADE, Cerberus 1 homologue (Cer1), Hex and Sox17, appeared between days 5-7 in our cultures. Although Mixl1 and Wnts have been implicated in endoderm induction (Hart et al., 2002) (Lickert et al., 2002), they are not expressed in definitive endoderm. In our culture conditions these markers are significantly expressed from day 3-5 and are then down regulated concordant with the emergence of markers of ADE. Thus, the dynamic pattern of expression evident in our differentiating ES cell cultures is similar to that during ADE specification in vivo. Furthermore, Cxcr4 and Hex protein is present from day 4 and 5 respectively (FIG. 18A, B), consistent with the expression of these markers in vivo (McGrath et al., 1999; Yasunaga et al., 2005; Yusuf et al., 2005). This suggests that the Cxcr4 single positive population may represent non-committed mesendoderm or a mixture of mesoderm and endoderm precursors, whereas the H+C+ population is committed ADE. The sequential expression of a number of markers observed in FIG. 18A is also consistent with differentiation towards anterior definitive endoderm rather than anterior visceral endoderm.

Isolation and Analysis of Hex+Cxcr4+ Cells Confirm their Similarity to ADE

Differentiating cultures were sorted into four populations based on RS (H) and Cxcr4 (C) protein levels and profiled by quantitative RT-PCR, microarrays and immunomarkers.

Levels of both Hex and Cxcr4 mRNA were highest in the H+C+ cell fraction confirming the success of cell sorting. Surprisingly, we found that the transcript level of Hex in the H+C− and H−C+ populations were very similar and significantly less than the H+C+ population (FIG. 19A). This may reflect the time lag between the production of Hex transcript and the presence of RS protein.

The H+C+ cell population expressed the highest levels of E-cadherin, Cxcr4, Cer1 and Hex transcript (FIG. 19A), all of which are expressed in the ADE. Importantly, the expression of markers Tbra, Wnt3 and Mixl1 that are associated with the early primitive streak but not the ADE, were low in the H+C+ population. Markers of posterior endoderm (Cdx2), paraxial mesoderm (Meox1) and parietal endoderm (Sox7) were only detected at very low levels during differentiation and barely detectable in the H+C+ cell population (FIG. 19A). In accordance with the PCR data, immunostaining showed almost all of the H+C+ cells to express the ADE marker Cer1, and the definitive endoderm markers Foxa2 and E-cadherin, but not the ES cell marker Oct4 (FIG. 19B).

Microarray analysis of the four Hex/Cxcr4 cell fractions sorted from day 7 differentiated cultures showed that these fractions cluster close to each other and not to the samples derived from undifferentiated ES cell cultures (FIG. 19C). The close clustering of the two ES cell lines to each other indicates there is little difference in gene expression in Hex$^{RS}$ heterozygote and wild-type ES cells. Of the differentiated populations, the H+C+ population is most closely related to the H−C+ population, consistent with the view that the H+C+ ADE cells arises from the H−C+ mesendodermal cell population. Hierarchical clustering of the differentially expressed genes identified in a pairwise analysis of all four populations is shown in FIG. 4D. This analysis supports the expression analysis in FIG. 4A and gives a clear indication of the unique signature of the H+C+ fraction, which expresses a significant number of ADE markers such as Cer1, Frizzled 5, Lhx1 (Lim1), Otx2 and a number of novel gene products. Quantitative RT-PCR validation supports the identity of this expression cluster as unique to the H+C+ fraction (FIG. 19E). We conclude from this data that the H+C+ population is enriched for the expression of anterior markers, normally expressed in the ADE.

Differentiation Potential of ES Cell Derived ADE.

Since both pancreas and liver arise from ADE, we tested the hepatic potential of the H+C+ population using a method adapted from Gouon-Evans et al., (2006), which involves up to 13 additional days of hepatocyte differentiation (total culture period 20 days). By day 12, AFP positive hepatoblasts were apparent in the H+C+ cell fraction and while some AFP expression was observed in all four fractions, it was significantly higher in the double positive fraction (FIG. 20C). No AFP positive cells were formed from non-induced ES cells cultured in the same conditions (data not shown). This trend was already apparent at the RNA level from day 9, where the H+C+ fraction expressed at least 3-4 fold higher levels of Krt19, Albumin, AFP, Hnf6 and Foxa2 transcript than any of the other fractions (FIG. 20B). The pattern of Hex expression during the differentiation period is also consistent with its later expression in the liver primordia (Thomas et al., (1998) and FIG. 16C) with RS protein detected at day 9 in forming hepatocytes but only in the H+C+ and weakly in H+C− sorted cells (FIG. 20A). Flow cytometry at this stage of differentiation also supports the quantitative capacity of the H+C+ fraction to differentiate towards liver, as 62% of the early hepatocyte cultures resulting from H+C+ sorted cells were Hex positive, whereas only 11% of the H−C+ population were weakly fluorescent (FIG. 20A). By day 20, AFP expression was reduced and the number of Albumin positive cells had increased significantly in the H+C+ population reflecting the maturation of hepatoblasts to hepatocytes (FIG. 20D). At this stage, Albumin expression was not detected in the other fractions (data not shown). On the contrary, under these conditions large numbers of cardiomyocytes were observed in H−C+ and double negative fractions (FIG. 20E). Taken together these results suggest H+C+ fraction contains lineage restricted endodermal progenitors.

To examine the pancreatic potential of the sorted cell populations we cultured them with cytokines implicated in pancreatic specification (Hebrok et al., 1998; Kumar et al., 2003); retinoic acid, FGF4 and the sonic hedgehog inhibitor cyclopamine. H+C+ sorted cells generated clusters expressing markers of the emerging pancreatic buds, Pdx1 and Hnf4α with the highest efficiency, indicating their pancreatic differentiation potential in vitro (FIG. 20F). In contrast H+C− fractions did not give rise to co-expressing clusters. Limited potential was detected from the H−C+ and H−C− fractions with 2 and 9-fold reduced cluster number respectively and reduced Pdx1 and Hnf4α immunostaining intensity for both (FIG. 20F, H−C− data not shown), presumable reflecting some ability of non-committed cells to generate ADE upon further culture. Using undifferentiated ES cells as a starting population for this 5-day protocol did not generate any Pdx1 or Hnf4α positive cells (data not shown). When this protocol was repeated substituting FGF10 for FGF4 based on a human ES cell differentiation protocol described by D'Amour et al., (2006), a similar (3-fold) quantitative enhancement in cluster formation in the H+C+ fraction was obtained (data not shown).

To evaluate the in vivo potency exhibited by cells in each H/C fraction they were sorted at day 7 of differentiation and immediately transplanted under the kidney capsule of adult mice. Nine transplants were performed for each sorted fraction. The H−C− transplants gave rise to large teratomas (5 out of 9) indicating these fractions still contained some ES cells. In contrast, no teratomas were generated from the H+C+ transplants. The H+C+ cells in one animal (1 out of 9) gave rise to a small growth that contained endodermal derivatives indicated by the presence of ductal epithelial structures containing PAS positive secretory granules (FIG. 20G). Similar epithelial structures were observed in the growths from the H−C+ grafts (4 out of 9) and H+C− grafts (3 out of 9). The H−C+ transplants were the only ones (excluding the H−C− teratomas) that contained cartilage (FIG. 5G), consistent with the notion that this fraction still contains cells competent to generate both mesoderm and endoderm.

Expansion Potential of ES Cell Derived ADE.

During the early phase of further ADE differentiation we noticed that purified H+C+ ADE proliferated in the presence of FGF2, BMP4 and VEGF. To test whether these conditions could be used to expand H+C+ ADE progenitors the four H/C FACS purified fractions were plated in defined media incorporating these cytokines. All four populations were seeded at approximately 10% confluence and the growth of the red population observed over time. Initially all four population were able to grow, but only the H+C+ fraction contained significant numbers of Hex positive cells (FIG. 21A). While these cultures were not homogeneous, the H+C+ fractions were able to give rise to Hex positive colonies upon repeated passaging (FIG. 21B) and the percentage of Hex positive cells in these cultures expanded over time, reaching as high as 96% (FIG. 24). Cultures were routinely split 1:2 or 1:3 (see methods) for 8 passages to generate cultures that were a minimum of 90% Hex positive by passage 7. Based on these figures, this constituted a 1944-fold expansion of putative ADE. In contrast, cells from the other three fractions (H+C−, H−C+ and H−C−) were unable to survive multiple passages. To confirm the identity of cultured H+C+ cells, we examined the expression of the endoderm markers Foxa2 and E-cadherin, the ADE marker Cer1 and ES cell marker Oct4 at passage 5. The majority of cells within these cultures expressed Cer1, Foxa2 and E-cadherin, but not Oct4 (FIG. 21C), indicating these cells represent a form of ADE progenitor. To confirm that these cultures were predominantly ADE we quantitated the percentage of cells expressing these markers and found that 79% (+/−1.4) expressed Cer1, 71% (+/−14) expressed Hex and 54% (+/−2.8%) expressed E-cadherin. Moreover, quantitation of the DAPI staining shown in FIG. 6 and similar images indicated that the E-cadherin expressing fraction contained greater than 3-fold more mitotic nuclei than E-cadherin negative fraction, supporting the notion that the endodermal progenitors in these cultures are the major proliferating cell type.

The ability of these cultures at passage 7 to further differentiate towards hepatic and pancreatic cell types was tested as described above. Pancreatic differentiation produced clusters of Nkx2.2 and Pdx1 expressing cells (FIG. 21D), whereas hepatic differentiation resulted in fields of cells with the morphology of immature hepatocytes expressing both AFP and Albumin (FIG. 21D).

Taken together these results indicate that while the overall differentiation efficiency of ES cells to ADE using our strategy may not exceed the 20% of the total culture, the ability to sort these ADE cells, expand and maintain them as progenitors, greatly enhances the utility of our approach.

Defined Conditions for ADE Induction in Adherent Monolayer Suggest Novel Roles for FGF Signalling.

Mechanistic studies on lineage specification in the mesendoderm require defined serum-free conditions and would benefit from an adherent monolayer culture system. As ADE specification in vivo occurs during a series of complex morphogenetic movements, it is possible that differentiation cannot be uncoupled from the multi-cellular interactions present within an embryoid body. Mesendoderm induction in the absence of positional specification has been reported using the serum-free media SF03 in an adherent monolayer culture system (Tada et al., 2005). Initial attempts to culture $Hex^{RS}$ cells in SF03 and activin, both as aggregates and in monolayer, did not yield sufficient number of viable cells for in vitro culture of ADE (table 5).

Given our results with N2B27 media (FIG. 2A and D) we tried various permutations of N2B27, SF03 and growth factors (table 5). Following extensive optimisation, we found that a significant H+C+ cell population could be induced in both suspension culture and monolayer following a two-step serum-free differentiation protocol. Cells cultured in N2B27 with activin and Bmp4 for 2 days and then switched to SF03 with activin and EGF for 5 days gave the overall highest yield of H+C+ cells in both suspension and monolayer (table 5, 10).

As we were able to obtain H+C+ positive populations in adherent monolayer culture under defined conditions, albeit at lower efficiency than aggregation differentiation (6% versus 13%), this afforded the possibility of identifying additional determinants. A requirement for FGF signalling for transitions between ES cells and early states of differentiation in multiple lineages has recently been shown (Kunath et al., 2007; Stavridis et al., 2007). We tested whether the addition of FGF4 would improve our monolayer differentiation protocol. Inclusion of FGF4 doubled the H+C+ cell number in monolayer cultures (FIG. 22A and table 11). The $Hex^{RS}$ expressing cells appeared to cluster, forming colony-like growths as shown in FIG. 22B. This protocol was repeated on wild-type E14Tg2a ES cells and resulted in colonies with similar morphology that contained the same percentages of Cxcr4 single positive cells, indicating its potential for producing ADE from genetically unmodified ES cells (FIG. 22A).

A requirement for FGF signalling during ADE specification was surprising, as FGF signalling has been shown to mediate mesoderm, but not endoderm induction (reviewed in Bottcher and Niehrs, (2005)). To determine whether signalling downstream of FGF was required for the differentiation of ES cells to ADE, we used a selective inhibitor of the FGF receptor, PD173074 (Mohammadi et al., 1998). When PD173074 was present for the first two days of differentiation, but then removed, we observed a reduced number of both C+ and H+C+ cells (FIG. 22A and table 11). However, when PD173074 was present for the entire protocol, we were unable to generate either population. Interestingly, when FGF signalling is blocked for days 3-7, it resulted in a complete loss of both H+C+ and C+ populations, altered morphologies and also dramatically compromised cell viability (FIG. 7B). Similar results were obtained with a second FGF inhibitor, SU5402 (Mohammadi et al., 1997) (FIG. 25).

Despite an overall requirement for FGF signalling in differentiation towards mesoderm and endoderm, the addition of FGF4 appeared to promote specifically H+C+ double positive ADE (FIG. 22A). Thus, rather than promoting overall levels of differentiation towards both mesoderm and endoderm lineages, the addition of exogenous FGF4 to these cultures led to the induction of anterior markers Cer1 and Gsc and increased the expression of Foxa2 and Sox17 (FIG. 22C, D), while suppressing levels of both mesodermal and primitive streak gene expression (FIG. 22D).

The action of FGF on the initial formation of ES cell derived ADE is also reflected in the optimal timing of FGF addition. FIG. 22E shows that when FGF4 is added solely during the second phase of differentiation we obtain up to 20% H+C+ ADE. Interestingly, when exogenous FGF4 was added only between days 3-4, the time window in which these cultures have neither mesodermal or endodermal identity, there was a significant effect on the production of ADE (FIG. 22E, F). We also tested FGF2, 5, 8b, and 10 for activity in this protocol and found that only FGF2 had a similar ability to promote H+C+ ADE (FIG. 25).

Discussion

We have described the production of a defined population of ADE cells from embryonic stem cells. This represents the first derivation and purification of endoderm with specific anterior-posterior (A-P) properties in vitro. We have demonstrated increased potency of these cells to differentiate towards liver and pancreas and identified a condition in which Hex expressing ADE-like progenitors can be propagated in culture. Through our efforts to establish defined conditions for ADE specification we have uncovered a novel role for FGF signalling in endoderm differentiation.

Previously reported mesendoderm induction protocols employed markers normally expressed in either the node (Gsc) or primitive streak (Tbra). Refinements to these approaches have involved a second marker believed to represent a more defined lineage such as Foxa2, a pan axial mesendoderm marker or Sox17, a transient marker of all endoderm (Kanai-Azuma et al., 2002). Despite these refinements, the resulting population still lack any A-P identity. By using the Hex$^{RS}$ reporter cell line in conjunction with Cxcr4 we have been able to purify an in vitro equivalent to ADE. This cell fraction appears to be ADE as judged by the following criteria: First, the sequence of gene expression in our ES cell cultures mirrors that which occurs during definitive endoderm differentiation in vivo. Second, the H+C+ cells express high levels of ADE markers and very low levels of markers of the primitive streak, mesoderm and ES cells and third these cells have the greatest capacity to differentiate further towards derivatives of the ADE, liver and pancreas. Thus, the ability to identify and purify ES cell derived ADE is an important platform for accurate recapitulation of in vivo differentiation.

We have also managed to couple the ability to generate ES cell derived ADE with the capacity to expand this population in vitro. While this population is not entirely homogeneous it appears to contain very high levels of anterior endoderm in the form of Hex and Cer1 expressing populations (between 70-90%) indicating the exciting possibility that our culture system may ultimately afford the generation of self-renewing lineage restricted anterior endoderm progenitor cell lines. Nonetheless the ability to grow and expand sorted ADE cells as an endodermal progenitor population greatly enhances the utility of ES derived ADE as a platform for further differentiation.

During the development of monolayer differentiation towards ADE we observed an interesting dependence on BMP4 and activin for cell survival and/or proliferation in the serum-free differentiating cultures (Supplementary Table 5). As this particular requirement appears limited to the early phase of differentiation, we believe this activity to be related to the requirement for these pathways in epiblast growth. Both Nodal (Camus et al., 2006; Mesnard et al., 2006) and BMP (DiGregorio et al., 2007) signalling have recently been shown to be required for the development and growth of the primitive ectoderm.

We were initially surprised to discover that FGF signalling promoted ADE production from ES cells since FGF signalling is typically associated with mesoderm induction and cell migration during gastrulation (Casey et al., 1998; Ciruna and Rossant, 2001; Mizoguchi et al., 2006; Poulain et al., 2006; Rodaway et al., 1999). In lower vertebrates FGF signalling has also been shown to enhance mesoderm differentiation while suppressing endoderm and this view has also been supported by analysis of the FGFR1 mutant mouse embryos (Deng et al., 1994; Yamaguchi et al., 1994). However, there is also evidence to support a role for FGF signalling in the specification of anterior mesendoderm, as FGFR1(−/−) ES cells are unable to contribute to the endoderm (Ciruna et al., 1997). Previously this defect had been attributed to an inability of the FGFR1(−/−) ES cells to traverse the primitive streak and participate in gastrulation movements. However, our demonstration that FGF signalling can potentiate anterior endoderm differentiation in defined monolayer culture suggest these observations reflect a more fundamental requirement for FGF signalling in the specification of the anterior most gastrulating tissue in embryogenesis. This role might be mediated through direct induction of ADE target genes or alternatively through selective cell survival and/or proliferation.

Our ability to produce ADE cells in a chemically-defined, monolayer culture system represents a significant step towards the uncoupling of lineage specification from the complex morphogenetic movements and context dependent positional cues that occur in vivo during gastrulation. It also represents an important intermediate step in the in vitro generation of mature cell lineages from foregut endoderm.

REFERENCES

Angerer L M, Angerer R C (2000) Animal-vegetal axis patterning mechanisms in the early sea urchin embryo. Dev Biol 218(1): 1-12.

Bagutti C, Wobus A M, Fassler R, Watt F M (1996) Differentiation of embryonal stem cells into keratinocytes: comparison of wild-type and beta 1 integrin-deficient cells. Dev Biol 179(1): 184-196.

Beck F, Erler T, Russell A, James R (1995) Expression of Cdx-2 in the mouse embryo and placenta: possible role in patterning of the extra-embryonic membranes. Dev Dyn 204(3): 219-227.

Beddington R S P, Robertson E J (1998) Anterior patterning in mouse. Trends Genet 14(7): 277-284.

Beddington R S P, Robertson E J (1999) Axis development and early asymmetry in mammals. Cell 96(2): 195-209.

Bennett C N, Ross S E, Longo K A, Bajnok L, Hemati N et al. (2002) Regulation of Wnt signaling during adipogenesis. J Biol Chem 277(34): 30998-31004.

Bottcher R T, Niehrs C (2005) Fibroblast growth factor signaling during early vertebrate development. Endocr Rev 26(1): 63-77.

Brickman J M, Jones C M, Clements M, Smith J C, Beddington R S P (2000) Hex is a transcriptional repressor that contributes to anterior identity and suppresses Spemann organiser function. Development 127(11): 2303-2315.

Brons, I. G., Smithers, L. E., Trotter, M. W., Rugg-Gunn, P., Sun, B., Chuva de Sousa Lopes, S., Howlett, S. K., Clarkson, A., Ahrlund-Richter, L., Pedersen, E. A., et al. (2007). Derivation of pluripotent epiblast stem cells from mammalian embryos. Nature.

Camus A, Perea-Gomez A, Moreau A, Collignon J (2006) Absence of Nodal signaling promotes precocious neural differentiation in the mouse embryo. Dev Biol 295(2): 743-755.

Casey E S, O'Reilly M A, Conlon F L, Smith J C (1998) The T-box transcription factor Brachyury regulates expression of eFGF through binding to a non-palindromic response element. Development 125(19): 3887-3894.

Chen Y, Schier A F (2001) The zebrafish Nodal signal Squint functions as a morphogen. Nature 411(6837): 607-610.

Ciruna B, Rossant J (2001) FGF signaling regulates mesoderm cell fate specification and morphogenetic movement at the primitive streak. Dev Cell 1(1): 37-49.

Ciruna B G, Schwartz L, Harpal K, Yamaguchi T P, Rossant J (1997) Chimeric analysis of fibroblast growth factor receptor-1 (Fgfr1) function: a role for FGFR1 in morphogenetic movement through the primitive streak. Development 124 (14): 2829-2841.

Conti L, Pollard S M, Gorba T, Reitano E, Toselli M et al. (2005) Niche-independent symmetrical self-renewal of a mammalian tissue stem cell. PLoS Biol 3(9): e283.

Cornell R A, Musci T J, Kimelman D (1995) FGF is a prospective competence factor for early activin-type signals in Xenopus mesoderm induction. Development 121(8): 2429-2437.

D'Amour K A, Bang A G, Eliazer S, Kelly O G, Agulnick A D et al. (2006) Production of pancreatic hormone-expressing endocrine cells from human embryonic stem cells. Nat Biotechnol 24(11): 1392-1401.

D'Amour, K. A., Agulnick, A. D., Eliazer, S., Kelly, O. G., Kroon, E., and Baetge, E. E. (2005). Efficient differentiation of human embryonic stem cells to definitive endoderm. Nat Biotechnol 23, 1534-1541.

Davidson E H, Rast J P, Oliveri P, Ransick A, Calestani C et al. (2002) A genomic regulatory network for development. Science 295(5560): 1669-1678.

Deng C X, Wynshaw-Boris A, Shen M M, Daugherty C, Ornitz D M et al. (1994) Murine FGFR-1 is required for early postimplantation growth and axial organization. Genes Dev 8(24): 3045-3057.

Deutsch G, Jung J, Zheng M, Lora J, Zaret K S (2001) A bipotential precursor population for pancreas and liver within the embryonic endoderm. Development 128(6): 871-881.

Dyson S, Gurdon J B (1998) The interpretation of position in a morphogen gradient as revealed by occupancy of activin receptors. Cell 93(4): 557-568.

Finley K R, Tennessen J, Shawlot W (2003) The mouse secreted frizzled-related protein 5 gene is expressed in the anterior visceral endoderm and foregut endoderm during early post-implantation development. Gene Expr Patterns 3(5): 681-684.

Friedman J R, Kaestner K H (2006) The Foxa family of transcription factors in development and metabolism. Cell Mol Life Sci 63(19-20): 2317-2328.

Gadue P, Huber T L, Paddison P J, Keller G M (2006) Wnt and TGF-beta signaling are required for the induction of an in vitro model of primitive streak formation using embryonic stem cells. Proc Natl Acad Sci USA 103(45): 16806-16811.

Gouon-Evans V, Boussemart L, Gadue P, Nierhoff D, Koehler C I et al. (2006) BMP-4 is required for hepatic specification of mouse embryonic stem cell-derived definitive endoderm. Nat Biotechnol 24(11): 1402-1411.

Green J B, Smith J C (1990) Graded changes in dose of a Xenopus activin A homologue elicit stepwise transitions in embryonic cell fate. Nature 347(6291): 391-394.

Hart A H, Hartley L, Sourris K, Stadler E S, Li R et al. (2002) Mixl1 is required for axial mesendoderm morphogenesis and patterning in the murine embryo. Development 129 (15): 3597-3608.

Hay, D. C., Fletcher, J., Payne, C., Terrace, J. D., Gallagher, R. C. J., Snoeys, J., Black, J. R., Wojtacha, D., Samuel, K., Hannoun, Z., et al. (2008a). Highly efficient differentiation of hESCs to functional hepatic endoderm requires ActivinA and Wnt3a signaling. Proc Natl Acad Sci USA 105, doi10.1073pnas.0806522105.

Hay, D. C., Zhao, D., Fletcher, J., Hewitt, Z. A., McLean, D., Urruticoechea-Uriguen, A., Black, J. R., Elcombe, C., Ross, J. A., Wolf, R., et al. (2008b). Efficient differentiation of hepatocytes from human embryonic stem cells exhibiting markers recapitulating liver development in vivo. Stem cells 26, 894-902.

Hebrok M, Kim S K, Melton D A (1998) Notochord repression of endodermal Sonic hedgehog permits pancreas development. Genes Dev 12(11): 1705-1713.

Huber O, Bierkamp C, Kemler R (1996) Cadherins and catenins in development. Curr Opin Cell Biol 8(5): 685-691.

Kanai-Azuma M, Kanai Y, Gad J M, Tajima Y, Taya C et al. (2002) Depletion of definitive gut endoderm in Sox17-null mutant mice. Development 129(10): 2367-2379.

Kennedy M, Keller G M (2003) Hematopoietic commitment of ES cells in culture. Methods Enzymol 365: 39-59.

Kinder S J, Tsang T E, Wakamiya M, Sasaki H, Behringer R R et al. (2001) The organizer of the mouse gastrula is composed of a dynamic population of progenitor cells for the axial mesoderm. Development 128(18): 3623-3634.

Knop M, Barr F, Riedel C G, Heckel T, Reichel C (2002) Improved version of the red fluorescent protein (drFP583/DsRed/RFP). Biotechniques 33(3): 592, 594, 596-598 passim.

Kubo A, Chen V, Kennedy M, Zahradka E, Daley G Q et al. (2005) The homeobox gene HEX regulates proliferation and differentiation of hemangioblasts and endothelial cells during ES cell differentiation. Blood 105(12): 4590-4597.

Kubo A, Shinozaki K, Shannon J M, Kouskoff V, Kennedy M et al. (2004) Development of definitive endoderm from embryonic stem cells in culture. Development 131(7): 1651-1662.

Kumar M, Jordan N, Melton D, Grapin-Botton A (2003) Signals from lateral plate mesoderm instruct endoderm toward a pancreatic fate. Dev Biol 259(1): 109-122.

Kunath T, Saba-El-Leil M K, Almousailleakh M, Wray J, Meloche S et al. (2007) FGF stimulation of the Erk1/2 signalling cascade triggers transition of pluripotent embryonic stem cells from self-renewal to lineage commitment. Development 134(16): 2895-2902.

LaBonne C, Whitman M (1994) Mesoderm induction by activin requires FGF-mediated intracellular signals. Development 120(2): 463-472.

Lawson K A, Pedersen R A (1987) Cell fate, morphogenetic movement and population kinetics of embryonic endoderm at the time of germ layer formation in the mouse. Development 101(3): 627-652.

Li M, Sendtner M, Smith A (1995) Essential function of LIF receptor in motor neurons. Nature 378(6558): 724-727.

Lickert H, Kutsch S, Kanzler B, Tamai Y, Taketo M M et al. (2002) Formation of multiple hearts in mice following deletion of beta-catenin in the embryonic endoderm. Dev Cell 3(2): 171-181.

Lu C C, Brennan J, Robertson E J (2001) From fertilization to gastrulation: axis formation in the mouse embryo. Curr Opin Genet Dev 11(4): 384-392.

Maduro M F, Meneghini M D, Bowerman B, Broitman-Maduro G, Rothman J H (2001) Restriction of mesendoderm to a single blastomere by the combined action of SKN-1 and a GSK-3beta homolog is mediated by MED-1 and -2 in *C. elegans*. Mol Cell 7(3): 475-485.

Martinez Barbera J P, Clements M, Thomas P, Rodriguez T, Meloy D et al. (2000) The homeobox gene Hex is required in definitive endodermal tissues for normal forebrain, liver and thyroid formation. Development 127(11): 2433-2445.

McGrath K E, Koniski A D, Maltby K M, McGann J K, Palis J (1999) Embryonic expression and function of the chemokine SDF-1 and its receptor, CXCR4. Dev Biol 213(2): 442-456.

Mesnard D, Guzman-Ayala M, Constam D B (2006) Nodal specifies embryonic visceral endoderm and sustains pluripotent cells in the epiblast before overt axial patterning. Development 133(13): 2497-2505.

Mizoguchi T, Izawa T, Kuroiwa A, Kikuchi Y (2006) Fgf signaling negatively regulates Nodal-dependent endoderm induction in zebrafish. Dev Biol 300(2): 612-622.

Mohammadi M, Froum S, Hamby J M, Schroeder M C, Panek R L et al. (1998) Crystal structure of an angiogenesis inhibitor bound to the FGF receptor tyrosine kinase domain. Embo J 17(20): 5896-5904.

Morrison, G. M., Oikonomopoulou, I., Portero, R., and Brickman, J. M. (2008). Anterior Definitive Endoderm from E S cells reveals a novel role for FGF signaling. Cell Stem Cell In Press.

Nishikawa S I, Nishikawa S, Hirashima M, Matsuyoshi N, Kodama H (1998) Progressive lineage analysis by cell sorting and culture identifies FLK1+VE-cadherin+ cells at a diverging point of endothelial and hemopoietic lineages. Development 125(9): 1747-1757.

Norris D P, Brennan J, Bikoff E K, Robertson E J (2002) The Foxh1-dependent autoregulatory enhancer controls the level of Nodal signals in the mouse embryo. Development 129(14): 3455-3468.

Offield M F, Jetton T L, Labosky P A, Ray M, Stein R W et al. (1996) PDX-1 is required for pancreatic outgrowth and differentiation of the rostral duodenum. Development 122(3): 983-995.

Okabayashi K, Asashima M (2003) Tissue generation from amphibian animal caps. Curr Opin Genet Dev 13(5): 502-507.

Perea-Gomez A, Shawlot W, Sasaki H, Behringer R R, Ang S (1999) HNF3beta and Lim1 interact in the visceral endoderm to regulate primitive streak formation and anterior-posterior polarity in the mouse embryo. Development 126(20): 4499-4511.

Poulain M, Furthauer M, Thisse B, Thisse C, Lepage T (2006) Zebrafish endoderm formation is regulated by combinatorial Nodal, FGF and BMP signalling. Development 133(11): 2189-2200.

Robb L, Hartley L, Begley C G, Brodnicki T C, Copeland N G et al. (2000) Cloning, expression analysis, and chromosomal localization of murine and human homologues of a Xenopus mix gene. Dev Dyn 219(4): 497-504.

Rodaway A, Takeda H, Koshida S, Broadbent J, Price B et al. (1999) Induction of the mesendoderm in the zebrafish germ ring by yolk cell-derived TGF-beta family signals and discrimination of mesoderm and endoderm by FGF. Development 126(14): 3067-3078.

Rodriguez T A, Casey E S, Harland R M, Smith J C, Beddington R S (2001) Distinct enhancer elements control Hex expression during gastrulation and early organogenesis. Dev Biol 234(2): 304-316.

Tesar, P. J., Chenoweth, J. G., Brook, F. A., Davies, T. J., Evans, E. P., Mack, D. L., Gardner, R. L., and McKay, R. D. (2007). New cell lines from mouse epiblast share defining features with human embryonic stem cells. Nature.

Shawlot W, Behringer R R (1995) Requirement for Lim1 in head-organizer function [see comments]. Nature 374(6521): 425-430.

Smyth G K (2004) Linear Models and Empirical Bayes Methods for Assessing Differential Expression in Microarray Experiments. Statistical Applications in Genetics and Molecular Biology 3(1): Article 3.

Stavridis M P, Lunn J S, Collins B J, Storey K G (2007) A discrete period of FGF-induced Erk1/2 signalling is required for vertebrate neural specification. Development 134(16): 2889-2894.

Sun X, Meyers E N, Lewandoski M, Martin G R (1999) Targeted disruption of Fgf8 causes failure of cell migration in the gastrulating mouse embryo. Genes Dev 13(14): 1834-1846.

Tada S, Era T, Furusawa C, Sakurai H, Nishikawa S et al. (2005) Characterization of mesendoderm: a diverging point of the definitive endoderm and mesoderm in embryonic stem cell differentiation culture. Development 132(19): 4363-4374.

Thomas P, Beddington R (1996) Anterior primitive endoderm may be responsible for patterning the anterior neural plate in the mouse embryo. Cliff Biol 6(11): 1487-1496.

Thomas P, Brickman J M, Popperl H, Krumlauf R, Beddington R S P (1997) Axis duplication and anterior identity in the mouse embryo. Cold Spring Harb Symp Quant Biol 62: 115-125.

Thomas P Q, Brown A, Beddington R S P (1998) Hex: a homeobox gene revealing peri-implantation asymmetry in the mouse embryo and an early transient marker of endothelial cell precursors. Development 125(1): 85-94.

Vincent S D, Dunn N R, Hayashi S, Norris D P, Robertson E J (2003) Cell fate decisions within the mouse organizer are governed by graded Nodal signals. Genes Dev 17(13): 1646-1662.

Wells J M, Melton D A (2000) Early mouse endoderm is patterned by soluble factors from adjacent germ layers. Development 127(8): 1563-1572.

Yamaguchi T P, Harpal K, Henkemeyer M, Rossant J (1994) fgfr-1 is required for embryonic growth and mesodermal patterning during mouse gastrulation. Genes Dev 8(24): 3032-3044.

Yasunaga M, Tada S, Torikai-Nishikawa S, Nakano Y, Okada M et al. (2005) Induction and monitoring of definitive and visceral endoderm differentiation of mouse ES cells. Nat Biotechnol 23(12): 1542-1550.

Ying Q L, Nichols J, Chambers I, Smith A (2003) BMP induction of Id proteins suppresses differentiation and sustains embryonic stem cell self-renewal in collaboration with STAT3. Cell 115(3): 281-292.

Yusuf F, Rehimi R, Dai F, Brand-Saberi B (2005) Expression of chemokine receptor CXCR4 during chick embryo development. Anat Embryol (Berl) 210(1): 35-41.

Zamparini A L, Watts T, Gardner C E, Tomlinson S R, Johnston G I et al. (2006) Hex acts with beta-catenin to regulate anteroposterior patterning via a Groucho-related co-repressor and Nodal. Development 133(11): 3709-3722.

TABLE 1

$Hex^{RS}$ mouse genotypes arising from $Hex^{RS}/+$ intercrosses.

| genotype | number | percentage | expected percentage |
|---|---|---|---|
| +/+ | 114 | 39 | 33 |
| +/− | 176 | 61 | 66 |
| −/− | 0 | 0 | 0 |

TABLE 2 optimisation in serum day 0-2.

| | Day 0-2 | | | | | | | Day 3-7 | | | | | | | |
|---|---|---|---|---|---|---|---|---|---|---|---|---|---|---|---|
| media | FCS | A | E | B4 | RA | GI | media | FCS | A | E | B4 | RA | GI | H+C+ % |
| GMEM | + | - | - | - | - | - | GMEM | + | + | - | - | - | - | 0.00 |
| GMEM | + | - | - | - | - | - | N2B27 | - | - | - | - | - | - | 0.00 |
| GMEM | + | - | - | - | - | - | N2B27 | - | + | - | - | - | - | 9.95 ± 4.62 |
| GMEM | + | - | - | - | - | - | N2B27 | - | + | + | - | - | - | 18.72 ± 4.08 |
| GMEM | + | - | - | + | - | - | N2B27 | - | + | + | - | - | - | 0.61 |
| GMEM | + | - | - | + | - | - | N2B27 | - | + | + | + | - | - | 0.39 |
| GMEM | + | - | - | - | - | - | N2B27 | - | + | + | + | - | - | 0.60 ± 0.61 |
| GMEM | + | - | - | - | - | - | N2B27 | - | + | + | - | + | - | 0.73 |
| GMEM | + | - | - | - | - | + | N2B27 | - | + | + | - | - | - | 0.05 ± 0.03 |
| GMEM | + | - | - | - | - | + | N2B27 | - | + | + | - | - | + | 0.83 |
| GMEM | + | - | - | - | - | - | N2B27 | - | + | + | - | - | + | 0.00 |
| GMEM | + | - | - | - | - | - | SF03 | - | + | + | - | - | - | 4.51 * |
| GMEM | + | - | - | - | - | - | SF03 | - | + | - | - | - | - | Dead |

* = very low cell survival

TABLE 3

Cell density

| Day 0-2 | Day 3-7 | Cell density | H+C+ % |
|---|---|---|---|
| GMEM + 10% FCS | N2B27 + activin | $1 \times 10^5$/ml | 0.68 |
| GMEM + 10% FCS | N2B27 + activin | $5 \times 10^4$/ml | 1.32 |
| GMEM + 10% FCS | N2B27 + activin | $5 \times 10^3$/ml | 15.21 |

TABLE 4

Kidney capsule grafts.

| cell fraction | explants performed | no. growths recovered | | | germ layers present | | |
|---|---|---|---|---|---|---|---|
| | | small | medium | large | ecto | meso | endo |
| H+C+ | 9 | 1 | - | - | - | - | + |
| H+C- | 9 | - | 3 | - | - | - | + |
| H-C+ | 9 | 1 | 1 | 2 | - | + | + |
| H-C- | 9 | - | - | 5 | + | + | + |

TABLE 5

Optimisation of ADE production using chemically defined media in aggregation culture.

| | Day 0-2 | | | | | Day 3-7 | | | | | |
|---|---|---|---|---|---|---|---|---|---|---|---|
| media | Act | Bmp4 | EGF | GI | media | Act | Bmp4 | EGF | GI | H+C+ | s.d. |
| SF03 | - | - | - | - | SF03 | - | - | - | - | dead | |
| SF03 | - | - | - | - | SF03 | + | - | - | - | dead | |
| SF03 | + | + | - | - | SF03 | + | - | + | - | dead | |
| SF03 | - | + | - | - | SF03 | + | - | + | - | dead | |
| SF03 | + | - | - | - | SF03 | + | - | - | - | dead | |
| N2B27 | - | - | - | - | N2B27 | - | - | - | - | dead | |
| N2B27 | - | + | - | - | N2B27 | + | - | + | - | 1.18 | |
| N2B27 | - | + | + | - | N2B27 | + | - | - | - | 1.46 | |
| N2B27 | - | + | + | - | N2B27 | + | - | + | - | 1.15 | |
| N2B27 | - | + | - | - | N2B27 | + | - | - | - | 0.93 | 0.72 |
| N2B27 | + | + | + | - | N2B27 | + | - | + | - | 0.91 | |
| N2B27 | + | + | - | - | N2B27 | + | - | + | - | 1.05 | |
| N2B27 | + | + | + | - | N2B27 | + | - | - | - | 0.77 | |
| N2B27 | + | + | - | - | N2B27 | + | - | - | - | 0.92 | |
| N2B27 | - | - | - | - | SF03 | + | - | + | - | 7.03* | |
| N2B27 | - | - | - | - | SF03 | + | + | + | - | 2.75* | |
| N2B27 | + | - | - | - | SF03 | + | - | + | - | 2.07* | |
| N2B27 | - | + | - | - | SF03 | + | - | - | - | 5.37 | |
| N2B27 | - | + | - | - | SF03 | + | - | + | - | 12.32 | 5.97 |
| N2B27 | - | + | - | - | SF03 | + | + | + | - | 2.73 | 2.77 |
| N2B27 | + | + | - | - | SF03 | + | - | + | - | 13.34 | 1.68 |
| N2B27 | - | + | - | + | SF03 | + | - | + | - | 2.95 | |
| N2B27 | - | + | - | + | SF03 | + | - | + | + | 4.68 | |
| N2B27 | - | + | - | - | SF03 | + | - | + | + | 0.32 | |
| N2B27 | - | + | - | - | SF03 | - | - | + | - | dead | |
| N2B27 | + | + | - | - | SF03 | - | - | + | - | dead | |

The optimal condition from these experiments is highlighted in bold.

Abbreviations: Act; activin A, GI; GSK3 inhibitor CHIR99021, H+C+; percentage of RS/CXCR4 double positive cells, s.d.; standard deviation.

TABLE 6

Optimisation of ADE production using chemically defined media in adherent monolayer culture.

| | Day 0-2 | | | | Day 3-7 | | | |
|---|---|---|---|---|---|---|---|---|
| media | Act | Bmp4 | GI | media | Act | EGF | H+C+ | s.d. |
| SF03 | − | − | − | SF03 | − | − | dead | |
| SF03 | − | − | − | SF03 | + | − | dead | |
| SF03 | + | + | − | SF03 | + | − | dead | |
| SF03 | + | + | − | SF03 | + | + | dead | |
| SF03 | − | + | − | SF03 | + | + | dead | |
| SF03 | + | + | − | SF03 | + | − | dead | |
| N2B27 | − | − | − | N2B27 | − | − | dead | |
| N2B27 | − | + | − | N2B27 | + | + | 0.3 | |
| N2B27 | − | + | − | N2B27 | + | − | 0.2 | |
| N2B27 | + | + | − | N2B27 | + | + | 0.1 | |
| N2B27 | + | + | − | N2B27 | + | − | 0.3 | |
| N2B27 | − | − | − | SF03 | + | + | 0 | N/A |
| N2B27 | + | − | − | SF03 | + | + | 0 | N/A |
| N2B27 | − | + | − | SF03 | + | + | 5.03 | 1.8 |
| N2B27 | + | + | − | SF03 | + | + | 5.7 | 1.9 |
| N2B27 | − | − | + | SF03 | + | + | 1.7 | |
| N2B27 | + | − | + | SF03 | + | + | 2.0 | |
| N2B27 | − | + | + | SF03 | + | + | 0.2 | |
| N2B27 | + | + | + | SF03 | + | + | 4.2 | |

The optimal condition from these experiments is highlighted in bold.
Abbreviations: Act; activin A, GI; GSK3 inhibitor CHIR99021, H+C+; percentage of RS/CXCR4 double positive cells, s.d.; standard deviation, N/A; not applicable.

TABLE 7

ADE percentage and total cell number following 7 days serum-free differentiation.

| | aggregation | | monolayer | |
|---|---|---|---|---|
| Media (day 0-2) | H+C+ | total cells | H+C+ | total cells |
| N2B27 | 13.49 | $0.75 \times 10^6$ | 0 | $0.3 \times 10^6$ |
| N2B27 + GI | 5.86 | $2.3 \times 10^6$ | 1.7 | $0.9 \times 10^6$ |
| N2B27 + A | 1.21 | $1.6 \times 10^6$ | 0 | $0.3 \times 10^6$ |
| N2B27 + A + GI | 7.81 | $1.7 \times 10^6$ | 2.0 | $0.8 \times 10^6$ |
| N2B27 + B | 2.68 | $2.2 \times 10^6$ | 3.0 | $1 \times 10^6$ |
| N2B27 + B + GI | 5.11 | $1.2 \times 10^6$ | 0.2 | $1 \times 10^6$ |
| N2B27 + A + B | 9.1 | $\mathbf{5.7 \times 10^6}$ | 5.0 | $\mathbf{2 \times 10^6}$ |
| N2B27 + A + B + GI | 7.68 | $2.6 \times 10^6$ | 4.2 | $1.5 \times 10^6$ |

The optimal condition in terms of H+C+ yield is highlighted in bold.

TABLE 8

Addition of Fgf4 increases ADE production.

| | Day 0-2 | | | | Day 3-7 | | | | | |
|---|---|---|---|---|---|---|---|---|---|---|
| media | Act | Bmp4 | Fgf4 | PD173074 | media | Act | EGF | Fgf4 | PD173074 | H+C+ | s.d. |
| N2B27 | + | + | − | − | SF03 | + | + | − | − | 5.7 | 1.9 |
| N2B27 | + | + | − | − | SF03 | + | + | + | − | 11.5 | 4.6 |
| N2B27 | + | + | + | + | SF03 | + | + | + | + | 0.08 | N/A |
| N2B27 | + | + | − | + | SF03 | + | + | − | + | 0.13 | 0.07 |
| N2B27 | + | + | − | + | SF03 | + | + | − | − | 2.55 | 0.2 |
| N2B27 | + | + | − | − | SF03 | + | + | − | + | 1.58 | 0.6 |

The optimal condition is highlighted in bold.
Abbreviations : Act; activin A, H+C+; percentage of RS/CXCR4 positive cells, s.d.; standard deviation, N/A; data not available.

TABLE 9

Primers used for real-time RT-PCR

| Gene | Forward | Reverse | Amplicon Size (bp) |
|---|---|---|---|
| B-actin | GGCCCAGAGCAAGAGAGGTATCC | ACGCACGATTTCCCTCTCAGC | 460 |
| TBP | GGGGAGCTGTGATGTGAAGT | CCAGGAAATAATTCTGGCTCA | 93 |
| Hex | GAGGTTCTCCAACGACCAGA | GTCCAACGCATCCTTTTTGT | 202 |
| Cxcr4 | TCAGTGGCTGACCTCCTCTT | TTTCAGCCAGCAGTTTCCTT | 220 |
| Brachyury | GTGACTGCCTACCAGAATGA | ATTGTCCGCATAGGTTGGAG | 336 |
| Pou5f1 | GGCGTTCTCTTTGGAAAGGTGTTC | CTCGAACCACATCCTTCTC | 314 |
| Foxa2 | CATCCGACTGGAGCAGCTA | GCGCCCACATAGGATGAC | 178 |
| Sox17 | GGTCTGAAGTGCGGTTGG | TGTCTTCCCTGTCTTGGTTGA | 182 |
| Gsc | GAGACGAAGTACCCAGACGTG | GGCGGTTCTTAAACCAGACC | 94 |
| Cer1 | AGGAGGAAGCCAAGAGGTTC | CATTTGCCAAAGCAAAGGTT | 189 |

TABLE 9-continued

Primers used for real-time RT-PCR

| Gene | Forward | Reverse | Amplicon Size (bp) |
|---|---|---|---|
| Mixl1 | AGTTGCTGGAGCTCGTCTTC | AGGGCAATGGAGGAAAACTC | 194 |
| Nodal | GGCGTACATGTTGAGCCTCT | GCCTGGTGGAAAATGTCAAT | 228 |
| Cdx2 | GGAAGCCAAGTGAAAACCAG | CTTGGCTCTGCGGTTCTG | 189 |
| Wnt3 | CGCTCAGCTATGAACAAGCA | GGTGTTTCTCCACCACCATC | 202 |
| Meox1 | GGAAGGAGAGGACAGCCTTC | CCCTTCACACGTTTCCACTT | 178 |
| Ecad | AGACTTTGGTGTGGGTCAGG | CATGCTCAGCGTCTTCTCTG | 176 |
| Sox7 | AGATGCTGGGAAAGTCATGG | AGAGGGAGCTGAGGAGGAAG | 186 |
| Fhl2 | AGAAAACCATCATGCCAGGT | ACAGGTGAAGCAGGTCTCGT | 74 |
| Lhx1 | CAGGAGACTGGCCTCAACAT | GTTTCATCCTTCGCTCCTTG | 76 |
| Pdlim4 | TTACGCTCTCGGTCAGCAG | TCCTATGTGCTTGAGCCTTG | 75 |
| Foxa3 | CCTCCTTCGTCCACACCTTA | GAAGTTATAGGGCGCATCCA | 64 |
| Tle2 | TATGGGCCAGCATTTTTC | CCTGAGCCTGTCACGATGTA | 92 |
| Tmprss2 | GCCAAGAGCTCGGACAGA | AGCAGCATGAGGAGGTCAGT | 86 |

TABLE 10

Effect of BMP4 and activin A on ADE induction and final cell number following 7 days serum-free differentiation in adherent monolayer culture.

| Media (day 0-2) | Percentage H+C+ | Total cells in culture |
|---|---|---|
| N2B27 | 0.0 | $0.3 \times 10^6$ |
| N2B27 + A | 0.0 | $0.3 \times 10^6$ |
| N2B27 + B | 3.0 | $1 \times 10^6$ |
| N2B27 + A + B | 5.0 | $\mathbf{2 \times 10^6}$ |

The optimal culture condition in terms of H+C+ yield is highlighted in bold. All samples were cultured in SF03 plus activin and EGF from day 2-7. Abbreviations: A; activin, B; Bmp4, H+C+; RS/Cxcr4 double positive cells.

TABLE 11

Addition of Fgf4 increases ADE production.

| | Day 0-2 | | | Day 3-7 | | | |
|---|---|---|---|---|---|---|---|
| media | Fgf4 | PD173074 | media | Fgf4 | PD173074 | H+C+ | s.d. |
| N2B27 | − | − | SF03 | − | − | 5.7 | 1.9 |
| N2B27 | + | − | SF03 | + | − | 11.5 | 4.6 |
| N2B27 | + | + | SF03 | + | + | 0.08 | N/A |
| N2B27 | − | + | SF03 | − | − | 2.55 | 0.2 |
| N2B27 | − | − | SF03 | − | + | 1.58 | 0.6 |
| N2B27 | − | + | SF03 | − | + | 0.13 | 0.07 |
| N2B27 | − | − | SF03 | + | − | 21.5 | 0.8 |

The optimal conditions are highlighted in bold. Activin A and BMP4 were included during the first two days for all conditions, as well as activin A and EGF for the following five days. Abbreviations: N2B27; N2B27 media plus activin A and Bmp4, SF03; SF03 media plus activn and EGF, H+C+; mean percentage of RS/CXCR4 positive cells from a minimum of 3 independent experiments, s.d.; standard deviation, N/A; data not available.

The invention claimed is:

1. A substantially pure cell population of isolated anterior definitive endoderm (ADE) cells derived from embryonic stem (ES) cells cultured with activin,
    wherein the ADE cells are capable of
        i) proliferating in an in vitro culture without further differentiation for at least 8 passages and/or over 2 months; and
        ii) maintaining the potential to differentiate into derivatives of ADE cells;
    wherein the substantially pure cell population comprises at least 40% ADE cells; and
    wherein said ADE cells are derived from human or mouse ES cells.

2. The cell population according to claim 1, wherein said derivatives of ADE cells consist of liver, pancreas, lung, thymus, thyroid, and parathyroid cells.

3. The cell population according to claim 1, wherein the ADE cells are derived from human ES cells.

4. The cell population according to claim 1, wherein the ADE cells are derived from mouse ES cells.

5. The cell population according to claim 1, wherein the ES cells from which the ADE cells are derived are either wild-type or genetically modified ES cells.

6. The cell population according to claim 1, wherein said derivatives of ADE cells comprise pancreas cells.

* * * * *

SEQUENCE LISTING

```
<160> NUMBER OF SEQ ID NOS: 46

<210> SEQ ID NO 1
<211> LENGTH: 23
<212> TYPE: DNA
<213> ORGANISM: Artificial
<220> FEATURE:
<223> OTHER INFORMATION: Primer

<400> SEQUENCE: 1
ggcccagagc aagagaggta tcc                                              23

<210> SEQ ID NO 2
<211> LENGTH: 21
<212> TYPE: DNA
<213> ORGANISM: Artificial
<220> FEATURE:
<223> OTHER INFORMATION: Primer
```

-continued

<400> SEQUENCE: 2
acgcacgatt tccctctcag c                                              21

<210> SEQ ID NO 3
<211> LENGTH: 20
<212> TYPE: DNA
<213> ORGANISM: Artificial
<220> FEATURE:
<223> OTHER INFORMATION: Primer

<400> SEQUENCE: 3
ggggagctgt gatgtgaagt                                                20

<210> SEQ ID NO 4
<211> LENGTH: 21
<212> TYPE: DNA
<213> ORGANISM: Artificial
<220> FEATURE:
<223> OTHER INFORMATION: Primer

<400> SEQUENCE: 4
ccaggaaata attctggctc a                                              21

<210> SEQ ID NO 5
<211> LENGTH: 20
<212> TYPE: DNA
<213> ORGANISM: Artificial
<220> FEATURE:
<223> OTHER INFORMATION: Primer

<400> SEQUENCE: 5
gaggttctcc aacgaccaga                                                20

<210> SEQ ID NO 6
<211> LENGTH: 20
<212> TYPE: DNA
<213> ORGANISM: Artificial
<220> FEATURE:
<223> OTHER INFORMATION: Primer

<400> SEQUENCE: 6
gtccaacgca tccttttttgt                                               20

<210> SEQ ID NO 7
<211> LENGTH: 20
<212> TYPE: DNA
<213> ORGANISM: Artificial
<220> FEATURE:
<223> OTHER INFORMATION: Primer

<400> SEQUENCE: 7
tcagtggctg acctcctctt                                                20

<210> SEQ ID NO 8
<211> LENGTH: 20
<212> TYPE: DNA
<213> ORGANISM: Artificial
<220> FEATURE:
<223> OTHER INFORMATION: Primer

<400> SEQUENCE: 8
tttcagccag cagtttcctt                                                20

<210> SEQ ID NO 9

```
<211> LENGTH: 20
<212> TYPE: DNA
<213> ORGANISM: Artificial
<220> FEATURE:
<223> OTHER INFORMATION: Primer

<400> SEQUENCE: 9
gtgactgcct accagaatga                                                    20

<210> SEQ ID NO 10
<211> LENGTH: 20
<212> TYPE: DNA
<213> ORGANISM: Artificial
<220> FEATURE:
<223> OTHER INFORMATION: Primer

<400> SEQUENCE: 10
attgtccgca taggttggag                                                    20

<210> SEQ ID NO 11
<211> LENGTH: 24
<212> TYPE: DNA
<213> ORGANISM: Artificial
<220> FEATURE:
<223> OTHER INFORMATION: Primer

<400> SEQUENCE: 11
ggcgttctct ttggaaaggt gttc                                               24

<210> SEQ ID NO 12
<211> LENGTH: 19
<212> TYPE: DNA
<213> ORGANISM: Artificial
<220> FEATURE:
<223> OTHER INFORMATION: Primer

<400> SEQUENCE: 12
ctcgaaccac atccttctc                                                     19

<210> SEQ ID NO 13
<211> LENGTH: 19
<212> TYPE: DNA
<213> ORGANISM: Artificial
<220> FEATURE:
<223> OTHER INFORMATION: Primer

<400> SEQUENCE: 13
catccgactg gagcagcta                                                     19

<210> SEQ ID NO 14
<211> LENGTH: 18
<212> TYPE: DNA
<213> ORGANISM: Artificial
<220> FEATURE:
<223> OTHER INFORMATION: Primer

<400> SEQUENCE: 14
gcgcccacat aggatgac                                                      18

<210> SEQ ID NO 15
<211> LENGTH: 18
<212> TYPE: DNA
<213> ORGANISM: Artificial
<220> FEATURE:
<223> OTHER INFORMATION: Primer

<400> SEQUENCE: 15
```
ggtctgaagt gcggttgg                                                     18

<210> SEQ ID NO 16
<211> LENGTH: 21
<212> TYPE: DNA
<213> ORGANISM: Artificial
<220> FEATURE:
<223> OTHER INFORMATION: Primer

<400> SEQUENCE: 16
tgtcttccct gtcttggttg a                                                 21

<210> SEQ ID NO 17
<211> LENGTH: 21
<212> TYPE: DNA
<213> ORGANISM: Artificial
<220> FEATURE:
<223> OTHER INFORMATION: Primer

<400> SEQUENCE: 17
gagacgaagt acccagacgt g                                                 21

<210> SEQ ID NO 18
<211> LENGTH: 20
<212> TYPE: DNA
<213> ORGANISM: Artificial
<220> FEATURE:
<223> OTHER INFORMATION: Primer

<400> SEQUENCE: 18
ggcggttctt aaaccagacc                                                   20

<210> SEQ ID NO 19
<211> LENGTH: 20
<212> TYPE: DNA
<213> ORGANISM: Artificial
<220> FEATURE:
<223> OTHER INFORMATION: Primer

<400> SEQUENCE: 19
aggaggaagc caagaggttc                                                   20

<210> SEQ ID NO 20
<211> LENGTH: 20
<212> TYPE: DNA
<213> ORGANISM: Artificial
<220> FEATURE:
<223> OTHER INFORMATION: Primer

<400> SEQUENCE: 20
catttgccaa agcaaaggtt                                                   20

<210> SEQ ID NO 21
<211> LENGTH: 20
<212> TYPE: DNA
<213> ORGANISM: Artificial
<220> FEATURE:
<223> OTHER INFORMATION: Primer

<400> SEQUENCE: 21
agttgctgga gctcgtcttc                                                   20

<210> SEQ ID NO 22
<211> LENGTH: 20
<212> TYPE: DNA

```
<213> ORGANISM: Artificial
<220> FEATURE:
<223> OTHER INFORMATION: Primer

<400> SEQUENCE: 22
agggcaatgg aggaaaactc                                               20

<210> SEQ ID NO 23
<211> LENGTH: 20
<212> TYPE: DNA
<213> ORGANISM: Artificial
<220> FEATURE:
<223> OTHER INFORMATION: Primer

<400> SEQUENCE: 23
ggcgtacatg ttgagcctct                                               20

<210> SEQ ID NO 24
<211> LENGTH: 20
<212> TYPE: DNA
<213> ORGANISM: Artificial
<220> FEATURE:
<223> OTHER INFORMATION: Primer

<400> SEQUENCE: 24
gcctggtgga aaatgtcaat                                               20

<210> SEQ ID NO 25
<211> LENGTH: 20
<212> TYPE: DNA
<213> ORGANISM: Artificial
<220> FEATURE:
<223> OTHER INFORMATION: Primer

<400> SEQUENCE: 25
ggaagccaag tgaaaccag                                                20

<210> SEQ ID NO 26
<211> LENGTH: 18
<212> TYPE: DNA
<213> ORGANISM: Artificial
<220> FEATURE:
<223> OTHER INFORMATION: Primer

<400> SEQUENCE: 26
cttggctctg cggttctg                                                 18

<210> SEQ ID NO 27
<211> LENGTH: 20
<212> TYPE: DNA
<213> ORGANISM: Artificial
<220> FEATURE:
<223> OTHER INFORMATION: Primer

<400> SEQUENCE: 27
cgctcagcta tgaacaagca                                               20

<210> SEQ ID NO 28
<211> LENGTH: 20
<212> TYPE: DNA
<213> ORGANISM: Artificial
<220> FEATURE:
<223> OTHER INFORMATION: Primer

<400> SEQUENCE: 28
ggtgtttctc caccaccatc                                               20
```

```
<210> SEQ ID NO 29
<211> LENGTH: 20
<212> TYPE: DNA
<213> ORGANISM: Artificial
<220> FEATURE:
<223> OTHER INFORMATION: Primer

<400> SEQUENCE: 29
ggaaggagag gacagccttc                                              20

<210> SEQ ID NO 30
<211> LENGTH: 20
<212> TYPE: DNA
<213> ORGANISM: Artificial
<220> FEATURE:
<223> OTHER INFORMATION: Primer

<400> SEQUENCE: 30
cccttcacac gtttccactt                                              20

<210> SEQ ID NO 31
<211> LENGTH: 20
<212> TYPE: DNA
<213> ORGANISM: Artificial
<220> FEATURE:
<223> OTHER INFORMATION: Primer

<400> SEQUENCE: 31
agactttggt gtgggtcagg                                              20

<210> SEQ ID NO 32
<211> LENGTH: 20
<212> TYPE: DNA
<213> ORGANISM: Artificial
<220> FEATURE:
<223> OTHER INFORMATION: Primer

<400> SEQUENCE: 32
catgctcagc gtcttctctg                                              20

<210> SEQ ID NO 33
<211> LENGTH: 20
<212> TYPE: DNA
<213> ORGANISM: Artificial
<220> FEATURE:
<223> OTHER INFORMATION: Primer

<400> SEQUENCE: 33
agatgctggg aaagtcatgg                                              20

<210> SEQ ID NO 34
<211> LENGTH: 20
<212> TYPE: DNA
<213> ORGANISM: Artificial
<220> FEATURE:
<223> OTHER INFORMATION: Primer

<400> SEQUENCE: 34
agagggagct gaggaggaag                                              20

<210> SEQ ID NO 35
<211> LENGTH: 20
<212> TYPE: DNA
<213> ORGANISM: Artificial
<220> FEATURE:
```

```
<223> OTHER INFORMATION: Primer

<400> SEQUENCE: 35
agaaaaccat catgccaggt                                              20

<210> SEQ ID NO 36
<211> LENGTH: 20
<212> TYPE: DNA
<213> ORGANISM: Artificial
<220> FEATURE:
<223> OTHER INFORMATION: Primer

<400> SEQUENCE: 36
acaggtgaag caggtctcgt                                              20

<210> SEQ ID NO 37
<211> LENGTH: 20
<212> TYPE: DNA
<213> ORGANISM: Artificial
<220> FEATURE:
<223> OTHER INFORMATION: Primer

<400> SEQUENCE: 37
caggagactg gcctcaacat                                              20

<210> SEQ ID NO 38
<211> LENGTH: 20
<212> TYPE: DNA
<213> ORGANISM: Artificial
<220> FEATURE:
<223> OTHER INFORMATION: Primer

<400> SEQUENCE: 38
gtttcatcct tcgctccttg                                              20

<210> SEQ ID NO 39
<211> LENGTH: 19
<212> TYPE: DNA
<213> ORGANISM: Artificial
<220> FEATURE:
<223> OTHER INFORMATION: Primer

<400> SEQUENCE: 39
ttacgctctc ggtcagcag                                               19

<210> SEQ ID NO 40
<211> LENGTH: 20
<212> TYPE: DNA
<213> ORGANISM: Artificial
<220> FEATURE:
<223> OTHER INFORMATION: Primer

<400> SEQUENCE: 40
tcctatgtgc ttgagccttg                                              20

<210> SEQ ID NO 41
<211> LENGTH: 20
<212> TYPE: DNA
<213> ORGANISM: Artificial
<220> FEATURE:
<223> OTHER INFORMATION: Primer

<400> SEQUENCE: 41
cctccttcgt ccacacctta                                              20
```

```
<210> SEQ ID NO 42
<211> LENGTH: 20
<212> TYPE: DNA
<213> ORGANISM: Artificial
<220> FEATURE:
<223> OTHER INFORMATION: Primer

<400> SEQUENCE: 42
gaagttatag ggcgcatcca                                               20

<210> SEQ ID NO 43
<211> LENGTH: 19
<212> TYPE: DNA
<213> ORGANISM: Artificial
<220> FEATURE:
<223> OTHER INFORMATION: Primer

<400> SEQUENCE: 43
tatggggcca gcatttttc                                                19

<210> SEQ ID NO 44
<211> LENGTH: 20
<212> TYPE: DNA
<213> ORGANISM: Artificial
<220> FEATURE:
<223> OTHER INFORMATION: Primer

<400> SEQUENCE: 44
cctgagcctg tcacgatgta                                               20

<210> SEQ ID NO 45
<211> LENGTH: 18
<212> TYPE: DNA
<213> ORGANISM: Artificial
<220> FEATURE:
<223> OTHER INFORMATION: Primer

<400> SEQUENCE: 45
gccaagagct cggacaga                                                 18

<210> SEQ ID NO 46
<211> LENGTH: 20
<212> TYPE: DNA
<213> ORGANISM: Artificial
<220> FEATURE:
<223> OTHER INFORMATION: Primer

<400> SEQUENCE: 46
agcagcatga ggaggtcagt                                               20
```